United States Patent
Yurgelun-Todd et al.

(10) Patent No.: US 11,583,546 B2
(45) Date of Patent: Feb. 21, 2023

(54) ADMINISTRATION OF CITICOLINE TO IMPROVE COGNITIVE PERFORMANCE, ATTENTIONAL PERFORMANCE, AND MOTOR FUNCTION

(71) Applicant: KYOWA HAKKO BIO CO., LTD., Tokyo (JP)

(72) Inventors: Deborah Yurgelun-Todd, Salt Lake City, UT (US); Perry Renshaw, Salt Lake City, UT (US); Miho Takada, Chiyoda-ku (JP); Takeshi Ikeda, Chiyoda-ku (JP); Masahiko Morita, Chiyoda-ku (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 210 days.

(21) Appl. No.: 15/307,411

(22) PCT Filed: Apr. 30, 2015

(86) PCT No.: PCT/IB2015/053178
§ 371 (c)(1),
(2) Date: Oct. 28, 2016

(87) PCT Pub. No.: WO2015/166463
PCT Pub. Date: Nov. 5, 2015

(65) Prior Publication Data
US 2017/0049796 A1    Feb. 23, 2017

Related U.S. Application Data

(60) Provisional application No. 61/986,502, filed on Apr. 30, 2014.

(51) Int. Cl.
A61K 31/7068    (2006.01)
A61K 31/6615    (2006.01)
A61K 9/00    (2006.01)

(52) U.S. Cl.
CPC ........ A61K 31/7068 (2013.01); A61K 9/0053 (2013.01); A61K 31/6615 (2013.01)

(58) Field of Classification Search
CPC ............ A61K 31/7068; A61K 31/6615; A61K 9/0053
See application file for complete search history.

(56) References Cited

U.S. PATENT DOCUMENTS

| | | | | |
|---|---|---|---|---|
| 9,883,831 B1* | 2/2018 | Stewart | ................ | A61B 5/4088 |
| 10,905,705 B2* | 2/2021 | Kumagai | ................ | A61P 43/00 |
| 2002/0198172 A1* | 12/2002 | Sandage, Jr. | ...... | A61K 31/7068 514/49 |
| 2006/0189566 A1* | 8/2006 | Komatsu | ................ | A23L 33/40 514/50 |
| 2007/0004670 A1* | 1/2007 | Wurtman | ................ | A61P 25/28 514/49 |
| 2007/0248696 A1* | 10/2007 | Maletto | ................ | A61K 36/906 514/642 |
| 2010/0041620 A1* | 2/2010 | Renshaw | ........... | A61K 31/7068 514/50 |
| 2010/0041621 A1* | 2/2010 | Renshaw | ................ | A23L 33/13 514/49 |
| 2015/0306125 A1* | 10/2015 | Kumagai | ................ | A61P 25/28 514/49 |

FOREIGN PATENT DOCUMENTS

WO    WO 2014/069667 A1    5/2014

OTHER PUBLICATIONS

Petkov et al., "Effect of CDP-Choline on Learning and Memory Processes in Rodents," Meth Find Exp Clin Pharmacology, 14(6), 593-605 (1992). (Year: 1992).*
Secades et al., "CDP-Choline: Pharmacological and Clinical Review," Meth Find Exp Clin Pharmacology, 17(Suppl. B) 1-54 (1995). (Year: 1995).*
Rogers, Kara, "Norepiniphrine/Noradrenaline," entry in Britannica. com, accessed on-line Aug. 20, 2018; no other publication date provided. (Year: 2018).*
Pugh et al. (eds.), "Stedman's Medical Dictionary, 27th Ed," Lippincott, Williams & Wilkins, Philadelphia, PA, 2000, only page 1227 supplied, see entries for noradrenaline and norepinephrine. (Year: 2000).*
Paranjpe, J., "Dexemdetomidine: Expanding Role in Anesthesia," Medical Journal of Dr. D. Y. Patil University, 6(1), 5-13 (Jan.-Mar. 2013, supplied by applicant. (Year: 2013).*
Kuhar et al., "Alpha-and beta-Adrenergic Receptors," NCBI Bookshelf, National Library of Medicine, National Institutes of Health, (1999); excerpt from Basic Neurochemistry, 6th Ed., supplied by applicant. (Year: 1999).*
Shima et al., "Motor Function Evaluation and Classification in Finger Tapping Movements for Parkinson's Disease Using a Factor Analysis," T. Sice, 49(10), 975-981 (2013); supplied by applicant, only abstract provided in English. (Year: 2013).*
Lopez et al., "Effect of Cytidine(5')Diphosphocholine (CDP-Choline) on the Total Urinary Excretion of 3-Methoxy-4-hydroxyphenylglycol (MHPG) by Rats and Humans," Journal of Neural Transmission, 66, 129-134 (1986).*
Petkov et al., "Effect of CDP-Choline on Learning and Memory Processes in Rodents," Meth Find Exp Clin Pharmacology, 14(6), 593-605 (1992).*
Secades et al., "CDP-Choline: Pharmacological and Clinical Review," Meth Find Exp Clin Pharmacology, 17(Suppl. B) 1-54 (1995).*
Rogers, Kara, "Norepiniphrine/Noradrenaline," entry in Britannica. com, accessed on-line Aug. 20, 2018; no other publication date provided.*
Pugh et al. (eds.), "Stedman's Medical Dictionary, 27th Ed," Lippincott, Williams & Wilkins, Philadelphia, PA, 2000, only page 1227 supplied, see entries for noradrenaline and norepinephrine.*

(Continued)

Primary Examiner — Dale R Miller
(74) Attorney, Agent, or Firm — Leydig, Voit & Mayer, Ltd.

(57) ABSTRACT

A method of improving both motor function and cognitive function of healthy human subjects through administration of citicoline or its salt in high dosage or low dosage for a period of time, resulting in improved motor function and cognitive function.

10 Claims, 4 Drawing Sheets

(56) References Cited

OTHER PUBLICATIONS

Google search for "fight or flight symptoms checklist," first listing beginning with the term "usually."obtained Oct. 9, 2021.*

European Patent Office, Extended European Search Report in European Patent Application No. 15786597.3 (dated Nov. 24, 2017).

Steven E. Bruce, Improvements in quantitative EEG following consumption of a natural citicoline-enhanced beverage, Int J Food Sci Nutr., 2012, 63 (4), 421-5.

Silveri M. M., et al., Citicoline enhances frontal lobe bioenergetics as measured by phosphorus magnetic resonance spectroscopy, NMR Biomed., 21 (10), 2008, 1066-75.

Alvarez X. Anton, et al., Citicoline improves memory performance in elderly subjects, Methods Find Exp Clin Pharmacol., 1997, 19 (3), 201-10.

Toshimasa Sato, et al., Time courses of brain activation and their implications for function: A multichannel near-infrared spectroscopy study during finger tapping, Neurosci Res., 2007, 58 (3), 287-304.

Sato et al., "Time courses of brain activation and their implications for function: A multichannel near-infrared spectroscopy study during finger tapping," Neurosci. Res., 58(3): 297-304 (2007).

Japanese Patent Office, Notification of Reasons for Refusal in Japanese Patent Application No. 2016-564605 (Oct. 1, 2018).

McGlade, "Improved Attentional Performance following Citicoline Administration," Biol. Psychiatry, 69(9—Suppl. S): 36S, Abstract No. 130 (2011).

Topuz et al., "The effect of centrally injected CDP-choline on respiratory system: involvement of phospholipase to thromboxane signaling pathway," Respir. Physiol. Neurobiol., 195: 50-58 (2014).

Kuhar et al., "$\alpha$- and $\beta$-Adrenergic Receptors," NCBI Bookshelf, ID No. NBK28138 (1999) [excerpt from Basic Neurochemistry, 6th edition].

Paranjpe, "Dexmedetomidine: Expanding role in anesthesia," Med. J. D.Y. Patil Univ., 6(1): 5-13 (2013).

Shima et al., "Motor Function Evaluation and Classification in Finger Tapping Movements for Parkinson's Disease Using a Factor Analysis," T. SICE, 49(10): 975-981 (2013).

European Patent Office, Communication Pursuant to Article 94(3) EPC in European Patent Application No. 15786597.3 (dated Apr. 14, 2020).

Goto, "Control of Muscle Tonus," J. Kansai Phys. Ther., 3: 21-31 (2003).

Hackney, Doping, Performance-Enhancing Drugs, and Hormones in Sport: Mechanisms of Action and Methods of Detection, Chapter 6, pp. 65-76 (2018).

Pugh et al. (editor), "Norepinephrine," Stedman Medical Dictionary, p. 1227 (2000).

Schwarz et al., "Noradrenaline triggers muscle tone by amplifying glutamate-driven excitation of somatic motoneurones in anaesthetized rats," J. Physiol., 586(23): 5787-5802 (2008).

* cited by examiner

Figure 1. Visit Difference Scores of Finger Tap Test
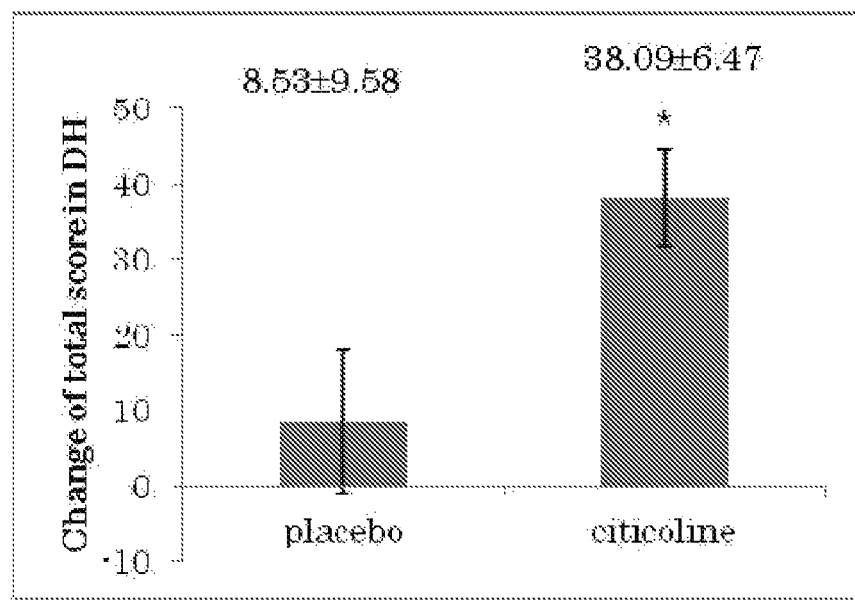
*$P<0.05$ significantly different from the placebo.
Figure 2. Visit Difference Scores of Ruff2&7 speed task
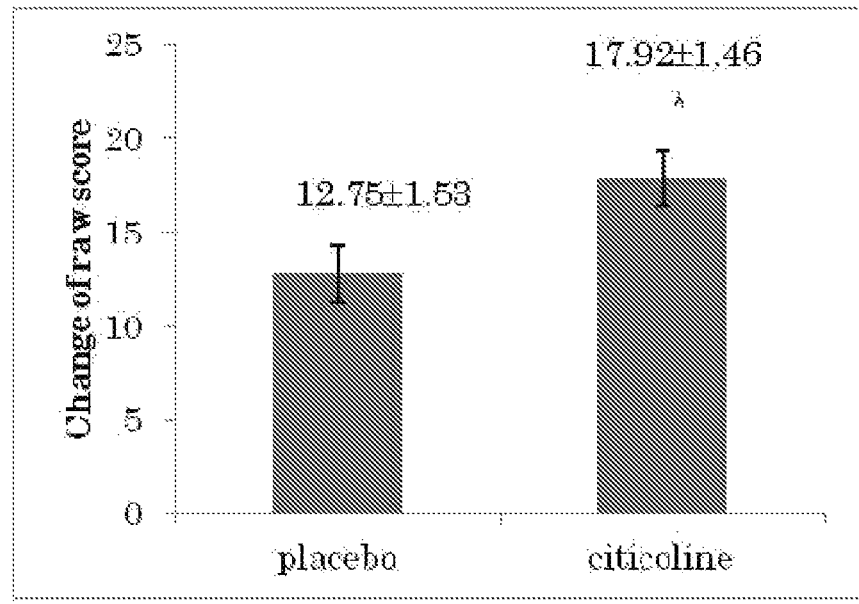
*$P<0.05$ significantly different from the placebo.

Figure 3. General Questionnaire Statistics for 250 mg/day group Paired Samples Statistics

| Example | Never | | | | | | | | | | Always yawning |
|---|---|---|---|---|---|---|---|---|---|---|---|
| I yawn often. | | 1 | 2 | 3 | 4 | ⑤ | 6 | 7 | 8 | 9 | 10 |

Please circle like this based on your answer.

| | Questions | | | | | | | | | | | |
|---|---|---|---|---|---|---|---|---|---|---|---|---|
| 1 | My eyes often feel strained. | Never | 1 | 2 | 3 | 4 | 5 | 6 | 7 | 8 | 9 | Constant eyestrain 10 |
| 2 | I find it hard to focus on distant objects. | Never | 1 | 2 | 3 | 4 | 5 | 6 | 7 | 8 | 9 | Always have difficulty focusing 10 |
| 3 | I find it hard to focus on nearby objects. | Never | 1 | 2 | 3 | 4 | 5 | 6 | 7 | 8 | 9 | Always have difficulty focusing 10 |
| 4 | I feel heavy-headed. | Never | 1 | 2 | 3 | 4 | 5 | 6 | 7 | 8 | 9 | Always drowsy 10 |
| 5 | My whole body feels tired. | Never | 1 | 2 | 3 | 4 | 5 | 6 | 7 | 8 | 9 | Whole body always tired 10 |
| 6 | My legs feel tired or ache. | Never | 1 | 2 | 3 | 4 | 5 | 6 | 7 | 8 | 9 | Legs severely tired and achy 10 |
| 7 | I yawn often. | Never | 1 | 2 | 3 | 4 | 5 | 6 | 7 | 8 | 9 | Always yawning 10 |
| 8 | I often feel disoriented or muddled. | Never | 1 | 2 | 3 | 4 | 5 | 6 | 7 | 8 | 9 | Always foggy-brained 10 |
| 9 | I become drowsy during the daytime. | Never | 1 | 2 | 3 | 4 | 5 | 6 | 7 | 8 | 9 | Always drowsy 10 |
| 10 | I have headaches. | Never | 1 | 2 | 3 | 4 | 5 | 6 | 7 | 8 | 9 | Always headachey 10 |
| 11 | I feel anxious or troubled. | Never | 1 | 2 | 3 | 4 | 5 | 6 | 7 | 8 | 9 | Feel strong anxiety 10 |
| 12 | I have a hard time organizing my thoughts. | Never | 1 | 2 | 3 | 4 | 5 | 6 | 7 | 8 | 9 | Difficulty organizing thoughts 10 |
| 13 | I get confused/mixed up when I am talking. | Never confused in conversation 1 | 2 | 3 | 4 | 5 | 6 | 7 | 8 | 9 | | Always confused in conversation 10 |
| 14 | I get irritated easily. | Never irritated 1 | 2 | 3 | 4 | 5 | 6 | 7 | 8 | 9 | | Always irritated 10 |
| 15 | I find it hard to remember details. | Never | 1 | 2 | 3 | 4 | 5 | 6 | 7 | 8 | 9 | Always 10 |
| 16 | I make careless mistakes at work, at home, or in other activities. | Never make mistakes 1 | 2 | 3 | 4 | 5 | 6 | 7 | 8 | 9 | | Consistently make mistakes 10 |

Test Code ( )      ID NO. ( )
Date ( )
Time ( )
Study Day No. ( )

General Questionnaire (Pre)

For the listed questions, please circle the number that best correspondeds to your answer.
"1" or "10" is the maximum(strongest) or minimum(weakest) feeling you can imagine.
Please follow the example provided below.

Figure 3 (Continued)

| Test Code ( ) | | General Questionnaire Page 2 Study Day No. ( ) | ID NO. ( ) Date ( ) Time( ) |
|---|---|---|---|
| 18 | I have difficulty keeping my attention on tasks or recreational activities. | No trouble focusing  1  2  3  4  5  6  7  8  9 | Difficulty concentrating 10 |
| 19 | I am told that I do not seem to listen when spoken to directly. | Never  1  2  3  4  5  6  7  8  9 | Always 10 |
| 18 | I follow through on instructions to finish chores, or duties in the workplace? | Never  1  2  3  4  5  6  7  8  9 | Always 10 |
| 20 | I have difficulty organizing tasks and activities. | Never  1  2  3  4  5  6  7  8  9 | Always 10 |
| 21 | I avoid or dislike tasks that require sustained mental effort (such as problem solving). | Never  1  2  3  4  5  6  7  8  9 | Always 10 |
| 22 | I lose things necessary for carrying out tasks or activities (such as calculators, tools, etc). | Never  1  2  3  4  5  6  7  8  9 | Always 10 |
| 23 | I am easily distracted by extraneous stimuli. | Never distracted  1  2  3  4  5  6  7  8  9 | Easily distracted 10 |
| 24 | I am forgetful in daily activities. | Never  1  2  3  4  5  6  7  8  9 | Always 10 |
| 25 | I fall asleep easily. | Fall asleep easily  1  2  3  4  5  6  7 | Difficulty falling asleep or can't sleep at all 8  9  10 |
| 26 | I wake in the middle of the night. | Never  1  2  3  4  5  6  7 | Often wakes in the middle of the night 8  9  10 |
| 27 | I wake before I have to, and have difficulty falling back asleep. | Never  1  2  3  4  5  6  7 | Wake much earlier than desired 8  9  10 |
| 28 | How do you feel about the total amount of sleep you got? | Sufficient  1  2  3  4  5  6  7 | Not enough at all, or cannot sleep at all 8  9  10 |
| 29 | How do you feel about your overall quality of sleep? (Unrelated to amount of sleep) | Satisfied  1  2  3  4  5  6  7 | Not satisfied at all 8  9  10 |
| 30 | How do you feel during the day? | Content  1  2  3  4  5  6  7  8  9 | Severely depressed 10 |
| 31 | How is your social activity in the day time (physical and mental)? | Very active  1  2  3  4  5  6  7  8  9 | Severely impaired 10 |
| 32 | I feel sleepy during the daytime. | Never  1  2  3  4  5  6  7  8  9 | Always feel severe sleepiness 10 |
| 33 | How do you feel about your complexion of your face? | Has a good complexion  1  2  3  4  5  6  7  8  9 | Pale 10 |
| 34 | The skin on my cheek and jaw feels rough. | No, and not concerned  1  2  3  4  5  6  7  8  9 | Yes, and very concerned 10 |

Please comment freely about your general physical and mental condition, as well as your feelings about these areas (e.g. vision, memory, fatigue, concentration, sleep, headaches, etc).

Thank you for your cooperation.

Figure 4

ADMINISTRATION OF CITICOLINE TO IMPROVE COGNITIVE PERFORMANCE, ATTENTIONAL PERFORMANCE, AND MOTOR FUNCTION

CROSS-REFERENCE TO RELATED APPLICATIONS

The present application claims priority to U.S. Provisional Patent Application Ser. No. 61/986,502, the contents of which are hereby incorporated by reference.

BACKGROUND OF THE INVENTION

Cytidine 5'-diphosphocholine, also known as citicoline, is a choline-containing compound made up of choline and cytidine, and is a nucleotide that is integral to cellular metabolism. A recognized precursor to acetylcholine, citicoline promotes the synthesis and transmission of neurotransmitters important to memory and attention. As a supplement, citicoline has been used in Japan, Europe, and the United States to ameliorate cognitive impairment and memory dysfunction in populations not generally considered in good health, such as the elderly, Alzheimer's patients, stroke victims, and victims of traumatic brain injury. There remains a need for a supplement that prevents the decline of cognitive function and motor function in healthy adults.

BRIEF SUMMARY OF THE INVENTION

The present invention addresses the aforementioned need. The present invention provides an agent, citicoline, and a method of mitigating cognitive decline or improving cognitive function and mitigating decline motor function or improving motor function by administering citicoline to a subject in need, increasing the utilization of cellular energy reserves and increasing phospholipid membrane production needed for cellular repair.

In one embodiment of the present invention, a method for improving motor function of a healthy human subject comprising a step of administering an effective amount of cytidine 5'-diphosphocholine (hereinafter referred to as citicoline) or a salt thereof to a healthy human subject is provided.

In another embodiment of the present invention, the effective amount of citicoline or a salt thereof being administered is an amount that is 5 mg or more and 4.0 g or less per day.

In another embodiment of the present invention, the effective amount of citicoline or a salt thereof being administered is an amount that is 100 mg or more and 1.0 g or less per day.

In another embodiment of the present invention, the effective amount of citicoline or a salt thereof being administered is an amount that is 250 mg or more and 500 mg or less per day.

In another embodiment of the present invention, the effective amount of citicoline or a salt thereof being administered is an amount that is less than 500 mg per day.

In yet another embodiment of the present invention, the citicoline or a salt thereof is administered orally.

In another embodiment of the present invention, the citicoline or a salt thereof is administered alone in an amount that is 5 mg or more and 4.0 g or less per day.

In one embodiment of the present invention, the citicoline or a salt thereof is administered for at least 1 day and at most 1 year.

In another embodiment, citicoline or a salt thereof is administered for at least 1 day and at most 4 weeks.

BRIEF DESCRIPTION OF THE DRAWINGS

FIG. 1 shows the effects of citicoline administration on motor speed and control compared to a control group receiving placebos. The citicoline-treated group (N=51) were administered 250 mg/day (N=24) or 500 mg/day (N=27). Three finger tap tests were administered over a period of 28 days to measure motor speed and control. Results are expressed as mean±SD. Statistical analysis was performed using Student's t test. The p<0.05 was considered statistically significant.

FIG. 2 shows the effects of citicoline administration on attentional capacity compared to a control group receiving placebos.

FIG. 3 shows the General Questionnaire.

FIG. 4 shows the Exercise and Life Style Questionnaire.

DETAILED DESCRIPTION OF THE INVENTION

A detailed description of the various tests and studies conducted and the results of each of these studies are listed. The studies conducted involve healthy subject groups generally administered with either high dose of citicoline (500 mg/day) or low dose of citicoline (250 mg/day).

Example

Materials and Methods

Study participants were screened by telephone prior to study enrollment. Healthy subjects, ages 13-18, with no significant medical conditions and no history of co-morbid psychiatric disorder, current Axis I or II diagnosis, or previous participation in a pharmacotherapeutic trial, were selected. Use of any psychotropic medication or any previous head injury resulting in loss of consciousness for 5 or more minutes were used as exclusion criteria. While no participant met criteria for a neuropsychiatric disorder at enrollment, clinical assessments were still completed throughout the study to evaluate changes in mood state. In addition, self-reports of sleep habits, lifestyle, and exercise routines were also administered at baseline as well as at each study visit to assess changes in health habits during study participation.

Participants also provided a urine sample for drug screening and a blood sample for comprehensive chemistry panel (sodium, potassium, chloride, BUN, creatinine, glucose, calcium, magnesium, phosphorus), liver function tests (SGOT, SGPT, GGT, total bilirubin, albumin), a full blood count (WBC, RBC, platelet count).

A visual acuity test was given in addition to weight and height measurements. Participants then completed a diagnostic interview, lifestyle questionnaires, and neuropsychological testing.

Following the completion of Visit 1 assessment, participants were given their 28-day supply of citicoline (250 mg or 500 mg) or placebo, which was randomly assigned. They were instructed to take one capsule a day every day for the next 28 days.

Visit 2 occurred fourteen days after Visit 1. At Visit 2, the remaining study pills were counted and participant dosage calendars were checked to ensure compliance with the protocol. Additional neuropsychological measures and clinical assessments were administered during this visit.

Participants returned for Visit 3 fourteen days later, on the 28th day of their study participation. The pill bottle and the dosage calendar were collected from each participant. Urine and blood were again obtained. Participants also participated in similar clinical and neuropsychological testing and clinical measures that were given during visit 1.

Clinical Ratings and Assessment

Schedule for Affective Disorders and Schizophrenia for School-Age Children/Present and Lifetime Version (KSADS-PL)

The KSADS-PL was administered to each participant during the first visit. The KSADS-PL is a structured diagnostic interview used to assess current functioning and to determine whether participants met study inclusion criteria, including absence of a lifetime Axis I or Axis II psychiatric disorder both currently and lifetime. None of the 75 participants who completed the study met criteria for any past or current Axis I or II disorder.

Columbia-Suicide Severity Rating Scale (C-SSRS)

The C-SSRS is an investigator-administered scale that assesses suicidal ideation and identifies behaviors that may indicate intent to commit suicide. The C-SSRS was administered at each of the three visit to assess for presence or absence of suicidal ideation.

The Positive and Negative Affect Scale for Children (PANAS-C)

The PANAS-C is a self-report questionnaire on which participants rate to what extent they are currently experiencing a variety of positive and negative emotions such as "excited" and "mad." The PANAS was administered during each of the three visits to assess participant affect prior to taking the study drug as well as after taking the study drug over a period of 28 days.

Children's Depression Rating Scale (CDRS)

The CDRS is an investigator-administered scale that are widely used as observational measures of depressive symptoms in children. The scale was administered at each of the three visits to assess presence or absence of depressive symptoms.

Barratt Impulsiveness Scale (BIS)

The BIS is a questionnaire is a scale used to measure impulsiveness. It includes three subscales: attentional, motor, and non-planning impulsiveness. A total score, or a sum of the three factors, was also calculated. The scale was administered at the first and third visits to assess presence or absence of symptoms of impulsiveness.

ADHD Rating Scale (ARS)

The ARS is a questionnaire assessing the frequency of DSM-IV-TR symptoms of ADHD in children including inattention, impulsivity, and hyperactivity. The scale was administered at each of the three visits to assess presence or absence of ADHD symptoms.

Conner-Wells Self-Report Scale (L) (Conners)

The Conners is a self-report questionnaire assessing a range or problem behaviors in children, including family problems, emotional problems, conduct problems, cognitive problems/inattention, anger control problems, hyperactivity, ADHD Index, and DSM-IV symptom subscales. The scale was administered at the first and third visits to assess presence or absence of a range of problem behaviors.

Pittsburgh Sleep Quality Index (PSQI)

The PSQI is a self-report sleep questionnaire designed to assess usual sleep habits during the past month. The PSQI was administered at each of the three study visits to assess alterations to sleep quality during the 28 days of study participation.

General Questionnaire, Exercise and Life Style Questionnaire

The General Questionnaire and Exercise and Life Style Questionnaire are self-report questionnaires designed to assess a variety of symptoms, behaviors, and self-perceptions, including mood, complexion, exercise, food, and alcohol habits of each of the participants. The General Questionnaire was administered during each of the three study visits; the Exercise and Life Style Questionnaire was administered during each of the three study visits.

Neuropsychological Measures

Wechsler Adult Intelligence Scale-Revised (WASI-R)

Two subtests were included from the WASI-R test to generate estimates of Verbal Comprehension and Perceptual Reasoning. The vocabulary subtests were completed to estimate verbal abilities, which has also been supported as a strong predictor of overall intellectual ability. The Matrix Reasoning subtest was also administered as an estimate of perceptual reasoning. The two WASI-R subtests were administered during the first visit.

WAIS-IV Vocabulary Subtest:

This subtest measures the participants' verbal ability and has been shown to correlate with measures of general intellectual ability.

WAIS-IV Matrix Reasoning Subtest:

The Matrix Reasoning subtest primarily measures non-verbal abstract problem solving. It also assesses inductive and spatial reasoning abilities.

Motor Function

Finger Tap Test

The finger tap test is used to measure motor speed and control. It is a common assessment measure administered by neuropsychologists to detect cognitive impairment. During the finger tap test, the participant is instructed to use his/her index finger to press a lever attached to a mechanical counter as many times as s/he can within the designated time period. The participant is instructed to move only their index finger, not the entire hand. The same process is completed using the index finger of the dominant and non-dominant hand. The finger tap test was administered at each of the three visits.

Assessment of Cognitive Domains

Memory

California Verbal Learning Test I (CVLT-I) and California Verbal Learning Test II (CVLT-II)

These verbal learning tests assess the subject's immediate and delayed recall, as well as suggesting the strategy utilized for retrieval of newly-learned information. Subjects are asked to remember a 16-item word list, which is presented on five trials. After each trial, the subject is asked to recall all of the words that they can remember. A second list is then presented to provide an interference condition. The subject is then asked to recall the first word list. After a temporal delay, the subject is again asked to recall the first word list. Test results provide scores for assessing verbal learning, strength of memory following interfering tasks, proactive interference, accuracy of recognition memory and storage versus retrieval of newly learned information. The CVLT was administered at all three visits.

Rey-Osterreith Complex Figure Test (ROCFT) and Modified Taylor Complex Figure (MTCF)

The ROCFT is an assessment of visuo-organizational ability, visual attention, and visual memory. The participant is asked to copy a complex 2-dimensional figure with the stimulus or complex figure in front of them (Copy Trial), immediately after the stimulus has been removed (Short Delay Trial), and after 30 minutes without the stimulus present (Long Delay Trial). The figure produced at each trial is then evaluated for the strategy used in reproducing the figure, constructional accuracy, and placement of elements within the figure. The Copy, Short Delay, and Long Delay trials are each scored on the number of elements that have been correctly recalled and the accuracy and placement of each element. The Difference Score between immediate and delayed performance scores is a measure of temporary decay for visuospatial memory. This test was administered on both the first and the third visits. The Modified Taylor Complex Figure (MTCF) is an alternate form of the ROCFT to assess visuo-organizational ability, visual attention, and visual memory. The same procedure was used to administer the MTCF. The MTCF was administered at the second visit instead of the ROCFT to minimize the effect of repeat testing on copy and retention of the figure across visits.

Attention

Stroop Color Word Test

The Stroop measures the ability to inhibit incorrect responses and to resist interference. The three conditions, Color Naming, Word Reading, and Interference, are designed to establish competing response tendencies. Outcome variables include time to complete each condition, as well as total errors per condition. The Stroop test was administered at each of the three visits.

Continuous Performance Test (CPT)

The CPT is a test of sustained attention that has been adapted for computerized administration. The test requires participants to attend vigilantly to a series of target and distracter stimuli for a 14-minute duration. Attention scores include reaction time, omission errors during which the participant should have responded but did not, and commission errors during which the participant failed to inhibit a response. The CPT was administered at all three visits.

Ruff 2 & 7

The Ruff 2 & 7 measures two aspects of visual attention: sustained attention and selective attention. There are a series of 20 trials involving visual searching in which the respondent detects and marks through all given stimuli the digits "2" and "7". In the 10 Automatic Detection trials, the target digits are embedded among alphabetical letters that serve as distractors. In the 10 Controlled Search trials, the target digits are embedded among other numbers that serve as distractors. Correct hits and errors are counted for each trial and serve as the basis for scoring the test. Accuracy scores evaluate the number of targets identified in relation to the number of possible targets. The Ruff 2 & 7 was administered at all three visits.

Mental Flexibility

Wisconsin Card Sorting Task (WCST)

The WCST assess a person's ability to form abstract concepts, utilize feedback, and to shift and maintain set. This test has been shown to be sensitive to frontal lobe dysfunction. The WCST involves 4 stimulus cards that vary in color, geometric form, and number. Without knowing the criterion, participants are asked to match cards from a deck to the stimulus cards. After the participant places each card, she is told whether she is correct or incorrect and should change the element she is matching based on this feedback. Dependent variables include total number of cards used, categories achieved (color, form, or number), and perseverative errors during which the individual did not adjust matching strategy according to feedback. The WCST was given on the third visit of the study.

Trail Making Test

The Trail Making Test is designed to measure visual conceptual and visuomotor tracking, as well as maintenance of cognitive set. On Trial A the participant must draw lines to connect consecutively numbered circles on one work sheet (1-2-3-4 etc.). For Part B she must connect numbered and lettered circles by alternating between the two sequences (i.e., 1-A-2-B etc.). Part B is the more sensitive of the two tests—particularly to frontal-lobe dysfunction—as scores on this section are indicative of the participant's ability to shift sets (numeric to alphabetical order) and process concurrent stimuli. This test was administered on all three visits.

Measurement of Adverse Events

Monitoring of Side Effects Scale (MOSES)

The MOSES is a scale designed to assess common symptoms or adverse events associated with psychopharmacological medications. This scale is divided into nine body areas representing a typical physical examination. The interviewer asks subjects whether they have each symptom on the measure and, if so, asks them to report the level of severity of the symptom on a scale from 0 (not present) to 4 (severe). This scale was administered on the second and third visits to assess presence or absence of adverse events.

Results and Discussion

The Positive and Negative Affect Scale (PANAS-C)

Comparisons within Groups for Difference Scores

On the PANAS-C, the 250 mg/day group showed significant declines in feeling positive emotions ($p<0.01$) and showed improvement in feeling less negative emotions ($p<0.01$) between visit 1 and visit 3 (Table 3).

The Placebo group showed a trend toward declines in positive emotion (p=0.09) and showed improvement in feeling less negative emotions (p=0.03) between visit 1 and visit 3 (Table 4).

On the PANAS-C, the 500 mg/day group showed significant declines in feeling positive emotions (p=0.04) and showed improvement in feeling less negative emotions (p<0.01) between visit 1 and visit 3 (Table 5).

Comparisons Between Groups at Time 3

At visit 3, no significant differences were evident between the 250 mg/day group and the 500 mg/day group on both positive emotional attributes (p=0.95) or negative emotional attributes (p=0.18) (Table 5).

No significant effect was seen between the Placebo group and the 500 mg/day group during visit 3 for positive emotional attributes (p=0.39). The 500 mg/day group showed less negative emotional attributes compared to the 500 mg/day group (p=0.03) (Table 6).

At visit 3, no significant effects were seen between the 250 mg/day group and the Placebo group in positive emotional attributes (p=0.44) and negative emotional attributes (p=0.45) (Table 6a).

When the 250 mg/day, Placebo, and the 500 mg/day groups were included in an overall analysis, there was a trend toward significant differences between groups on negative emotional attributes (p=0.06). Post-hoc analyses showed that at visit 3 individuals in the 500 mg/day group showed a trend toward feeling less negative emotions compared to individuals in the Placebo group (p=0.05) (Table 7).

Comparisons Between Groups for Difference Scores

On the PANAS-C, there were no significant differences between the 250 mg/day group and the 500 mg/day group from visit 1 to visit 3 on positive emotional attributes (p=0.18) or negative emotional attributes (p=0.89) (Table 5).

There were no significant differences between the Placebo group and the 500 mg/day group from visit 1 to visit 3 on positive emotional attributes (p=0.97) or negative emotional attributes (p=0.41) (Table 6).

There were no significant differences between the 250 mg/day group and the Placebo group from visit 1 to visit 3 on positive emotional attributes (p=0.23) or negative emotional attributes (p=0.43) (Table 6a).

No overall between group differences were detected for positive emotional attribute differences (p=0.15) or negative emotional attribute differences (p=0.32) between visit 1 and visit 3 (Table 8).

Children's Depression Rating Scale (CDRS)

Comparisons within Groups for Difference Scores

On the CDRS, the 250 mg/day group showed significant declines in depressive symptoms (p=0.02) between visit 1 and 3 (Table 9).

There were no significant differences for the Placebo group between visit 1 and 3 on the CDRS (p=0.42) (Table 10).

On the CDRS, the 500 mg/day group showed significant declines in depressive symptoms (p=0.03) between visit 1 and 3 (Table 11).

Comparisons Between Groups at Time 3

At visit 3, no significant difference was evident between the 250 mg/day and the 500 mg/day group on the CDRS (p=0.29) (Table 12). No significant difference was detected between the Placebo group and the 500 mg/day group during visit 3 on CDRS (p=0.30) (Table 13).

At visit 3, no significant difference was evident between the 250 mg/day and the Placebo group on the CDRS (p=0.93) (Table 13a).

When the 250 mg/day, Placebo, and the 500 mg/day groups were included in an overall analysis, no significant differences between groups were detected on the CDRS (p=0.27) (Table 14).

Comparisons Between Groups for Difference Scores

On the CDRS, there were no significant differences between the 250 mg/day group and the 500 mg/day group from visit 1 to visit 3 on depressive symptoms (p=0.22) (Table 12). There were no significant differences between the Placebo group and the 500 mg/day group from visit 1 to visit 3 on depressive symptoms (p=0.40) (Table 13).

On the CDRS, there were no significant differences between the 250 mg/day group and the Placebo group from visit 1 to visit 3 on depressive symptoms (p=0.10) (Table 13a).

There was a trend toward significant differences between group difference scores (p=0.07). Post-hoc analyses showed that at individuals in the 250 mg/day group showed a trend toward greater declines in depressive symptoms compared to individuals in the Placebo group (p=0.07) (Table 15).

Barratt Impulsiveness Scale (BIS)

The BIS included three summary categories of attention, motor, and non-planning impulsiveness, each of which had multiple individual items. Within and between group analyses are reported below for the three summary categories, as well as the total score.

Comparisons within Groups for Difference Scores

The 250 mg/day group showed no improvement between visit 1 and visit 3 on attention (p=0.44), motor (p=0.36), non-planning (p=0.30), or the total score (p=0.35) (Table 16).

The Placebo group showed no improvement between visit 1 and visit 3 on attention (p=0.45), motor (p=0.40), or the total score (p=0.33). There was a trend toward improvement in scores on non-planning from visit 1 to 3 (p=0.09) (Table 17). The Placebo group showed no improvement between visit 1 and visit 3 on attention (p=0.47), motor (p=0.40), or the total score (p=0.17). There was a trend toward improvement in scores on non-planning from visit 1 to 3 (p=0.09) (Table 18).

Comparisons Between Groups at Time 3

At visit 3, the 500 mg/day group showed a significantly lower total score than the 250 mg/day group (p=0.03). There was a trend toward significant differences in the 250 mg/day and 500 mg/day group on attention (p=0.07) and motor (p=0.05), with the 500 mg/day group showing a lower score compared to the 250 mg/day group on both scores. There were no significant differences in the non-planning score between the 250 mg/day and 500 mg/day group (p=0.12) (Table 19).

At visit 3, no significant difference was detected between the Placebo group and the 500 mg/day group on attention (p=0.82), motor (p=0.47), non-planning (p=0.56), or the total score (p=0.91) (Table 20).

At visit 3, the Placebo group showed a significantly lower total score (p=0.02) and non-planning score (p=0.04) than the 250 mg/day group. There was a trend toward significant differences in the 250 mg/day and Placebo group on attention (p=0.08), with the Placebo group showing a lower score compared to the 250 mg/day group. There were no significant differences in the motor score between the 250 mg/day and Placebo group (p=0.13)(Table 20a).

When the 250 mg/day, Placebo, and the 500 mg/day groups were included in an overall analysis, there were significant differences between groups on attention (p=0.05), motor (p=0.04), non-planning (p=0.04), and the total score (p=0.01). Post-hoc analyses showed that at visit 3 individuals in the 500 mg/day group showed a trend toward lower scores on attention compared to individuals in the 250 mg/day group (p=0.06). The 500 mg/day group showed a significantly lower motor score (p=0.04) and the total score (p=0.02) than the 250 mg/day group at visit 3. The Placebo group showed a significantly lower non-planning score (p=0.04) and total score (p=0.03) than the 250 mg/day group at visit 3 (Table 21).

Comparisons Between Groups for Difference Scores

No significant differences were detected between the 250 mg/day group and the 500 mg/day group on differences in scores from visit 1 to visit 3 for attention (p=0.88), motor (p=0.44), non-planning (p=0.98), or the total score (p=0.67) (Table 19).

No significant differences were detected between the Placebo group and the 500 mg/day group on differences in scores from visit 1 to visit 3 for attention (p=0.89), motor (p=0.42), non-planning (p=0.58), or the total score (p=0.85) (Table 20).

No significant differences were detected between the 250 mg/day group and the Placebo group on differences in scores from visit 1 to visit 3 for attention (p=0.99), motor (p=0.95), non-planning (p=0.60), or the total score (p=0.81) (Table 20a).

When the 250 mg/day, Placebo, and the 500 mg/day groups were included in an overall analysis, no significant differences between groups were detected on attention (p=0.49), motor (p=0.32), non-planning (p=0.42), and the total score (p=0.45) (Table 22).

ADHD Rating Scale (ARS)

The ARS included two summary categories of inattention and impulsivity, each of which had multiple individual items. Within and between group analyses are reported below for the two summary categories.

Comparisons within Groups for Difference Scores

The 250 mg/day group showed no improvement between visit 1 and visit 3 on inattention (p=0.17). There were significant declines in impulsivity between visit 1 and visit 3 for the 250 mg/day group (p<0.01) (Table 23).

The Placebo group showed significant declines in inattention between visit 1 and visit 3 (p=0.03). There were no improvements between visit 1 and 3 for impulsivity for the Placebo group (p=0.10) (Table 24).

The 500 mg/day group showed no improvement between visit 1 and visit 3 on inattention (p=0.28). There were significant declines in impulsivity between visit 1 and visit 3 for the 250 mg/day group (p=0.02) (Table 25).

Comparisons Between Groups at Time 3

The 500 mg/day group showed significantly lower scores on inattention at visit 3 compared to the 250 mg/day group (p=0.01). There were no significant differences detected between the 250 mg/day group and the 500 mg/day group on impulsivity (p=0.13) (Table 26).

At visit 3, no significant difference was detected between the Placebo group and the 500 mg/day group on inattention (p=0.46) or impulsivity (p=0.48) (Table 27).

The Placebo group showed significantly lower scores on inattention at visit 3 compared to the 250 mg/day group (p<0.01). There were no significant differences detected between the 250 mg/day group and the Placebo group on impulsivity (p=0.56) (Table 27a).

When the 250 mg/day, Placebo, and the 500 mg/day groups were included in an overall analysis, there were significant differences at visit 3 on inattention (p<0.01). Post-hoc analyses showed that the 500 mg/day group (p<0.01) and the Placebo group (p<0.01) showed significantly lower scores on inattention than the 250 mg/day group. No significant differences between groups were detected on impulsivity at visit 3 (p=0.20) (Table 28).

Comparisons Between Groups for Difference Scores

No significant differences were detected between the 250 mg/day group and the 500 mg/day group on differences in scores from visit 1 to visit 3 for inattention (p=0.27) or impulsivity (p=0.77) (Table 26).

No significant differences were detected between the Placebo group and the 500 mg/day group on differences in scores from visit 1 to visit 3 for inattention (p=0.61) or impulsivity (p=0.39) (Table 27).

No significant differences were detected between the 250 mg/day group and the Placebo group on differences in scores from visit 1 to visit 3 for inattention (p=0.10) or impulsivity (p=0.26) (Table 27a).

When the 250 mg/day, Placebo, and the 500 mg/day groups were included in an overall analysis, no significant differences between groups were detected for inattention (p=0.11) or impulsivity (p=0.25) (Table 29).

Conner-Wells Self-Report Scale (L) (Conners)

Comparisons within Groups for Difference Scores

On the Conners, the 250 mg/day group showed significant increases between visit 1 and visit 3 in problem behaviors, with visit 3 having higher scores than visit 1 (p=0.02) (Table 30).

The Placebo group showed a trend toward a significant declines in problem behaviors between visit 1 and visit 3 (p=0.07) (Table 31).

The 500 mg/day group showed significant declines in problem behaviors between visit 1 and visit 3 (p<0.01) (Table 32).

Comparisons Between Groups at Time 3

At visit 3, the 500 mg/day group showed significantly lower scores on problem behaviors than the 250 mg/day group (p=0.01) (Table 33).

No significant difference was detected between the Placebo group and the 500 mg/day group during visit 3 on the Conners in problem behaviors (p=0.28) (Table 34).

At visit 3, no significant difference was detected between the 250 mg/day group and the Placebo group on the Conners in problem behaviors (p=0.10) (Table 34a).

When the 250 mg/day, Placebo, and the 500 mg/day groups were included in an overall analysis, there were significant differences between groups on problem behaviors on the Conners (p=0.01). Post-hoc analyses showed that the 500 mg/day group had significantly lower scores on problem behaviors than the 250 mg/day group (p=0.01). There was also a trend toward the Placebo group having lower scores on problem behaviors at visit 3 compared to the 250 mg/day group (p=0.09) (Table 35).

Comparisons Between Groups for Difference Scores

There were no significant differences between visit 1 and visit 3 in problem behaviors when the 250 mg/day and 500 mg/day group were compared (p=0.36) (Table 33).

There were no significant differences between visit 1 and visit 3 in problem behaviors when the Placebo and 500 mg/day group were compared (p=0.17) (Table 34).

There were no significant differences between visit 1 and visit 3 in problem behaviors when the 250 mg/day and Placebo group were compared (p=0.66) (Table 34a).

On the Conners, when the visit 1 to visit 3 difference scores for the 250 mg/day, Placebo and 500 mg/day groups were compared, there was no significant difference detected between groups in problem behaviors (p=0.20) (Table 36).

Pittsburgh Sleep Quality Index (PSQI)

Comparisons within Groups for Difference Scores

On the PSQI, the 250 mg/day group showed a significant difference in sleep quality between visit 1 and visit 3 (p<0.01) (Table 37).

The Placebo group showed a significant difference in sleep quality between visit 1 and visit 3 (p<0.01) (Table 38).

On the PSQI, the 500 mg/day group showed a significant difference in sleep quality Between visit 1 and visit 3 (p<0.01) (Table 39).

Comparisons Between Groups at Time 3

At visit 3, no significant difference was evident between the 250 mg/day and the 500 mg/day group on the PSQI in sleep quality (p=0.77) (Table 40).

No significant difference was detected between the Placebo group and the 500 mg/day group during visit 3 on the PSQI in sleep quality (p=0.83) (Table 40).

No significant difference was detected between the 250 mg/day group and the Placebo group during visit 3 on the PSQI in sleep quality (p=0.60) (Table 41a).

When the 250 mg/day, Placebo, and the 500 mg/day groups were included in an overall analysis, no significant differences between groups were detected in sleep quality on the PSQI (p=0.44) (Table 42).

Comparisons Between Groups for Difference Scores

The 250 mg/day group did not demonstrate a significant difference in sleep quality on the PSQI than the 500 mg/day group between visit 1 and visit 3 (p=0.82) (Table 40).

On the PSQI, there was no significant difference between the Placebo group and the 500 mg/day group from visit 1 to visit 3 in sleep quality (p=0.92) (Table 41).

The 250 mg/day group did not demonstrate a significant difference in sleep quality on the PSQI than the Placebo group between visit 1 and visit 3 (p=0.72) (Table 41a).

On the PSQI, when the visit 1 to visit 3 difference scores for the 250 mg/day, Placebo and 500 mg/day groups were compared, there was no significant difference detected between groups in sleep quality (p=0.47) (Table 43).

General Questionnaire

The General Questionnaire included five summary categories (Vision, Depression, Attention, Sleep, and Complexion) each of which had multiple individual items. See FIG. 3. Within and between group analyses are reported below for each of the summary categories.

Comparisons within Groups for Difference Scores

The 250 mg/day group showed improvement between visit 1 and visit 3 on total vision (p<0.01), depression (p<0.01), attention (p=0.04), and sleep (p<0.01). The 250 mg/day group also demonstrated a trend toward improved complexion (p=0.09) (Table 44).

The Placebo group showed improvement between visit 1 and visit 3 on total vision (p<0.01), depression (p<0.01), attention (p<0.01), sleep (p<0.01), and complexion (p<0.01) (Table 45).

The 500 mg/day group showed improvement between visit 1 and visit 3 on total vision (p<0.01), depression (p<0.01), attention (p=0.01), sleep (p<0.01), and complexion (p<0.01) (Table 46).

Comparisons Between Groups at Time 3

At visit 3, the 500 mg/day group showed lower scores on depression (p=0.03) and attention (p=0.04) compared to the 250 mg/day group. No significant differences were evident between the 250 mg/day and the 500 mg/day group in vision (p=0.24), sleep (p=0.50) and complexion (p=0.12) (Table 47).

No significant differences were detected between the Placebo group and the 500 mg/day group during visit 3 for scores on vision (p=0.60), depression (p=0.28), attention (p=0.58), sleep (p=0.57), and complexion (p=0.31) (Table 48).

At visit 3, no significant differences were detected between the 250 mg/day group and the Placebo group for scores on vision (p=0.13), depression (p=0.15), attention (p=0.11), sleep (p=0.24), and complexion (p=0.49) (Table 48a).

When the 250 mg/day, Placebo, and the 500 mg/day groups were included in an overall analysis, there were significant differences between groups on depression (p=0.02) and attention (p=0.03). Post-hoc analyses showed that the 500 mg/day group showed lower scores on depression (p=0.02) and attention (p=0.04) on visit 3 compared to the 250 mg/day group. There was also a trend toward lower scores in the Placebo group on attention compared to the 250 mg/day group (p=0.09) (Table 48a).

Comparisons Between Groups for Difference Scores

Difference scores were created by subtracting individual scores at visit 1 from individual scores at visit 3. There were no significant differences between the 250 mg/day group and the 500 mg/day group on improvement from visit 1 to visit 3 for vision (p=0.38), depression (p=0.40), attention (p=0.91), sleep (p=0.17), and complexion (p=0.23) (Table 47).

There were no significant differences between the Placebo group and the 500 mg/day group on improvement from visit 1 to visit 3 for vision (p=0.51), depression (p=0.91), attention (p=0.94), sleep (p=0.79), and complexion (p=0.80) (Table 48).

There were no significant differences between the 250 mg/day group and the Placebo group on improvement from visit 1 to visit 3 for vision (p=0.84), depression (p=0.48), attention (p=0.95), sleep (p=0.24), and complexion (p=0.21) (Table 48a).

When the visit 1 to visit 3 difference scores for the 250 mg/day, Placebo and 500 mg/day groups were compared overall, there were no significant differences between groups on vision (p=0.33), depression (p=0.32), attention (p=0.50), sleep (p=0.14), and complexion (p=0.16) (Table 50).

Exercise/Lifestyle Questionnaire

Figure 4:
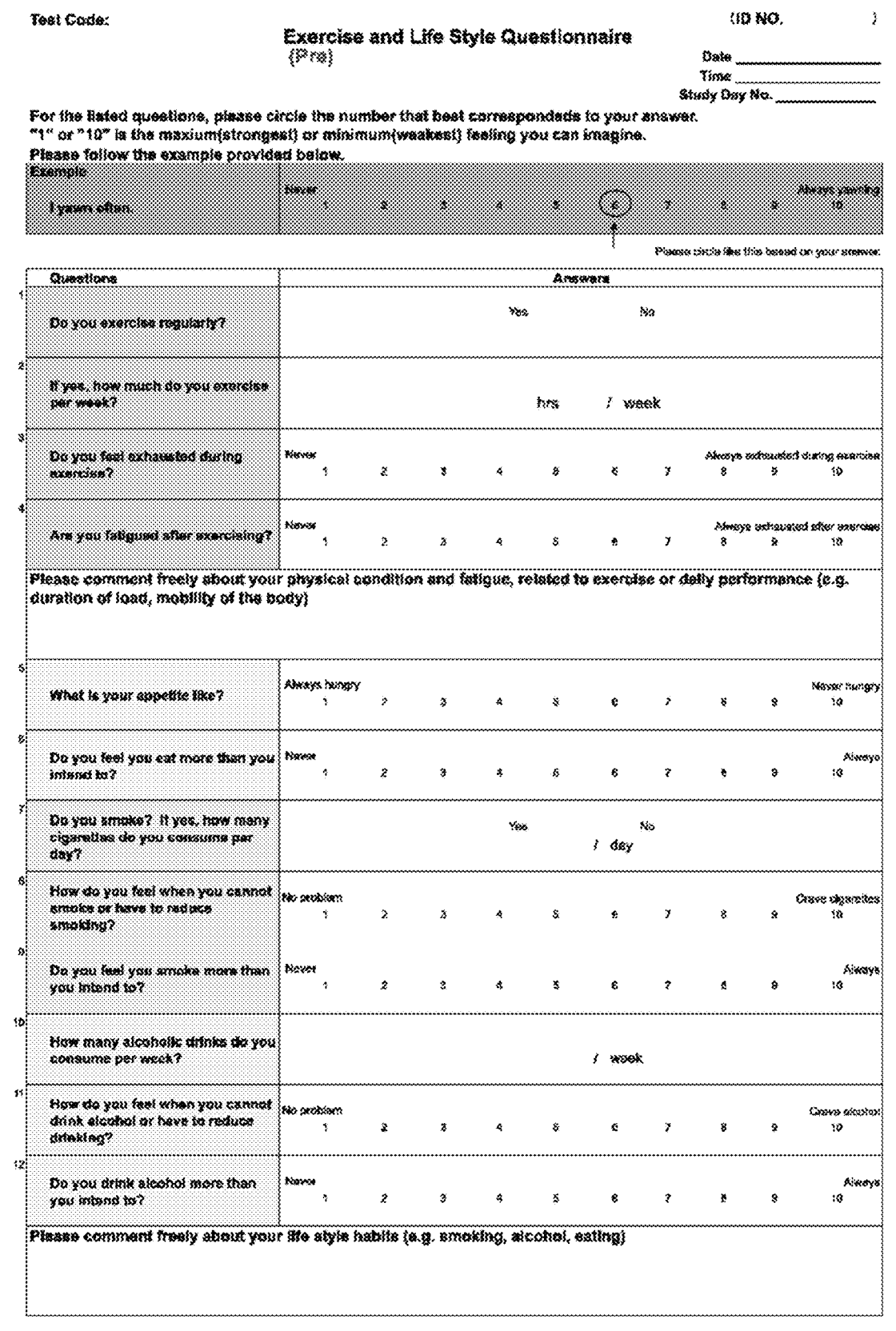

The Exercise/Lifestyle Questionnaire included four summary categories (Exercise, Appetite, Smoke, and Alcohol), each of which consisted of multiple individual items. See FIG. 4. Within and between group analyses are reported below for each of the summary categories.

Comparisons within Groups for Difference Scores

The 250 mg/day group showed a trend toward differences between visit 1 and visit 3 for appetite (p=0.08). There was no significant change in exercise (p=0.29) or smoking (p=0.16) from visit 1 to visit 3. Comparisons could not be calculated for alcohol use due to mean scores being unchanged from visit 1 to visit 3 (Table 51).

The Placebo group showed significant differences between visit 1 and visit 3 for appetite (p<0.01). There was no significant change in exercise (p=0.20) or alcohol use (p=0.16) from visit 1 to visit 3. Comparisons could not be calculated for smoking due to mean scores being unchanged from visit 1 to visit 3 (Table 52).

The 500 mg/day group showed significant differences between visit 1 and visit 3 for exercise (p<0.01). There was also a trend toward changes in appetite from visit 1 to visit 3 (p=0.09). Comparisons could not be calculated for smoking and alcohol use due to mean scores being unchanged from visit 1 to visit 3 (Table 53).

Comparisons Between Groups at Visit 3

Between group comparisons for scores at visit 3 indicated significant differences between 250 mg/day and 500 mg/day for appetite (p=0.04). There were no significant differences between the 250 mg/day group and the 500 mg/day group for exercise (p=0.83), smoking (p=0.35), or alcohol consumption (p=0.35) (Table 54).

No significant differences were found between the Placebo and the 500 mg/day group at visit 3 in exercise (p=0.47) or appetite (p=0.53). Comparisons could not be calculated for smoking and alcohol use due to mean scores being identical across groups at visit 3 (Table 55).

At visit 3, there were significant differences between the 250 mg/day and Placebo group on appetite (p<0.01). No significant differences were found between the 250 mg/day and the Placebo group at visit 3 in exercise (p=0.39), smoking (p=0.35), or alcohol use (p=0.35) (Table 55a).

When all three groups were included in an analysis of variance, there were significant differences between the 250 mg/day, Placebo, and 500 mg/day group on appetite (p=0.01). Post-hoc analyses showed that the 250 mg/day group had significantly higher scores on appetite compared to the 500 mg/day (p=0.04) and Placebo (p=0.01) groups. No significant differences were detected at visit 3 on exercise (p=0.41), smoking (p=0.21), or alcohol (p=0.21) (Table 56).

Comparisons Between Groups for Difference Scores

There were no significant differences in scores from visit 1 to visit 3 between the 250 mg/day group and 500 mg/day group on exercise (p=0.27), appetite (p=0.74), or smoking (p=0.35). Comparisons could not be calculated for alcohol use due to difference scores being unchanged from visit 1 to visit 3 (Table 54).

There were no significant differences in scores from visit 1 to visit 3 between the Placebo group and 500 mg/day group on exercise (p=0.44), appetite (p=0.34), or alcohol use (p=0.32). Comparisons could not be calculated for smoking due to difference scores being unchanged from visit 1 to visit 3 (Table 55).

There were no significant differences in scores from visit 1 to visit 3 between the 250 mg/day group and Placebo group on exercise (p=0.79), appetite (p=0.11), smoking (p=0.35), or alcohol use (p=0.29) (Table 55a).

When all three groups were included in an analysis of variance, no significant differences were detected for change between visit 1 and visit 3 on exercise (p=0.28), appetite (p=0.17), smoking (p=0.21), or alcohol (p=0.18) (Table 57).

Neuropsychological Assessments

Finger Tap Test

Comparisons within Groups for Difference Scores

The 250 mg/day group showed significant increases in scores between visit 1 and visit 3 on mean dominant hand (p<0.01) and the mean non-dominant hand (p<0.01) (Table 58). For the Placebo group, there were significant increases in scores between visit 1 and visit 3 on mean non-dominant hand (p=0.04). There were no significant differences between visit 1 and 3 for mean dominant hand (p=0.19) (Table 59).

The 500 mg/day group showed significant increases in scores between visit 1 and visit 3 on mean dominant hand (p<0.01) and the mean non-dominant hand (p<0.01) (Table 60).

Comparisons Between Groups at Time 3

At visit 3, no significant differences were found between the 250 mg/day and the 500 mg/day group on mean dominant hand (p=0.75) or mean non-dominant hand (p=0.96) (Table 61).

No significant differences were found between the Placebo and the 500 mg/day group at visit 3 on mean dominant hand (p=0.68) or mean non-dominant hand (p=0.88) (Table 62). At visit 3, no significant differences were found between the 250 mg/day and the Placebo group on mean dominant hand (p=0.88) or mean non-dominant hand (p=0.85) (Table 62a). When the 250 mg/day, Placebo, and the 500 mg/day groups were included in an overall analysis, no significant differences between groups were detected on mean dominant hand (p=0.45) or mean non-dominant hand (p=0.49) (Table 63).

Comparisons Between Groups for Difference Scores

The 250 mg/day group demonstrated a trend toward greater increases from visit 1 to visit 3 for the dominant hand compared to group 500 mg/day (p=0.08). There were no significant differences in scores for the non-dominant hand from visit 1 to 3 between the 250 mg/day and 500 mg/day groups (p=0.78) (Table 61).

There were no significant differences in scores from visit 1 to 3 between the Placebo and 500 mg/day groups on mean dominant hand (p=0.16) or mean non-dominant hand (p=0.64) (Table 62).

The 250 mg/day group showed significantly greater increases from visit 1 to visit 3 for the mean dominant hand score compared to group Placebo (p<0.01). There were no significant differences in scores for the non-dominant hand from visit 1 to 3 between the 250 mg/day and Placebo groups (p=0.47) (Table 62a).

When the visit 1 to visit 3 difference scores for the 250 mg/day, Placebo and 500 mg/day groups were compared, there were significant differences detected between groups on mean dominant hand (p<0.01). Post-hoc analyses showed that the 250 mg/day group showed greater differences in scores from visit 1 to 3 on dominant hand compared to the Placebo group. There were no significant differences in scores from visit 1 to 3 between groups for mean non-dominant hand (p=0.37) (Table 64).

California Verbal Learning Test I & II (CVLT I & II)

Comparisons within Groups for Difference Scores

The 250 mg/day group showed significant improvement between visit 1 and visit 3 on CVLT List A Trial 1 (p<0.01), List A Short Delay (p=0.01), and List A Long Delay (p=0.04). There was a trend toward increases in scores for List A Trials 1-5 (p=0.06) between visit 1 and 3. There were no significant improvements detected on the List A Trial 5 (p=0.10) and List B (p=0.12) (Table 65).

The Placebo group showed significant improvement on the CVLT between visit 1 and visit 3 on List A Trial 1 (p<0.01), List A Trials 1-5 (p=0.01) and List A Long Delay (p<0.01). There was no significant improvement for the Placebo group on the CVLT between visit 1 and visit 3 on List A Trial 5 (p=0.20), List B (p=0.46), or List A Short Delay (p=0.12) (Table 66). The 500 mg/day group showed significant improvement on the CVLT between visit 1 and visit 3 on List A Trial 1 (p=0.02), List A Trial 5 (p=0.04), List A Trials 1-5 (p=0.02), List A Short Delay (p=0.03) and List A Long Delay (p=0.01). There was no significant improvement for the Placebo group on the CVLT between visit 1 and visit 3 on List B (p=0.25) (Table 67).

Comparisons Between Groups at Time 3

At time 3, no significant differences between the 250 mg/day group and the 500 mg/day group were found for CVLT performance on List A Trial 1 (p=0.81), List A Trial 5 (p=0.85), List A Trials 1-5 (p=0.80), List B (p=0.90), List A Short Delay (p=0.67), and List A Long Delay (p=0.87) (Table 68).

At time 3, there was a trend toward greater improvement in the Placebo group compared to the 500 mg/day group for List A Long Delay (p=0.07). No significant differences between the Placebo group and the 500 mg/day group were found for CVLT performance on List A Trial 1 (p=0.60), List A Trial 5 (p=0.41), List A Trials 1-5 (p=0.21), List B (p=0.80), or List A Short Delay (p=0.25) (Table 69).

At time 3, no significant differences between the 250 mg/day group and the 500 mg/day group were found for CVLT performance on List A Trial 1 (p=0.82), List A Trial 5 (p=0.60), List A Trials 1-5 (p=0.35), List B (p=0.68), List A Short Delay (p=0.51), and List A Long Delay (p=0.15) (Table 69a).

Analyses including all three groups, the Placebo group, the 250 mg/day group and the 500 mg/day group, indicated no significant differences for List A Trial 1 (p=0.45), List A Trial 5 (p=0.37), List A Trials 1-5 (p=0.24), List B (p=0.46), List A Short Delay (p=0.28), or List A Long Delay (p=0.10) (Table 70).

Comparisons Between Groups for Difference Scores

There were no significant differences in performance between visits 1 and 3 between groups 250 mg/day and 500 mg/day on List A Trial 1 (p=0.33), List A Trial 5 (p=0.56), List A Trials 1-5 (p=0.81), List B (p=0.20), List A Short Delay (p=0.90), and List A Long Delay (p=0.63) (Table 68).

There were no significant differences in performance between visits 1 and 3 between groups Placebo and 500 mg/day on List A Trial 1 (p=0.79), List A Trial 5 (p=0.50), List A Trials 1-5 (p=0.91), List B (p=0.65), List A Short Delay (p=0.69), and List A Long Delay (p=0.71) (Table 69).

There were no significant differences in performance between visits 1 and 3 between groups 250 mg/day and Placebo on List A Trial 1 (p=0.43), List A Trial 5 (p=0.87), List A Trials 1-5 (p=0.72), List B (p=0.37), List A Short Delay (p=0.59), and List A Long Delay (p=0.40) (Table 69a).

Analyses including all three groups, the Placebo group, the 250 mg/day group and the 500 mg/day group, indicated no significant differences for List A Trial 1 (p=0.28), List A Trial 5 (p=0.38), List A Trials 1-5 (p=0.47), List B (p=0.20), List A Short Delay (p=0.42), or List A Long Delay (p=0.35) (Table 71).

Rey-Osterreith Complex Figure Test (ROCFT)

Comparisons within Groups for Difference Scores

The 250 mg/day group showed significant improvement between visit 1 and visit 3 on the Immediate Raw Score (p<0.01), Delayed Raw Score (p<0.01), and the Difference Raw Score (p=0.03). There was no significant improvement detected on the Copy Raw Score (p=0.38) (Table 72).

The Placebo group showed significant improvement between visit 1 and visit 3 on the Immediate Raw Score (p<0.01), Delayed Raw Score (p<0.01). There were no significant improvements detected on the Copy Raw Score (p=0.35) or the Difference Raw Score (p=0.27) (Table 73).

The 500 mg/day group showed significant improvement between visit 1 and visit 3 on the Immediate Raw Score (p<0.01), Delayed Raw Score (p<0.01). There were no significant improvements detected on the Copy Raw Score (p=0.38) or the Difference Raw Score (p=0.44) (Table 74).

Comparisons Between Groups at Time 3

At time 3, no significant differences between the 250 mg/day group and the 500 mg/day group were found for ROCFT performance on the Copy Raw Score (p=0.68), the Immediate Raw Score (p=0.26), the Delayed Raw Score (p=0.14) or the Difference Raw Score (p=0.31) (Table 75).

At time 3, no significant differences between the Placebo group and the 500 mg/day group were found for ROCFT performance on the Copy Raw Score (p=0.43), the Immediate Raw Score (p=0.25), the Delayed Raw Score (p=0.24) or the Difference Raw Score (p=0.96) (Table 76).

At time 3, no significant differences between the 250 mg/day group and the 500 mg/day group were found for ROCFT performance on the Copy Raw Score (p=0.69), the Immediate Raw Score (p=0.99), the Delayed Raw Score (p=0.60) or the Difference Raw Score (p=0.30) (Table 76a).

Analyses including all three groups, the Placebo group, the 250 mg/day group and the 500 mg/day group, indicated no significant differences for ROCFT performance on the Copy Raw Score (p=0.36), the Immediate Raw Score (p=0.19), the Delayed Raw Score (p=0.11) or the Difference Raw Score (p=0.25) (Table 77).

Comparisons Between Groups for Difference Scores

There were no significant differences in performance between visits 1 and 3 between groups 250 mg/day and 500 mg/day for ROCFT performance on the Copy Raw Score (p=1.00), the Immediate Raw Score (p=0.86), the Delayed Raw Score (p=0.26) or the Difference Raw Score (p=0.26) (Table 75).

There were no significant differences between the Placebo group and the 500 mg/day group for ROCFT performance between visits 1 and 3 on the Copy Raw Score (p=0.64), the Immediate Raw Score (p=0.92), the Delayed Raw Score (p=0.88) or the Difference Raw Score (p=0.78) (Table 76), There were no significant differences in performance between visits 1 and 3 between groups 250 mg/day and Placebo for ROCFT performance on the Copy Raw Score (p=0.65), the Immediate Raw Score (p=0.79), the Delayed Raw Score (p=0.34) or the Difference Raw Score (p=0.35) (Table 76a).

Analyses including all three groups, the Placebo group, the 250 mg/day group and the 500 mg/day group, indicated no significant differences for ROCFT performance between visits 1 and 3 on the Copy Raw Score (p=0.44), the Immediate Raw Score (p=0.48), the Delayed Raw Score (p=0.23) or the Difference Raw Score (p=0.23) (Table 78).

Stroop Color Word Test

Comparisons within Groups for Difference Scores

On the Stroop, the 250 mg/day group showed significant improvement between visit 1 and visit 3 on the word trial (p=0.04), the color trial (p<0.01), the interference trial (p<0.01), and the difference between the interference trial and the word trial (p<0.01) (Table 79). The Placebo group showed significant improvement between visit 1 and visit 3 on the color trial (p<0.01), the interference trial (p<0.01), and the difference between the interference trial and the word trial (p<0.01). There was a trend toward improvement on the word trial (p=0.06) (Table 80).

The Placebo group showed significant improvement between visit 1 and visit 3 on the color trial (p<0.01), the interference trial (p<0.01), and the difference between the interference trial and the word trial (p<0.01). There was a trend toward improvement on the word trial (p=0.07) (Table 81).

Comparisons Between Groups at Time 3

At visit 3, there were no significant differences between the 250 mg/day group and the 500 mg/day group in Stroop performance for the word trial (p=0.65), the color trial (p=0.69), the interference trial (p=0.68), and the difference between the interference trial and the color trial (p=0.28) (Table 82).

There were no significant differences between the Placebo group and the 500 mg/day group in Stroop performance during visit 3 for the word trial (p=0.98), the color trial (p=0.46), the interference trial (p=0.56), and the difference between the interference trial and the color trial (p=0.46) (Table 83).

At visit 3, there were no significant differences between the 250 mg/day group and the Placebo group in Stroop performance for the word trial (p=0.62), the color trial (p=0.72), the interference trial (p=0.84), and the difference between the interference trial and the color trial (p=0.81) (Table 83a).

Analyses that included all three groups showed no significant differences between groups during visit 3 for the word trial (p=0.43), the color trial (p=0.38), the interference trial (p=0.41), and the difference between the interference trial and the color trial (p=0.27) (Table 84).

Comparisons Between Groups for Difference Scores

In Stroop performance between visit 1 and visit 3, there were no significant differences between the 250 mg/day group and the 500 mg/day group on the word trial (p=0.68), the color trial (p=0.25), the interference trial (p=0.53), and the difference between the interference trial and the color trial (p=0.61) (Table 82).

In Stroop performance between visit 1 and visit 3, there were no significant differences between the Placebo group and the 500 mg/day group on the word trial (p=0.96), the color trial (p=0.91), the interference trial (p=0.38), and the difference between the interference trial and the color trial (p=0.45) (Table 83).

In Stroop performance between visit 1 and visit 3, there were no significant differences between the 250 mg/day group and the Placebo group on the word trial (p=0.63), the color trial (p=0.17), the interference trial (p=0.12), and the difference between the interference trial and the color trial (p=0.21) (Table 83a).

Analyses including all three groups showed no significant differences between groups from visit 1 and visit 3 for the word trial (p=0.43), the color trial (p=0.17), the interference trial (p=0.16), and the difference between the interference trial and the color trial (p=0.23) (Table 85). Continuous Performance Test (CPT)

Comparisons within Groups for Difference Scores

The 250 mg/day group showed a significant difference between visit 1 and visit 3 on hit reaction time (p<0.01). A trend toward a difference was detected on number of omission errors (p=0.08). There were no changes between visit 1 and 3 on commission errors (p=0.15) (Table 86).

The Placebo group showed significant improvement between visit 1 and visit 3 on number of commission errors (p=0.03). No significant change was detected on number of omission errors (p=0.13) or hit reaction time (p=0.18) (Table 87).

The 500 mg/day group showed a significant difference between visit 1 and visit 3 on commission errors (p<0.01) and hit reaction time (p<0.01). A trend toward a difference was detected on number of omission errors (p=0.06) (Table 88).

Comparisons Between Groups for Time 3 Scores

At visit 3, there were no significant differences between the 250 mg/day and the 500 mg/day group for omission errors (p=0.89), commission errors (p=0.45), or hit reaction time (p=0.78) (Table 89).

There were no significant differences between the Placebo and the 500 mg/day group for omission errors (p=0.55), commission errors (p=0.87), or hit reaction time (p=0.98) during visit 3 (Table 90).

At visit 3, there were no significant differences between the 250 mg/day and the Placebo group for omission errors (p=0.39), commission errors (p=0.36), or hit reaction time (p=0.79) (Table 90a).

Analyses including all three groups indicated no significant between group differences at visit 3 on omission errors (p=0.35), commission errors (p=0.31), or hit reaction time (p=0.48) (Table 91).

Comparisons Between Groups for Difference Scores

Between visit 1 and visit 3, there were no significant differences between the 250 mg/day group and the 500 mg/day group in omission errors (p=0.93), commission errors (p=0.10), or hit reaction time (p=0.68) (Table 89).

There were no significant differences between the Placebo group and the 500 mg/day group in omission errors (p=0.67), commission errors (p=0.35), or hit reaction time (p=0.18) between visit 1 and visit 3 (Table 90).

Between visit 1 and visit 3, there were no significant differences between the 250 mg/day group and the Placebo group in omission errors (p=0.75), commission errors (p=0.49), or hit reaction time (p=0.12) (Table 90a).

When analyses were conducted including all three groups, no significant differences in difference scores between visit 1 and 3 were detected for omission errors (p=0.46), commission errors (p=0.13), or hit reaction time (p=0.12) (Table 92).

Ruff 2 & 7 Test

Comparisons within Groups for Difference Scores

The 250 mg/day group showed significant differences between visit 1 and visit 3 on the total speed score (p<0.01) and total accuracy score (p<0.01). No significant differences were detected on the speed difference score (p=0.43), accuracy difference score (p=0.26), or total difference score (p=0.40) (Table 93).

The Placebo group showed significant differences between visit 1 and visit 3 on the total speed score (p<0.01), total accuracy score (p<0.01), and total difference score (p<0.01). No significant differences were detected on the speed difference score (p=0.26) or accuracy difference score (p=0.30) (Table 94).

The 500 mg/day group showed significant differences between visit 1 and visit 3 on the total speed score (p<0.01), total accuracy score (p<0.01), speed difference score (p=0.05), and accuracy difference score (p=0.01). No significant differences were detected on the total difference score (p=0.22) (Table 95).

Comparisons Between Groups at Time 3

At time 3, there were no significant differences between the 250 mg/day and 500 mg/day group on the total speed score (p=0.72), total accuracy score (p=0.10), speed difference score (p=0.38), accuracy difference score (p=0.14), or the total difference score (p=0.37) (Table 96).

At time 3, there were significant differences between Placebo group and 500 mg/day group on the total difference score (p=0.04), and there was a trend toward a difference in the accuracy difference score (p=0.09). There were no significant differences between the Placebo and 500 mg/day group on the total speed score (p=0.23), total accuracy score (p=0.60), or speed difference score (p=0.32) (Table 97).

At time 3, there were no significant differences between the 250 mg/day and Placebo group on the total speed score (p=0.13), total accuracy score (p=0.30), speed difference score (p=0.87), accuracy difference score (p=0.81), or the total difference score (p=0.15) (Table 97a). Analyses including all three groups showed a trend toward significant differences between the 250 mg/day, Placebo, and 500 mg/day groups for the total difference score (p=0.06). Post-hoc analyses indicated a trend toward differences between the Placebo and 500 mg/day group (p=0.05). No significant differences were found between groups on the total speed score (p=0.14), total accuracy score (p=0.14), speed difference score (p=0.26), or accuracy difference score (p=0.12) (Table 98).

Comparisons Between Groups for Difference Scores

There were no significant differences between the 250 mg/day and 500 mg/day group in scores between visit 1 and visit 3 on the total speed score (p=0.84), total accuracy score (p=0.51), speed difference score (p=0.26), accuracy difference score (p=0.19), or the total difference score (p=0.61) (Table 96).

Between visit 1 and 3, there were significant differences between Placebo group and 500 mg/day group on the total difference score (p=0.02), and there was a trend toward a difference in the total speed score (p=0.05). There were no significant differences between the Placebo and 500 mg/day group on the total accuracy score (p=0.89), the speed difference score (p=0.13), or the accuracy difference score (p=0.19) (Table 97).

There were significant differences between 250 mg/day group and Placebo group between visit 1 and 3 on the total difference score (p=0.02), and there was a trend toward a difference in the total speed score (p=0.05). There were no significant differences between the 250 mg/day and Placebo group on the total accuracy score (p=0.42), the speed difference score (p=0.52), or the accuracy difference score (p=0.96) (Table 97a).

Comparison of differences between the three groups on differences in scores from visit 1 to visit 3 indicated significant differences between groups on the total difference score (p=0.01), and a trend toward differences on the total speed score (p=0.05). Post-hoc analyses revealed significant differences in the total difference score between the Placebo and 500 mg/day groups (p=0.01), as well as a trend toward differences in the total speed score between the Placebo and 500 mg/day groups (p=0.06) and the 250 mg/day and Placebo groups (p=0.08). There were no differences between the three groups on the total accuracy score (p=0.36), the speed difference score (p=0.31), or the accuracy difference score (p=0.16) (Table 99).

Wisconsin Card Sorting Test (WCST)

Comparisons Between Groups at Time 3

There were no significant differences between the 250 mg/day group and the 500 mg/day group in WCST performance during visit 3 for total cards used (p=0.81), number of categories achieved (p=0.39), total number of errors (p=0.87), total number of perseverative errors (p=0.68), number of trials to get into category (p=0.68), or number of trials to complete the categories (p=0.84) (Table 100).

There was a trend toward increased total errors at visit in the 500 mg/day group compared to the Placebo group (p=0.08). There were no significant differences between the Placebo group and the 500 mg/day group during visit 3 for total cards used (p=0.42), number of categories achieved (p=0.39), total number of perseverative errors (p=0.25), number of trials to get into category (p=0.18), and number of trials to complete the categories (p=0.72) (Table 101).

There were no significant differences between the 250 mg/day group and the Placebo group in WCST performance during visit 3 for total cards used (p=0.30), number of categories achieved (p=0.16), total number of errors (p=0.14), total number of perseverative errors (p=0.44), number of trials to get into category (p=0.25), or number of trials to complete the categories (p=0.88) (Table 101a).

Between the Placebo group, the 250 mg/day group and the 500 mg/day group, no significant differences were detected between groups during visit 3 of the WCST for total number of cards used (p=0.28), number of categories achieved (p=0.14), total number of errors (p=0.13), total number of perseverative errors (p=0.26), number of trials to get into category (p=0.22), or number of trials to complete the categories (p=0.47) (Table 102).

Trail Making Test

Comparisons within Groups for Difference Scores

On the Trail Making Test, the 250 mg/day group showed significant improvements in scores between visit 1 and visit 3 in performance times for test A (p=0.03), test B (p<0.01), and B-A test difference (p<0.01) (Table 104).

The Placebo group showed significant improvements in scores between visit 1 and visit 3 in performance times for test A (p<0.01), test B (p<0.01), and B-A test difference (p=0.03) (Table 105).

Between visit 1 and 3, the 500 mg/day group showed significant improvements in scores in performance times for test A (p<0.01) and test B (p=0.03). There were no significant improvements in the B-A test difference between visit 1 and visit 3 for the 500 mg/day group (p=0.25) (Table 106).

Comparisons Between Groups at Time 3

During visit 3, there were no significant differences between the 250 mg/day group and the 500 mg/day group in Trail Making performance times for test A (p=0.93), test B (p=0.15), and the B-A test difference (p=0.14) (Table 107).

There were no significant differences between the Placebo group and the 500 mg/day group during visit 3 for the performance times for test A (p=0.48), test B (p=0.20), and the B-A test difference (p=0.26) (Table 108).

During visit 3, there were no significant differences between the 250 mg/day group and the Placebo group in Trail Making performance times for test A (p=0.48), test B (p=0.98), and the B-A test difference (p=0.69) (Table 108a).

Analyses including all three groups at visit 3 showed significant differences between groups in performance times for test A (p=0.37), test B (p=0.10), and the B-A test difference (p=0.11) (Table 109).

Comparisons Between Groups for Difference Scores

In differences in performance times between visit 1 and visit 3, there was a trend toward a difference between the 250 mg/day and 500 mg/day groups on the B-A test difference score (p=0.08). There were no significant differences between the 250 mg/day group and the 500 mg/day group in performance time differences for test A (p=0.16) or test B (p=0.17) (Table 107). In differences in performance times between visit 1 and visit 3, there were no significant differences between the Placebo group and the 500 mg/day group in performance time differences for test A (p=0.90), test B (p=0.51), or the B-A test difference score (p=0.57) (Table 108).

In differences in performance times between visit 1 and visit 3, there were no significant differences between the 250 mg/day group and the Placebo group in performance time differences for test A (p=0.16), test B (p=0.35), or the B-A test difference score (p=0.14) (Table 108a).

Between the Placebo group, the 250 mg/day group and the 500 mg/day group, there was a positive trend towards improvement between visit 1 and visit 3 on the B-A test difference score (p=0.06). Post-hoc analyses showed a trend toward a difference in 250 mg/day and 500 mg/day groups (p=0.06). No significant differences from visit 1 to visit 3 were detected between the Placebo group, the 250 mg/day group and the 500 mg/day group for test A (p=0.12) or test B (p=0.15) difference scores between visit 1 and 3 (Table 110).

Adverse Events

Monitoring of Side Effects Scale (MOSES)

Comparisons within Groups for Difference Scores

On the MOSES, there were no significant differences for the 250 mg/day group (p=0.34) between visit 2 and 3 (Table 111).

There were no significant differences for the Placebo group between visit 2 and 3 on the MOSES (p=0.42) (Table 112).

On the MOSES, there was a trend toward significant differences for the 500 mg/day group (p=0.07) between visit 2 and 3 (Table 113).

Comparisons Between Groups at Time 3

At visit 3, no significant difference was evident between the 250 mg/day and the 500 mg/day group on the MOSES (p=0.11) (Table 114).

No significant difference was detected between the Placebo group and the 500 mg/day group during visit 3 on MOSES (p=0.85) (Table 115).

At visit 3, no significant difference was evident between the 250 mg/day and the Placebo group on the MOSES (p=0.21) (Table 115a).

When the 250 mg/day, Placebo, and the 500 mg/day groups were included in an overall analysis, no significant differences between groups were detected on the MOSES (p=0.23) (Table 116).

Comparisons Between Groups for Difference Scores

On the MOSES, there were no significant differences between the 250 mg/day group and the 500 mg/day group from visit 1 to visit 3 (p=0.64) (Table 114). There were no significant differences between the Placebo group and the 500 mg/day group from visit 1 to visit 3 (p=0.30) (Table 115).

On the MOSES, there were no significant differences between the 250 mg/day group and the Placebo group from visit 1 to visit 3 (p=0.70) (Table 115a).

There were no significant differences between group difference scores for groups 250 mg/day, Placebo, and 500 mg/day on the MOSES (p=0.66) (Table 117).

TABLE 1

Subject Demographics

|  | 250 mg/day group (N = 27) | Placebo group (N = 24) | 500 mg/day group (N = 24) |
|---|---|---|---|
| Age (+SD) | 15.33 + 1.69 | 15.71 + 1.73 | 15.50 + 1.75 |
| Education (years) | 8.96 + 1.65 | 9.42 + 1.82 | 9.04 + 1.90 |
| Height (in) (baseline) | 66.96 + 3.90 | 67.70 + 4.24 | 67.86 + 3.34 |
| Weight (lbs) (baseline) | 129.48 + 26.16 | 138.38 + 31.55 | 142.98 + 37.84 |
| IQ (baseline) | 105.00 + 11.11 | 107.33 + 9.50 | 107.21 + 9.48 |

TABLE 2

PANAS-C Visit 1 to Visit 3: 250 mg/day group

| PANAS-C | Mean | Std. Dev. | Sig (1-tailed) | Sig (2-tailed) |
|---|---|---|---|---|
| Positive Score V1 | 45.74 | 6.68 | <.01 | .01 |
| Positive Score V3 | 41.93 | 8.77 | | |
| Negative Score V1 | 23.15 | 5.15 | <.01 | <.01 |
| Negative Score V3 | 19.81 | 5.29 | | |

TABLE 3

PANAS-C Visit 1 to Visit 3: Placebo group

| PANAS-C | Mean | Std. Dev. | Sig (1-tailed) | Sig (2-tailed) |
|---|---|---|---|---|
| Positive Score V1 | 45.42 | 6.35 | .09 | .19 |
| Positive Score V3 | 43.83 | 8.48 | | |
| Negative Score V1 | 23.08 | 4.91 | .03 | .06 |
| Negative Score V3 | 20.92 | 4.93 | | |

TABLE 4

PANAS-C Visit 1 to Visit 3: 500 mg/day group

| PANAS-C | Mean | Std. Dev. | Sig (1-tailed) | Sig (2-tailed) |
|---|---|---|---|---|
| Positive Score V1 | 43.30 | 7.39 | .04 | .08 |
| Positive Score V3 | 41.78 | 7.58 | | |
| Negative Score V1 | 21.55 | 6.26 | <.01 | .01 |
| Negative Score V3 | 18.00 | 3.57 | | |

TABLE 5

PANAS-C Visit 3 and Visit Difference Scores: 250 mg/day group and 500 mg/day group

|  | 250 mg/day | | 500 mg/day | | |
|---|---|---|---|---|---|
|  | Mean | Std. Deviation | Mean | Std. Deviation | p-value |
| V3 Positive Score | 41.93 | 8.77 | 41.78 | 7.58 | .95 |
| V3 Negative Score | 19.81 | 5.29 | 18.00 | 3.57 | .18 |
| V3-V1 Positive Score | −3.81 | 7.25 | −1.52 | 4.02 | .18 |
| V3-V1 Negative Score | −3.33 | 5.20 | −3.55 | 5.93 | .89 |

TABLE 6

PANAS-C Visit 3 and Visit Difference Scores: Placebo group and 500 mg/day group

|  | Placebo | | 500 mg/day | | |
|---|---|---|---|---|---|
|  | Mean | Std. Deviation | Mean | Std. Deviation | p-value |
| V3 Positive Score | 43.83 | 8.48 | 41.78 | 7.58 | .39 |
| V3 Negative Score | 20.92 | 4.93 | 18.00 | 3.57 | .03 |
| V3-V1 Positive Score | −1.58 | 5.72 | −1.52 | 4.02 | .97 |
| V3-V1 Negative Score | −2.17 | 5.26 | −3.55 | 5.93 | .41 |

TABLE 6a

PANAS-C Visit 3 and Visit Difference Scores: 250 mg/day group and Placebo group

|  | 250 mg/day | | Placebo | | |
|---|---|---|---|---|---|
|  | Mean | Std. Deviation | Mean | Std. Deviation | p-value |
| V3 Positive Score | 41.93 | 8.77 | 43.84 | 8.48 | .44 |
| V3 Negative Score | 19.81 | 5.29 | 20.92 | 4.93 | .45 |
| V3-V1 Positive Score | −3.81 | 7.25 | −1.58 | 5.72 | .23 |
| V3-V1 Negative Score | −3.33 | 5.20 | −2.17 | 5.26 | .43 |

TABLE 7

PANAS-C Visit 3: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| Positive Score | .63 | — | .32 | — |
| 500 mg/day vs. 250 mg/day | — | 1.00 | — | .50 |
| 500 mg/day vs. Placebo | — | .68 | — | .34 |
| 250 mg/day vs. Placebo | — | .69 | — | .35 |
| Negative Score | .12 | — | .06 | — |
| 500 mg/day vs. 250 mg/day | — | .38 | — | .19 |
| 500 mg/day vs. Placebo | — | .10 | — | .05 |
| 250 mg/day vs. Placebo | — | .68 | — | .34 |

TABLE 8

PANAS-C Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| Positive Score | .29 | — | .15 | — |
| 500 mg/day vs 250 mg/day | — | .36 | — | .18 |
| 500 mg/day vs. Placebo | — | 1.00 | — | .50 |
| 250 mg/day vs. Placebo | — | .37 | — | .19 |
| Negative Score | .65 | — | .32 | — |
| 500 mg/day vs. 250 mg/day | — | 1.00 | — | .50 |

TABLE 8-continued

PANAS-C Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| 500 mg/day vs. Placebo | — | .67 | — | .33 |
| 250 mg/day vs. Placebo | — | .73 | — | .36 |

TABLE 9

CDRS Visit 1 to Visit 3: 250 mg/day group

| CDRS | Mean | Std. Dev. | Sig (1-tailed) | Sig (2-tailed) |
|---|---|---|---|---|
| V1 CDRS | 16.89 | 1.42 | .02 | .03 |
| V3 CDRS | 16.22 | .58 | | |

TABLE 10

CDRS Visit 1 to Visit 3: Placebo group

| CDRS | Mean | Std. Dev. | Sig (1-tailed) | Sig (2-tailed) |
|---|---|---|---|---|
| V1 CDRS | 16.25 | .85 | .42 | .85 |
| V3 CDRS | 16.21 | .51 | | |

TABLE 11

CDRS Visit 1 to Visit 3: 500 mg/day group

| CDRS | Mean | Std. Dev. | Sig (1-tailed) | Sig (2-tailed) |
|---|---|---|---|---|
| V1 CDRS | 16.33 | .76 | .03 | .06 |
| V3 CDRS | 16.08 | .28 | | |

TABLE 12

CDRS Visit 3 and Visit Difference Scores: 250 mg/day group and 500 mg/day group

|  | 250 mg/day | | 500 mg/day | | |
|---|---|---|---|---|---|
|  | Mean | Std. Deviation | Mean | Std. Deviation | p-value |
| V3 CDRS | 16.22 | .58 | 16.08 | .28 | .29 |
| V3-V1 Score | −.67 | 1.52 | −.25 | .61 | .22 |

TABLE 13

CDRS Visit 3 and Visit Difference Scores: Placebo group and 500 mg/day group

|  | Placebo | | 500 mg/day | | |
|---|---|---|---|---|---|
|  | Mean | Std. Deviation | Mean | Std. Deviation | p-value |
| V3 CDRS | 16.21 | .51 | 16.08 | .28 | .30 |
| V3-V1 Score | −.04 | 1.04 | −.25 | .61 | .40 |

TABLE 13a

CDRS Visit 3 and Visit Difference Scores: 250 mg/day group and Placebo group

|  | 250 mg/day | | Placebo | | |
|---|---|---|---|---|---|
|  | Mean | Std. Deviation | Mean | Std. Deviation | p-value |
| V3 CDRS | 16.22 | .58 | 16.21 | .51 | .93 |
| V3-V1 Score | −.67 | 1.52 | −.04 | 1.04 | .10 |

TABLE 14

CDRS Visit 3: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| CDRS Score | .53 | — | .27 | — |
| 500 mg/day vs. 250 mg/day | — | .56 | — | .28 |
| 500 mg/day vs. Placebo | — | .64 | — | .32 |
| 250 mg/day vs. Placebo | — | .99 | — | .50 |

TABLE 15

CDRS Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| CDRS Score | .14 | — | .07 | — |
| 500 mg/day vs. 250 mg/day | — | .40 | — | .20 |
| 500 mg/day vs. Placebo | — | .80 | — | .40 |
| 250 mg/day vs. Placebo | — | .13 | — | .07 |

TABLE 16

BIS Visit 1 to Visit 3: 250 mg/day group

| BIS | Mean | Std. Dev. | Sig (1-tailed) | Sig (2-tailed) |
|---|---|---|---|---|
| Attention V1 | 18.52 | 3.17 | .44 | .89 |
| Attention V3 | 18.59 | 3.96 | | |
| Motor V1 | 22.22 | 4.72 | .36 | .73 |
| Motor V3 | 22.00 | 5.43 | | |
| Non-planning V1 | 24.85 | 5.10 | .30 | .60 |
| Non-planning V3 | 24.44 | 4.85 | | |
| Total V1 | 65.59 | 9.31 | .35 | .70 |
| Total V3 | 65.04 | 11.35 | | |

TABLE 17

BIS Visit 1 to Visit 3: Placebo group

| BIS | Mean | Std. Dev. | Sig (1-tailed) | Sig (2-tailed) |
|---|---|---|---|---|
| Attention V1 | 16.67 | 3.75 | .45 | .91 |
| Attention V3 | 16.75 | 3.15 | | |
| Motor V1 | 20.21 | 3.65 | .40 | .80 |
| Motor V3 | 20.04 | 3.37 | | |
| Non-planning V1 | 22.67 | 3.28 | .09 | .17 |
| Non-planning V3 | 21.71 | 4.17 | | |

TABLE 17-continued

BIS Visit 1 to Visit 3: Placebo group

| BIS | Mean | Std. Dev. | Sig (1-tailed) | Sig (2-tailed) |
|---|---|---|---|---|
| Total V1 | 59.54 | 8.45 | .22 | .44 |
| Total V3 | 58.50 | 7.52 | | |

TABLE 18

BIS Visit 1 to Visit 3: 500 mg/day group

| BIS | Mean | Std. Dev. | Sig (1-tailed) | Sig (2-tailed) |
|---|---|---|---|---|
| Attention V1 | 16.54 | 3.70 | .47 | .94 |
| Attention V3 | 16.50 | 4.17 | | |
| Motor V1 | 20.21 | 3.65 | .40 | .80 |
| Motor V3 | 20.04 | 3.37 | | |
| Non-planning V1 | 22.67 | 3.28 | .09 | .17 |
| Non-planning V3 | 21.71 | 4.17 | | |
| Total V1 | 59.63 | 8.38 | .17 | .34 |
| Total V3 | 58.21 | 9.68 | | |

TABLE 19

BIS Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| V3 Attention | 18.59 | 3.96 | 16.50 | 4.17 | .07 |
| V3 Motor | 22.00 | 5.43 | 19.29 | 3.79 | .05 |
| V3 Non-planning | 24.44 | 4.85 | 22.42 | 4.13 | .12 |
| V3 Total | 65.04 | 11.35 | 58.21 | 9.68 | .91 |
| V3-V1 Attention | .07 | 2.63 | −.04 | 2.87 | .88 |
| V3-V1 Motor | −.22 | 3.27 | −1.00 | 3.83 | .44 |
| V3-V1 Non-planning | −.41 | 4.03 | −.38 | 3.90 | .98 |
| V3-V1 Total | −.56 | 7.41 | −1.42 | 7.05 | .67 |

TABLE 20

BIS Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 Attention | 16.75 | 3.15 | 16.50 | 4.17 | .82 |
| V3 Motor | 20.04 | 3.37 | 19.29 | 3.79 | .47 |
| V3 Non-planning | 21.71 | 4.17 | 22.42 | 4.13 | .56 |
| V3 Total | 58.50 | 7.52 | 58.21 | 9.68 | .91 |
| V3-V1 Attention | .08 | 3.49 | −.04 | 2.87 | .89 |
| V3-V1 Motor | −.17 | 3.16 | −1.00 | 3.83 | .42 |
| V3-V1 Non-planning | −.96 | 3.32 | −.38 | 3.90 | .58 |
| V3-V1 Total | −1.04 | 6.43 | −1.42 | 7.05 | .85 |

TABLE 20a

BIS Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 Attention | 18.59 | 3.96 | 16.75 | 3.15 | .08 |
| V3 Motor | 22.00 | 5.43 | 20.04 | 3.37 | .13 |
| V3 Non-planning | 24.44 | 4.85 | 21.71 | 4.17 | .04 |
| V3 Total | 65.04 | 11.35 | 58.50 | 7.52 | .02 |
| V3-V1 Attention | .07 | 2.63 | .08 | 3.49 | .99 |
| V3-V1 Motor | −.22 | 3.27 | −.17 | 3.16 | .95 |
| V3-V1 Non-planning | −.41 | 4.03 | −.96 | 3.32 | .60 |
| V3-V1 Total | −.56 | 7.41 | −1.04 | 6.43 | .81 |

TABLE 21

BIS Visit 3: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Attention | .10 | — | .05 | — |
| 500 mg/day vs. 250 mg/day | — | .13 | — | .06 |
| 500 mg/day vs. Placebo | — | .97 | — | .49 |
| 250 mg/day vs. Placebo | — | .20 | — | .10 |
| Motor | .08 | — | .04 | — |
| 500 mg/day vs. 250 mg/day | — | .07 | — | .04 |
| 500 mg/day vs. Placebo | — | .82 | — | .41 |
| 250 mg/day vs. Placebo | — | .25 | — | .12 |
| Non-planning | .08 | — | .04 | — |
| 500 mg/day vs. 250 mg/day | — | .24 | — | .12 |
| 500 mg/day vs. Placebo | — | .84 | — | .42 |
| 250 mg/day vs. Placebo | — | .08 | — | .04 |
| Total | .02 | — | .01 | — |
| 500 mg/day vs. 250 mg/day | — | .04 | — | .02 |
| 500 mg/day vs. Placebo | — | .99 | — | .50 |
| 250 mg/day vs. Placebo | — | .05 | — | .03 |

TABLE 22

BIS Visit Difference Scores: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Attention | .99 | — | .49 | — |
| 500 mg/day vs. 250 mg/day | — | .99 | — | .50 |
| 500 mg/day vs. Pacebo | — | .99 | — | .49 |
| 250 mg/day vs. Placebo | — | 1.00 | — | .50 |
| Motor | .64 | — | .32 | — |
| 500 mg/day vs. 250 mg/day | — | .70 | — | .35 |
| 500 mg/day vs. Placebo | — | .68 | — | .34 |
| 250 mg/day vs. Placebo | — | 1.00 | — | .50 |
| Non-planning | .83 | — | .42 | — |
| 500 mg/day vs. 250 mg/day | — | 1.00 | — | .50 |
| 500 mg/day vs. Placebo | — | .85 | — | .43 |
| 250 mg/day vs. Placebo | — | .86 | — | .43 |

TABLE 22-continued

BIS Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| Total | .91 | — | .45 | — |
| 500 mg/day vs. 250 mg/day | — | .90 | — | .45 |
| 500 mg/day vs. Placebo | — | .98 | — | .49 |
| 250 mg/day vs. Placebo | — | .97 | — | .48 |

TABLE 23

ARS Visit 1 to Visit 3: 250 mg/day group

| ARS | Mean | Std. Dev. | Sig (1-tailed) | Sig (2-tailed) |
|---|---|---|---|---|
| Inattention V1 | 1.30 | 1.64 | .17 | .34 |
| Inattention V3 | 1.56 | 2.08 | | |
| Impulsivity V1 | 1.44 | 1.45 | <1.01 | .01 |
| Impulsivity V3 | .85 | 1.29 | | |

TABLE 24

ARS Visit 1 to Visit 3: Placebo group

| ARS | Mean | Std. Dev. | Sig (1-tailed) | Sig (2-tailed) |
|---|---|---|---|---|
| Inattention V1 | .46 | .83 | .03 | .06 |
| Inattention V3 | .21 | .59 | | |
| Impulsivity V1 | .88 | 1.30 | .10 | .21 |
| Impulsivity V3 | .63 | 1.47 | | |

TABLE 25

ARS Visit 1 to Visit 3: 500 mg/day group

| ARS | Mean | Std. Dev. | Sig (1-tailed) | Sig (2-tailed) |
|---|---|---|---|---|
| Inattention V1 | .50 | .89 | .28 | .56 |
| Inattention V3 | .38 | .92 | | |
| Impulsivity V1 | .88 | 1.62 | .02 | .03 |
| Impulsivity V3 | .38 | .88 | | |

TABLE 26

ARS Visit 3 and Visit Difference Scores: 250 mg/day group and 500 mg/day group

|  | 250 mg/day | | 500 mg/day | | |
|---|---|---|---|---|---|
|  | Mean | Std. Deviation | Mean | Std. Deviation | p-value |
| V3 Inattention | 1.56 | 2.08 | .38 | .92 | .01 |
| V3 Impulsivity | .85 | 1.29 | .38 | .88 | .13 |
| V3-V1 Inattention | .26 | 1.38 | −.13 | 1.03 | .27 |
| V3-V1 Impulsivity | −.59 | 1.15 | −.50 | 1.06 | .77 |

TABLE 27

ARS Visit 3 and Visit Difference Scores: Placebo group and 500 mg/day group

|  | Placebo | | 500 mg/day | | |
|---|---|---|---|---|---|
|  | Mean | Std. Deviation | Mean | Std. Deviation | p-value |
| V3 Inattention | .21 | .59 | .38 | .92 | .46 |
| V3 Impulsivity | .63 | 1.47 | .38 | .88 | .48 |
| V3-V1 Inattention | −.25 | .61 | −.13 | 1.03 | .61 |
| V3-V1 Impulsivity | −.25 | .94 | −.50 | 1.06 | .39 |

TABLE 27a

ARS Visit 3 and Visit Difference Scores: 250 mg/day group and Placebo group

|  | 250 mg/day | | Placebo | | |
|---|---|---|---|---|---|
|  | Mean | Std. Deviation | Mean | Std. Deviation | p-value |
| V3 Inattention | 1.58 | 2.08 | .21 | .59 | <.01 |
| V3 Impulsivity | .85 | 1.29 | .63 | 1.47 | .56 |
| V3-V1 Inattention | .26 | 1.38 | −.25 | .61 | .10 |
| V3-V1 Impulsivity | −.59 | 1.15 | −.25 | .94 | .26 |

TABLE 28

ARS Visit 3: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| Inattenton | <.01 | — | <.01 | — |
| 500 mg/day vs 250 mg/day | — | .01 | — | <.01 |
| 500 mg/day vs Placebo | — | .91 | — | .46 |
| 250 mg/day vs Placebo | — | <.01 | — | <.01 |
| Impulsivity | .40 | — | .20 | — |
| 500 mg/day vs. 250 mg/day | — | .36 | — | .18 |
| 500 mg/day vs. Placebo | — | .77 | — | .38 |
| 250 mg/day vs. Placebo | — | .79 | — | .40 |

TABLE 29

ARS Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
|---|---|---|---|---|
| Inattenton | .21 | — | .11 | — |
| 500 mg/day vs 250 mg/day | — | .41 | — | .21 |
| 500 mg/day vs Placebo | — | .91 | — | .46 |
| 250 mg/day vs Placebo | — | .21 | — | .11 |
| Impulsivity | .50 | — | .25 | — |
| 500 mg/day vs. 250 mg/day | — | .95 | — | .47 |
| 500 mg/day vs. Placebo | — | .69 | — | .35 |
| 250 mg/day vs. Placebo | — | .49 | — | .24 |

TABLE 30

Conners Visit 1 to Visit 3: 250 mg/day group

| Conners | Mean | Std. Dev. | Sig (1-tailed) | Sig (2-tailed) |
|---|---|---|---|---|
| V1 Conners | 49.26 | 10.25 | .02 | .03 |
| V3 Conners | 49.52 | 10.90 | | |

TABLE 31

Conners Visit 1 to Visit 3: Placebo group

| Conners | Mean | Std. Dev. | Sig (1-tailed) | Sig (2-tailed) |
|---|---|---|---|---|
| V1 Conners | 43.92 | 7.02 | .07 | .14 |
| V3 Conners | 41.96 | 7.71 | | |

TABLE 32

Conners Visit 1 to Visit 3: 500 mg/day group

| Conners | Mean | Std. Dev. | Sig (1-tailed) | Sig (2-tailed) |
|---|---|---|---|---|
| V1 Conners | 43.83 | 9.25 | <.01 | <.01 |
| V3 Conners | 39.54 | 7.64 | | |

TABLE 33

Conners Visit 3 and Visit Difference Scores:
250 mg/day group and 500 mg/day group

| | 250 mg/day | | 500 mg/day | | |
|---|---|---|---|---|---|
| | Mean | Std. Deviation | Mean | Std. Deviation | p-value |
| V3 Conners | 46.52 | 10.90 | 39.54 | 7.64 | .01 |
| V3-V1 Score | −2.74 | 6.38 | −4.29 | 5.39 | .36 |

TABLE 34

Conners Visit 3 and Visit Difference Scores:
Placebo group and 500 mg/day group

| | Placebo | | 500 mg/day | | |
|---|---|---|---|---|---|
| | Mean | Std. Deviation | Mean | Std. Deviation | p-value |
| V3 Conners | 41.96 | 7.71 | 39.54 | 7.64 | .28 |
| V3-V1 Score | −1.96 | 6.20 | −4.29 | 5.39 | .17 |

TABLE 34a

Conners Visit 3 and Visit Difference Scores:
250 mg/day group and Placebo group

| | 250 mg/day | | Placebo | | |
|---|---|---|---|---|---|
| | Mean | Std. Deviation | Mean | Std. Deviation | p-value |
| V3 Conners | 46.52 | 10.90 | 41.96 | 7.71 | .10 |
| V3-V1 Score | −2.74 | 6.38 | −1.96 | 6.20 | .66 |

TABLE 35

Conners Visit 3: 250 mg/day, Placebo groups,
and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Conners Score | .02 | — | .01 | — |
| 500 mg/day vs 250 mg/day | — | .02 | — | .01 |
| 500 mg/day vs Placebo | — | .62 | — | .31 |
| 250 mg/day vs Placebo | — | .17 | — | .09 |

TABLE 36

Conners Visit Difference Scores: 250 mg/day,
Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Conners Score | .40 | — | .20 | — |
| 500 mg/day vs 250 mg/day | — | .63 | — | .32 |
| 500 mg/day vs Placebo | — | .38 | — | .19 |
| 250 mg/day vs Placebo | — | .89 | — | .44 |

TABLE 37

PSQI Visit 1 to Visit 3: 250 mg/day group

| PSQI | Mean | Std. Dev. | Sig (1-tailed) | Sig (2-tailed) |
|---|---|---|---|---|
| V1 PSQI | 3.41 | 1.65 | <.01 | .01 |
| V3 PSQI | 2.59 | 1.53 | | |

TABLE 38

PSQI Visit 1 to Visit 3: Placebo group

| PSQI | Mean | Std. Dev. | Sig (1-tailed) | Sig (2-tailed) |
|---|---|---|---|---|
| V1 PSQI | 3.30 | 1.52 | <.01 | <.01 |
| V3 PSQI | 2.35 | 1.72 | | |

TABLE 39

PSQI Visit 1 to Visit 3: 500 mg/day group

| PSQI | Mean | Std. Dev. | Sig (1-tailed) | Sig (2-tailed) |
|---|---|---|---|---|
| V1 PSQI | 3.38 | 1.53 | <.01 | .01 |
| V3 PSQI | 2.46 | 1.77 | | |

TABLE 40

PSQI Visit 3 and Visit Difference Scores:
250 mg/day group and 500 mg/day group

| | 250 mg/day | | 500 mg/day | | |
|---|---|---|---|---|---|
| | Mean | Std. Deviation | Mean | Std. Deviation | p-value |
| V3 PSQI | 2.59 | 1.53 | 2.46 | 1.77 | .77 |
| V3-V1 Score | −.81 | 1.55 | −.92 | 1.61 | .82 |

TABLE 41

PSQI Visit 3 and Visit Difference Scores:
Placebo group and 500 mg/day group

| | Placebo | | 500 mg/day | | |
|---|---|---|---|---|---|
| | Mean | Std. Deviation | Mean | Std. Deviation | p-value |
| V3 PSQI | 2.35 | 1.71 | 2.46 | 1.77 | .83 |
| V3-V1 Score | −.96 | 1.19 | −.92 | 1.61 | .92 |

TABLE 41a

PSQI Visit 3 and Visit Difference Scores:
250 mg/day group and Placebo group

| | 250 mg/day | | Placebo | | |
|---|---|---|---|---|---|
| | Mean | Std. Deviation | Mean | Std. Deviation | p-value |
| V3 PSQI | 2.59 | 1.53 | 2.35 | 1.72 | .60 |
| V3-VI Score | −.81 | 1.55 | −.96 | 1.19 | .72 |

TABLE 42

PSQI Visit 3: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| PSQI Score | .87 | — | .44 | — |
| 500 mg/day vs. 250 mg/day | — | .96 | — | .48 |
| 500 mg/day vs. Placebo | — | .97 | — | .49 |
| 250 mg/day vs. Placebo | — | .86 | — | .43 |

TABLE 43

PSQI Visit Difference Scores: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| PSQI Score | .94 | — | .47 | — |
| 500 mg/day vs. 250 mg/day | — | .97 | — | .48 |
| 500 mg/day vs. Placebo | — | 1.00 | — | .50 |
| 250 mg/day vs. Placebo | — | .94 | — | .47 |

TABLE 44

General Questionnaire Visit 1 to Visit 3: 250 mg/day group

| Questionnaire | Mean | Std. Dev. | Sig (1-tailed) | Sig (2-tailed) |
|---|---|---|---|---|
| Vision Q1 V1 | 3.44 | 1.95 | <.01 | <.01 |
| Vision Q1 V3 | 2.33 | 1.30 | | |
| Vision Q2 V1 | 3.26 | 2.26 | <.01 | <.01 |
| Vision Q2 V3 | 2.44 | 1.93 | | |
| Vision Q3 V1 | 2.15 | 1.35 | .07 | .14 |
| Vision Q3 V3 | 1.81 | 1.21 | | |
| Vision Total V1 | 8.85 | 4.60 | <.01 | <.01 |
| Vision Total V3 | 6.59 | 4.01 | | |
| Depression Q4 V1 | 2.59 | 1.45 | .02 | .03 |
| Depression Q4 V3 | 1.81 | 1.33 | | |
| Depression Q5 V1 | 3.26 | 1.91 | .01 | .02 |
| Depression Q5 V3 | 2.30 | 1.46 | | |
| Depression Q6 V1 | 2.85 | 1.98 | .02 | .03 |
| Depression Q6 V3 | 2.00 | 1.04 | | |
| Depression Q7 V1 | 4.26 | 2.12 | .01 | .03 |
| Depression Q7 V3 | 3.33 | 2.09 | | |
| Depression Q8 V1 | 2.74 | 2.16 | <.01 | .01 |
| Depression Q8 V3 | 1.81 | 1.21 | | |
| Depression Q9 V1 | 3.74 | 2.23 | .01 | .02 |
| Depression Q9 V3 | 2.89 | 1.81 | | |
| Depression Q10 V1 | 2.85 | 1.83 | <.01 | <.01 |
| Depression Q10 V3 | 2.07 | 1.33 | | |
| Depression Q11 V1 | 2.85 | 2.27 | .03 | .06 |
| Depression Q11 V3 | 2.15 | 1.63 | | |
| Depression Q12 V1 | 3.26 | 1.91 | .04 | .08 |
| Depression Q12 V3 | 2.67 | 1.98 | | |
| Depression Total V1 | 28.41 | 12.27 | <.01 | <.01 |
| Depression Total V3 | 21.04 | 10.73 | | |
| Attention Q13 V1 | 3.52 | 2.29 | .04 | .08 |
| Attention Q13 V3 | 2.74 | 1.83 | | |
| Attention Q14 V1 | 2.37 | 1.25 | .36 | .73 |
| Attention Q14 V3 | 2.48 | 1.58 | | |
| Attention Q15 V1 | 3.89 | 2.50 | .08 | .16 |
| Attention Q15 V3 | 3.15 | 2.11 | | |
| Attention Q16 V1 | 3.19 | 1.50 | .04 | .07 |
| Attention Q16 V3 | 2.63 | 1.71 | | |
| Attention Q17 V1 | 3.30 | 2.30 | .03 | .05 |
| Attention Q17 V3 | 2.48 | 1.53 | | |
| Attention Q18 V1 | 2.63 | 2.19 | .08 | .15 |
| Attention Q18 V3 | 2.26 | 1.87 | | |
| Attention Q19 V1 | 6.59 | 2.75 | .41 | .81 |
| Attention Q19 V3 | 6.41 | 2.72 | | |
| Attention Q20 V1 | 3.48 | 2.49 | .24 | .47 |
| Attention Q20 V3 | 3.22 | 2.52 | | |
| Attention Q21 V1 | 3.22 | 2.06 | .38 | .75 |
| Attention Q21 V3 | 3.15 | 2.35 | | |
| Attention Q22 V1 | 4.00 | 2.38 | .05 | .10 |
| Attention Q22 V3 | 3.35 | 2.59 | | |
| Attention Q23 V1 | 4.15 | 2.37 | .19 | .38 |
| Attention Q23 V3 | 3.70 | 2.51 | | |
| Attention Q24 V1 | 3.67 | 1.84 | .04 | .08 |
| Attention Q24 V3 | 2.96 | 2.14 | | |
| Attention Total V1 | 44.31 | 16.58 | .04 | .07 |
| Attention Total V3 | 38.73 | 17.66 | | |
| Sleep Q25 V1 | 3.19 | 1.88 | <.01 | .02 |
| Sleep Q25 V3 | 2.33 | 1.52 | | |
| Sleep Q26 V1 | 2.78 | 2.21 | .04 | .07 |
| Sleep Q26 V3 | 2.15 | 2.05 | | |
| Sleep Q27 V1 | 3.26 | 2.68 | .01 | .02 |
| Sleep Q27 V3 | 2.07 | 2.02 | | |
| Sleep Q28 V1 | 3.63 | 1.84 | <.01 | .01 |
| Sleep Q28 V3 | 2.78 | 1.81 | | |
| Sleep Q29 V1 | 3.48 | 2.14 | <.01 | <.01 |
| Sleep Q29 V3 | 2.19 | 1.42 | | |
| Sleep Q30 V1 | 2.11 | 1.12 | .28 | .57 |
| Sleep Q30 V3 | 1.96 | 1.32 | | |
| Sleep Q31 V1 | 1.96 | 1.02 | .42 | .84 |
| Sleep Q31 V3 | 1.93 | 1.14 | | |
| Sleep Q32 V1 | 4.15 | 1.99 | .04 | .08 |
| Sleep Q32 V3 | 3.56 | 1.99 | | |
| Sleep Total V1 | 24.56 | 8.13 | <.01 | <.01 |
| Sleep Total V3 | 18.96 | 7.66 | | |
| Complexion Q33 V1 | 2.78 | 1.76 | .03 | .05 |
| Complexion Q33 V3 | 2.30 | 1.59 | | |
| Complexion Q34 V1 | 1.85 | 1.32 | .28 | .57 |
| Complexion Q34 V3 | 1.67 | 1.30 | | |
| Complexion Total V1 | 4.63 | 2.66 | .09 | .19 |
| Complexion Total V3 | 3.96 | 2.53 | | |

TABLE 45

General Questionnaire Visit 1 to Visit 3: Placebo group

| Questionnaire | Mean | Std. Dev. | Sig (1-tailed) | Sig (2-tailed) |
|---|---|---|---|---|
| Vision Q1 V1 | 2.54 | 1.22 | <.01 | <.01 |
| Vision Q1 V3 | 1.83 | .92 | | |
| Vision Q2 V1 | 2.92 | 1.74 | .03 | .05 |
| Vision Q2 V3 | 2.00 | 1.35 | | |
| Vision Q3 V1 | 1.79 | 1.35 | .04 | .09 |
| Vision Q3 V3 | 1.33 | .57 | | |
| Vision Total V1 | 7.25 | 3.48 | <.01 | <.01 |
| Vision Total V3 | 5.17 | 2.12 | | |
| Depression Q4 V1 | 2.04 | 1.60 | .08 | .16 |
| Depression Q4 V3 | 1.58 | .93 | | |
| Depression Q5 V1 | 2.75 | 1.57 | <.01 | <.01 |
| Depression Q5 V3 | 1.92 | .97 | | |
| Depression Q6 V1 | 2.71 | 1.63 | <.01 | <.01 |
| Depression Q6 V3 | 1.79 | .93 | | |
| Depression Q7 V1 | 3.71 | 1.43 | <.01 | <.01 |
| Depression Q7 V3 | 2.75 | 1.23 | | |
| Depression Q8 V1 | 1.88 | 1.26 | .10 | .21 |
| Depression Q8 V3 | 1.50 | .83 | | |
| Depression Q9 V1 | 2.58 | 1.61 | .37 | .73 |
| Depression Q9 V3 | 2.67 | 1.49 | | |
| Depression Q10 V1 | 2.54 | 1.59 | <.01 | <.01 |
| Depression Q10 V3 | 1.67 | .96 | | |
| Depression Q11 V1 | 2.29 | 1.68 | .03 | .07 |
| Depression Q11 V3 | 1.71 | 1.20 | | |
| Depression Q12 V1 | 2.33 | 1.66 | .05 | .11 |
| Depression Q12 V3 | 1.75 | .94 | | |
| Depression Total V1 | 22.83 | 11.01 | <.01 | <.01 |
| Depression Total V3 | 17.33 | 6.24 | | |
| Attention Q13 V1 | 2.63 | 1.31 | .01 | .03 |
| Attention Q13 V3 | 2.04 | .86 | | |
| Attention Q14 V1 | 2.58 | 1.89 | .16 | .32 |
| Attention Q14 V3 | 2.13 | 1.33 | | |
| Attention Q15 V1 | 3.29 | 1.97 | <.01 | <.01 |
| Attention Q15 V3 | 2.67 | 2.01 | | |
| Attention Q16 V1 | 2.83 | 1.40 | .05 | .11 |
| Attention Q16 V3 | 2.46 | 1.14 | | |
| Attention Q17 V1 | 2.67 | 1.58 | .04 | .08 |
| Attention Q17 V3 | 2.21 | 1.53 | | |
| Attention Q18 V1 | 2.04 | 1.40 | .22 | .45 |
| Attention Q18 V3 | 1.83 | 1.01 | | |
| Attention Q19 V1 | 7.00 | 2.60 | .48 | .96 |
| Attention Q19 V3 | 6.96 | 3.03 | | |
| Attention Q20 V1 | 2.79 | 1.62 | <.01 | <.01 |
| Attention Q20 V3 | 1.92 | .97 | | |
| Attention Q21 V1 | 2.88 | 1.71 | .03 | .05 |
| Attention Q21 V3 | 2.17 | 1.47 | | |
| Attention Q22 V1 | 2.58 | 1.91 | .01 | .03 |
| Attention Q22 V3 | 2.00 | 1.35 | | |
| Attention Q23 V1 | 2.96 | 1.63 | .45 | .90 |
| Attention Q23 V3 | 2.92 | 1.91 | | |
| Attention Q24 V1 | 2.79 | 1.41 | .04 | .09 |
| Attention Q24 V3 | 2.38 | 1.47 | | |
| Attention Total V1 | 37.04 | 13.08 | <.01 | <.01 |
| Attention Total V3 | 31.67 | 11.73 | | |
| Sleep Q25 V1 | 2.67 | 1.49 | <.01 | <.01 |
| Sleep Q25 V3 | 1.79 | .83 | | |
| Sleep Q26 V1 | 2.38 | 1.35 | .01 | .02 |
| Sleep Q26 V3 | 1.75 | 1.39 | | |
| Sleep Q27 V1 | 2.29 | 1.65 | <.01 | .01 |
| Sleep Q27 V3 | 1.58 | 1.14 | | |
| Sleep Q28 V1 | 3.04 | 1.71 | .03 | .07 |
| Sleep Q28 V3 | 2.33 | 1.66 | | |
| Sleep Q29 V1 | 2.29 | 1.52 | .33 | .66 |
| Sleep Q29 V3 | 2.21 | 1.84 | | |
| Sleep Q30 V1 | 1.96 | 1.08 | .32 | .63 |
| Sleep Q30 V3 | 1.83 | .76 | | |
| Sleep Q31 V1 | 1.83 | 1.05 | .26 | .52 |
| Sleep Q31 V3 | 1.71 | .91 | | |
| Sleep Q32 V1 | 3.58 | 1.59 | .10 | .21 |
| Sleep Q32 V3 | 3.21 | 1.62 | | |
| Sleep Total V1 | 20.04 | 7.11 | <.01 | <.01 |
| Sleep Total V3 | 16.42 | 7.41 | | |
| Complexion Q33 V1 | 3.13 | 1.70 | <.01 | .01 |
| Complexion Q33 V3 | 2.04 | 1.27 | | |
| Complexion Q34 V1 | 1.96 | 1.40 | .03 | .06 |
| Complexion Q34 V3 | 1.46 | .66 | | |
| Complexion Total V1 | 5.08 | 2.41 | <.01 | <.01 |
| Complexion Total V3 | 3.50 | 1.67 | | |

TABLE 46

General Questionnaire Visit 1 to Visit 3: 500 mg/day group

| Questionnaire | Mean | Std. Dev. | Sig (1-tailed) | Sig (2-tailed) |
|---|---|---|---|---|
| Vision Q1 V1 | 2.75 | 1.65 | <.01 | .01 |
| Vision Q1 V3 | 1.92 | .93 | | |
| Vision Q2 V1 | 2.54 | 1.82 | .03 | .06 |
| Vision Q2 V3 | 2.08 | 1.18 | | |
| Vision Q3 V1 | 1.71 | 1.08 | .10 | .20 |
| Vision Q3 V3 | 1.50 | .66 | | |
| Vision Total V1 | 7.00 | 4.11 | <.01 | .02 |
| Vision Total V3 | 5.50 | 2.25 | | |
| Depression Q4 V1 | 1.75 | 1.29 | .23 | .46 |
| Depression Q4 V3 | 1.58 | 1.02 | | |
| Depression Q5 V1 | 2.46 | 1.50 | .03 | .06 |
| Depression Q5 V3 | 1.88 | 1.08 | | |
| Depression Q6 V1 | 2.21 | 1.38 | .04 | .08 |
| Depression Q6 V3 | 1.67 | .87 | | |
| Depression Q7 V1 | 3.13 | 1.65 | <.01 | <.01 |
| Depression Q7 V3 | 2.25 | 1.36 | | |
| Depression Q8 V1 | 1.92 | 1.21 | .03 | .05 |
| Depression Q8 V3 | 1.46 | .66 | | |
| Depression Q9 V1 | 3.04 | 1.88 | .01 | .02 |
| Depression Q9 V3 | 2.00 | 1.32 | | |
| Depression Q10 V1 | 2.00 | 1.56 | .06 | .12 |
| Depression Q10 V3 | 1.54 | .93 | | |
| Depression Q11 V1 | 2.00 | 1.10 | <.01 | .01 |
| Depression Q11 V3 | 1.38 | .77 | | |
| Depression Q12 V1 | 2.04 | 1.37 | .03 | .07 |
| Depression Q12 V3 | 1.58 | .83 | | |
| Depression Total V1 | 20.54 | 9.99 | <.01 | <.01 |
| Depression Total V3 | 15.33 | 6.49 | | |
| Attention Q13 V1 | 2.42 | 1.21 | .03 | .05 |
| Attention Q13 V3 | 1.96 | 1.08 | | |
| Attention Q14 V1 | 2.21 | 1.32 | .09 | .18 |
| Attention Q14 V3 | 1.83 | .92 | | |
| Attention Q15 V1 | 2.63 | 1.79 | .03 | .05 |
| Attention Q15 V3 | 1.92 | 1.06 | | |
| Attention Q16 V1 | 2.83 | 1.49 | <.01 | .02 |
| Attention Q16 V3 | 1.92 | 1.02 | | |
| Attention Q17 V1 | 1.96 | 1.04 | .21 | .41 |
| Attention Q17 V3 | 1.75 | .74 | | |
| Attention Q18 V1 | 2.79 | 2.32 | .05 | .11 |
| Attention Q18 V3 | 1.92 | 1.79 | | |
| Attention Q19 V1 | 7.29 | 2.63 | .06 | .13 |
| Attention Q19 V3 | 8.42 | 2.32 | | |
| Attention Q20 V1 | 2.54 | 1.79 | .05 | .09 |
| Attention Q20 V3 | 1.92 | 1.14 | | |
| Attention Q21 V1 | 3.25 | 2.15 | <.01 | <.01 |
| Attention Q21 V3 | 2.42 | 1.89 | | |
| Attention Q22 V1 | 1.83 | .76 | .13 | .26 |
| Attention Q22 V3 | 1.63 | .77 | | |
| Attention Q23 V1 | 2.92 | 1.74 | .01 | .03 |
| Attention Q23 V3 | 2.13 | 1.36 | | |
| Attention Q24 V1 | 2.46 | 1.56 | .14 | .28 |
| Attention Q24 V3 | 2.17 | 1.40 | | |
| Attention Total V1 | 35.13 | 12.78 | .01 | .02 |
| Attention Total V3 | 29.96 | 9.62 | | |
| Sleep Q25 V1 | 3.54 | 2.04 | <.01 | .01 |
| Sleep Q25 V3 | 2.50 | 1.10 | | |
| Sleep Q26 V1 | 2.54 | 1.87 | .02 | .05 |
| Sleep Q26 V3 | 1.71 | 1.43 | | |
| Sleep Q27 V1 | 2.00 | 1.41 | .31 | .62 |
| Sleep Q27 V3 | 1.83 | 1.58 | | |
| Sleep Q28 V1 | 2.96 | 1.60 | .02 | .03 |
| Sleep Q28 V3 | 2.29 | 1.23 | | |
| Sleep Q29 V1 | 2.00 | 1.45 | .41 | .82 |
| Sleep Q29 V3 | 1.96 | 1.23 | | |

TABLE 46-continued

General Questionnaire Visit 1 to Visit 3: 500 mg/day group

| Questionnaire | Mean | Std. Dev. | Sig (1-tailed) | Sig (2-tailed) |
|---|---|---|---|---|
| Sleep Q30 V1 | 2.04 | 1.20 | .38 | .75 |
| Sleep Q30 V3 | 1.96 | .96 | | |
| Sleep Q31 V1 | 2.33 | 1.13 | .31 | .61 |
| Sleep Q31 V3 | 2.21 | 1.50 | | |
| Sleep Q32 V1 | 3.54 | 1.79 | .09 | .18 |
| Sleep Q32 V3 | 3.13 | 1.92 | | |
| Sleep Total V1 | 20.83 | 5.48 | <.01 | <.01 |
| Sleep Total V3 | 17.58 | 6.85 | | |
| Complexion Q33 V1 | 2.58 | 1.28 | <.01 | <.01 |
| Complexion Q33 V3 | 1.75 | .94 | | |
| Complexion Q34 V1 | 1.88 | 1.26 | <.01 | <.01 |
| Complexion Q34 V3 | 1.29 | .62 | | |
| Complexion Total V1 | 4.46 | 2.13 | .01 | <.01 |
| Complexion Total V3 | 3.04 | 1.40 | | |

TABLE 47

General Questionnaire Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| Vision Total V3 | 6.59 | 4.01 | 5.50 | 2.25 | .24 |
| Depression Total V3 | 21.04 | 10.73 | 15.33 | 6.49 | .03 |
| Attention Total V3 | 38.48 | 17.37 | 29.96 | 9.62 | .04 |
| Sleep Total V3 | 18.96 | 7.66 | 17.58 | 6.85 | .50 |
| Complexion Total V3 | 3.96 | 2.53 | 3.04 | 1.40 | .12 |
| Vision Total V3-V1 Difference | −2.26 | 3.11 | −1.50 | 2.92 | .38 |
| Depression Total V3-V1 Difference | −7.37 | 9.53 | −5.21 | 8.42 | .40 |
| Attention Total V3-V1 Difference | −5.58 | 15.16 | −5.17 | 10.10 | .91 |
| Sleep Total V3-V1 Difference | −5.59 | 6.76 | −3.25 | 5.03 | .17 |
| Complexion Total V3-V1 Difference | −.67 | 2.54 | −1.42 | 1.69 | .23 |

TABLE 48

General Questionnaire Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| Vision Total V3 | 5.17 | 2.12 | 5.50 | 2.25 | .60 |
| Depression Total V3 | 17.33 | 6.24 | 15.33 | 6.49 | .28 |
| Attention Total V3 | 31.67 | 11.73 | 29.96 | 9.62 | .58 |
| Sleep Total V3 | 16.42 | 7.41 | 17.58 | 6.85 | .57 |
| Complexion Total V3 | 3.50 | 1.67 | 3.04 | 1.40 | .31 |
| Vision Total V3-V1 Difference | −2.08 | 3.19 | −1.50 | 2.92 | .51 |
| Depression Total V3-V1 Difference | −5.50 | 9.07 | −5.21 | 8.42 | .91 |
| Attention Total V3-V1 Difference | −5.38 | 8.32 | −5.17 | 10.10 | .94 |
| Sleep Total V3-V1 Difference | −3.63 | 4.73 | −3.25 | 5.03 | .79 |
| Complexion Total V3-V1 Difference | −1.58 | 2.62 | −1.42 | 1.69 | .80 |

TABLE 48a

General Questionnaire Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| Vision Total V3 | 6.59 | 4.01 | 5.17 | 2.12 | .13 |
| Depression Total V3 | 21.04 | 10.73 | 17.33 | 6.24 | .15 |
| Attention Total V3 | 38.48 | 17.37 | 31.67 | 11.73 | .11 |
| Sleep Total V3 | 18.96 | 7.66 | 16.42 | 7.41 | .24 |
| Complexion Total V3 | 3.96 | 2.53 | 3.50 | 1.67 | .45 |
| Vision Total V3-V1 Difference | −2.26 | 3.11 | −2.08 | 3.19 | .84 |
| Depression Total V3-V1 Difference | −7.37 | 9.53 | −5.50 | 9.07 | .48 |
| Attention Total V3-V1 Difference | −5.58 | 15.16 | −5.38 | 8.32 | .95 |
| Sleep Total V3-V1 Difference | −5.59 | 6.76 | −3.63 | 4.73 | .24 |
| Complexion Total V3-V1 Difference | −.67 | 2.54 | −1.58 | 2.62 | .21 |

TABLE 49

General Questionnaire Visit 3: 250 mg/day, Placebo, and 500 mg/day groups

| | Between Groups Overall p 2-tailed | Between groups p (2-tailed) | Between Groups Overall p (1-tailed) | Between groups p (1-tailed) |
|---|---|---|---|---|
| Vision Total | .21 | | .10 | |
| 500 mg/day vs 250 mg/day | | .40 | | .20 |
| 500 mg/day vs Placebo | | .92 | | .46 |

TABLE 49-continued

General Questionnaire Visit 3: 250 mg/day, Placebo, and 500 mg/day groups

|  | Between Groups Overall p 2-tailed | Between groups p (2-tailed) | Between Groups Overall p (1-tailed) | Between groups p (1-tailed) |
|---|---|---|---|---|
| 250 mg/day vs Placebo |  | .21 |  | .10 |
| Depression Total | .05 |  | .02 |  |
| 500 mg/day vs 250 mg/day |  | .04 |  | .02 |
| 500 mg/day vs Placebo |  | .68 |  | .34 |
| 250 mg/day vs Placebo |  | .25 |  | .12 |
| Attention Total | .06 |  | .03 |  |
| 500 mg/day vs 250 mg/day |  | .07 |  | .04 |
| 500 mg/day vs Placebo |  | .90 |  | .45 |
| 250 mg/day vs Placebo |  | .18 |  | .09 |
| Sleep Total | .47 |  | .23 |  |
| 500 mg/day vs 250 mg/day |  | .78 |  | .39 |
| 500 mg/day vs Placebo |  | .85 |  | .42 |
| 250 mg/day vs Placebo |  | .44 |  | .22 |
| Complexion Total | .25 |  | .13 |  |
| 500 mg/day vs 250 mg/day |  | .22 |  | .11 |
| 500 mg/day vs Placebo |  | .70 |  | .35 |
| 250 mg/day vs Placebo |  | .68 |  | .34 |

TABLE 50

General Questionnaire Visit Difference Scores: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Vision Total | .66 |  | .33 |  |
| 500 mg/day vs 250 mg/day |  | .66 |  | .33 |
| 500 mg/day vs Placebo |  | .79 |  | .39 |
| 250 mg/day vs Placebo |  | .98 |  | .49 |
| Depression Total | .65 |  | .32 |  |
| 500 mg/day vs 250 mg/day |  | .67 |  | .34 |
| 500 mg/day vs Placebo |  | .99 |  | .50 |
| 250 mg/day vs Placebo |  | .74 |  | .37 |
| Attention Total | .99 |  | .50 |  |
| 500 mg/day vs 250 mg/day |  | .99 |  | .50 |
| 500 mg/day vs Placebo |  | 1.00 |  | .50 |
| 250 mg/day vs Placebo |  | 1.00 |  | .50 |
| Sleep Total | .28 |  | .14 |  |
| 500 mg/day vs 250 mg/day |  | .31 |  | .15 |
| 500 mg/day vs Placebo |  | .97 |  | .49 |
| 250 mg/day vs Placebo |  | .43 |  | .22 |
| Complexion Total | .33 |  | .16 |  |
| 500 mg/day vs 250 mg/day |  | .49 |  | .24 |
| 500 mg/day vs Placebo |  | .97 |  | .48 |
| 250 mg/day vs Placebo |  | .35 |  | .17 |

TABLE 51

Exercise/Lifestyle Questionnaire Visit 1 to Visit 3: 250 mg/day group

| Questionnaire | Mean | Std. Dev. | Sig (1-tailed) | Sig (2-tailed) |
|---|---|---|---|---|
| Exercise Q1 V1 | 1.15 | .36 | .16 | .33 |
| Exercise Q1 V3 | 1.07 | .27 |  |  |
| Exercise Q2 V1 | 6.35 | 4.78 | .37 | .73 |
| Exercise Q2 V3 | 6.80 | 6.13 |  |  |
| Exercise Q3 V1 | 3.56 | 1.81 | .07 | .14 |
| Exercise Q3 V3 | 3.11 | 1.63 |  |  |
| Exercise Q4 V1 | 3.81 | 2.04 | .05 | .10 |
| Exercise Q4 V3 | 3.11 | 1.72 |  |  |
| Exercise Total V1 | 14.87 | 5.46 | .29 | .58 |
| Exercise Total V3 | 14.09 | 7.15 |  |  |
| Appetite Q5 V1 | 4.11 | 2.03 | .46 | .92 |
| Appetite Q5 V3 | 4.15 | 1.96 |  |  |
| Appetite Q6 V1 | 4.44 | 2.29 | .04 | .07 |
| Appetite Q6 V3 | 3.81 | 2.35 |  |  |
| Appetite Total V1 | 8.56 | 2.68 | .08 | .15 |
| Appetite Total V3 | 7.96 | 2.78 |  |  |
| Smoke Q7 V1 | .00 | .01 | na | na |
| Smoke Q7 V3 | .00 | .01 |  |  |
| Smoke Q8 V1 | 1.00 | .00 | na | na |
| Smoke Q8 V3 | 1.00 | .00 |  |  |
| Smoke Q9 V1 | 1.07 | .39 | .16 | .33 |
| Smoke Q9 V3 | 1.00 | .00 |  |  |
| Smoke Total V1 | 2.08 | .39 | .16 | .33 |
| Smoke Total V3 | 2.00 | .01 |  |  |
| Alcohol Q10 V1 | .07 | .38 | na | na |
| Alcohol Q10 V3 | .07 | .38 |  |  |
| Alcohol Q11 V1 | 1.00 | .00 | na | na |
| Alcohol Q11 V3 | 1.00 | .00 |  |  |
| Alcohol Q12 V1 | 1.00 | .00 | na | na |
| Alcohol Q12 V3 | 1.00 | .00 |  |  |
| Alcohol Total V1 | 2.07 | .38 | na | na |
| Alcohol Total V3 | 2.07 | .38 |  |  |

TABLE 52

Exercise/Lifestyle Questionnaire Visit 1 to Visit 3: Placebo group

| Questionnaire | Mean | Std. Dev. | Sig (1-tailed) | Sig (2-tailed) |
|---|---|---|---|---|
| Exercise Q1 V1 | 1.13 | .34 | .16 | .33 |
| Exercise Q1 V3 | 1.04 | .36 |  |  |
| Exercise Q2 V1 | 8.77 | 6.13 | .44 | .89 |
| Exercise Q2 V3 | 8.96 | 7.95 |  |  |
| Exercise Q3 V1 | 3.33 | 1.88 | .12 | .25 |
| Exercise Q3 V3 | 2.83 | 1.52 |  |  |
| Exercise Q4 V1 | 4.00 | 2.23 | .01 | .02 |
| Exercise Q4 V3 | 3.08 | 1.72 |  |  |
| Exercise Total V1 | 17.23 | 7.36 | .20 | .39 |

TABLE 52-continued

Exercise/Lifestyle Questionnaire Visit 1 to Visit 3: Placebo group

| Questionnaire | Mean | Std. Dev. | Sig (1-tailed) | Sig (2-tailed) |
|---|---|---|---|---|
| Exercise Total V3 | 15.92 | 7.90 | | |
| Appetite Q5 V1 | 4.08 | 1.69 | .04 | .09 |
| Appetite Q5 V3 | 3.63 | 1.56 | | |
| Appetite Q6 V1 | 3.38 | 1.93 | <.01 | <.01 |
| Appetite Q6 V3 | 2.29 | 1.71 | | |
| Appetite Total V1 | 7.46 | 2.55 | <.01 | <.01 |
| Appetite Total V3 | 5.92 | 2.47 | | |
| Smoke Q7 V1 | .00 | .00 | na | na |
| Smoke Q7 V3 | .00 | .00 | | |
| Smoke Q8 V1 | 1.00 | .00 | na | na |
| Smoke Q8 V3 | 1.00 | .00 | | |
| Smoke Q9 V1 | 1.00 | .00 | na | na |
| Smoke Q9 V3 | 1.00 | .00 | | |
| Smoke Total V1 | 2.00 | .00 | na | na |
| Smoke Total V3 | 2.00 | .00 | | |
| Alcohol Q10 V1 | .00 | .00 | na | na |
| Alcohol Q10 V3 | .00 | .00 | | |
| Alcohol Q11 V1 | 1.04 | .20 | .16 | .33 |
| Alcohol Q11 V3 | 1.00 | .00 | | |
| Alcohol Q12 V1 | 1.00 | .00 | na | na |
| Alcohol Q12 V3 | 1.00 | .00 | | |
| Alcohol Total V1 | 2.04 | .20 | .16 | .33 |
| Alcohol Total V3 | 2.00 | .00 | | |

TABLE 53

Exercise/Lifestyle Questionnaire Visit 1 to Visit 3: 500 mg/day group

| Questionnaire | Mean | Std. Dev. | Sig (1-tailed) | Sig (2-tailed) |
|---|---|---|---|---|
| Exercise Q1 V1 | 1.17 | .38 | .16 | .33 |
| Exercise Q1 V3 | 1.13 | .34 | | |
| Exercise Q2 V1 | 8.50 | 6.56 | .11 | .22 |
| Exercise Q2 V3 | 7.54 | 5.59 | | |
| Exercise Q3 V1 | 3.71 | 1.81 | .01 | .02 |
| Exercise Q3 V3 | 2.96 | 1.63 | | |
| Exercise Q4 V1 | 3.75 | 1.96 | <.01 | .01 |
| Exercise Q4 V3 | 2.75 | 2.07 | | |
| Exercise Total V1 | 17.24 | 7.07 | <.01 | .02 |
| Exercise Total V3 | 14.46 | 5.49 | | |
| Appetite Q5 V1 | 3.96 | 1.40 | .13 | .26 |
| Appetite Q5 V3 | 3.50 | 1.47 | | |
| Appetite Q6 V1 | 3.25 | 2.13 | .20 | .40 |
| Appetite Q6 V3 | 2.88 | 1.83 | | |
| Appetite Total V1 | 7.21 | 2.93 | .09 | .18 |
| Appetite Total V3 | 6.38 | 2.50 | | |
| Smoke Q7 V1 | .00 | .00 | na | na |
| Smoke Q7 V3 | .00 | .00 | | |
| Smoke Q8 V1 | 1.00 | .00 | na | na |
| Smoke Q8 V3 | 1.00 | .00 | | |
| Smoke Q9 V1 | 1.00 | .00 | na | na |
| Smoke Q9 V3 | 1.00 | .00 | | |
| Smoke Total V1 | 2.00 | .00 | na | na |
| Smoke Total V3 | 2.00 | .00 | | |
| Alcohol Q10 V1 | .00 | .00 | na | na |
| Alcohol Q10 V3 | .00 | .00 | | |
| Alcohol Q11 V1 | 1.00 | .00 | na | na |
| Alcohol Q11 V3 | 1.00 | .00 | | |
| Alcohol Q12 V1 | 1.00 | .00 | na | na |
| Alcohol Q12 V3 | 1.00 | .00 | | |
| Alcohol Total V1 | 2.00 | .00 | na | na |
| Alcohol Total V3 | 2.00 | .00 | | |

TABLE 54

Exercise/Lifestyle Questionnaire Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| Exercise Total V3 | 14.09 | 7.15 | 14.48 | 5.37 | .83 |
| Appetite Total V3 | 7.96 | 2.78 | 6.38 | 2.50 | .04 |
| Smoke Total V3 | 2.00 | .01 | 2.00 | .00 | .35 |
| Alcohol Total V3 | 2.07 | .38 | 2.00 | .00 | .35 |
| Exercise Total V3-V1 | −.78 | 7.17 | −2.78 | 5.25 | .27 |
| Appetite Total V3-V1 | −.59 | 2.10 | −.83 | 2.94 | .74 |
| Smoke Total V3-V1 | −.07 | .38 | .00 | .00 | .35 |
| Alcohol Total V3-V1 | .00 | .00 | .00 | .00 | na |

TABLE 55

Exercise/Lifestyle Questionnaire Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| Exercise Total V3 | 15.92 | 7.90 | 14.48 | 5.37 | .47 |
| Appetite Total V3 | 5.92 | 2.47 | 6.38 | 2.50 | .53 |
| Smoke Total V3 | 2.00 | .00 | 2.00 | .00 | na |
| Alcohol Total V3 | 2.00 | .00 | 2.00 | .00 | na |
| Exercise Total V3-V1 | −1.31 | 7.37 | −2.78 | 5.25 | .44 |
| Appetite Total V3-V1 | −1.54 | 2.02 | −.83 | 2.94 | .34 |
| Smoke Total V3-V1 | .00 | .00 | .00 | .00 | na |
| Alcohol Total V3-V1 | −.04 | .20 | .00 | .00 | .32 |

TABLE 55a

Exercise/Lifestyle Questionnaire Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| Exercise Total V3 | 14.09 | 7.15 | 15.92 | 7.90 | .39 |
| Appetite Total V3 | 7.96 | 2.78 | 5.92 | 2.47 | <.01 |
| Smoke Total V3 | 2.00 | .01 | 2.00 | .00 | .35 |
| Alcohol Total V3 | 2.07 | .38 | 2.00 | .00 | .35 |
| Exercise Total V3-V1 | −.78 | 7.17 | −1.31 | 7.37 | .79 |
| Appetite Total V3-V1 | −.59 | 2.10 | −1.54 | 2.02 | .11 |

TABLE 55a-continued

Exercise/Lifestyle Questionnaire Visit 3 and Visit Difference Scores: 250 mg/day group and Placebo group

|  | 250 mg/day | | Placebo | | |
|---|---|---|---|---|---|
|  | Mean | Std. Deviation | Mean | Std. Deviation | p-value |
| Smoke Total V3-V1 | -.07 | .38 | .00 | .00 | .35 |
| Alcohol Total V3-V1 | .00 | .00 | -.04 | .20 | .29 |

TABLE 56

Exercise/Lifestyle Questionnaire Visit 3: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Exercise Total | .62 |  | .31 |  |
| 500 mg/day vs 250 mg/day |  | .98 |  | .49 |
| 500 mg/day vs Placebo |  | .75 |  | .38 |
| 250 mg/day vs Placebo |  | .62 |  | .31 |
| Appetite Total | .02 |  | .01 |  |
| 500 mg/day vs 250 mg/day |  | .08 |  | .04 |
| 500 mg/day vs Placebo |  | .81 |  | .41 |
| 250 mg/day vs Placebo |  | .02 |  | .01 |
| Smoking Total | .42 |  | .21 |  |
| 500 mg/day vs 250 mg/day |  | .49 |  | .25 |
| 500 mg/day vs Placebo |  | 1.00 |  | .50 |
| 250 mg/day vs Placebo |  | .49 |  | .25 |
| Alcohol Total | .42 |  | .21 |  |
| 500 mg/day vs 250 mg/day |  | .49 |  | .25 |
| 500 mg/day vs Placebo |  | 1.00 |  | .50 |
| 250 mg/day vs Placebo |  | .49 |  | .25 |

TABLE 57

Exercise/Lifestyle Questionnaire Visit Difference Scores: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Exercise Total | .56 |  | .28 |  |
| 500 mg/day vs 250 mg/day |  | .55 |  | .27 |
| 500 mg/day vs Placebo |  | .73 |  | .37 |
| 250 mg/day vs Placebo |  | .96 |  | .48 |
| Appetite Total | .35 |  | .17 |  |
| 500 mg/day vs 250 mg/day |  | .93 |  | .47 |
| 500 mg/day vs Placebo |  | .56 |  | .28 |
| 250 mg/day vs Placebo |  | .34 |  | .17 |
| Smoking Total | .42 |  | .21 |  |
| 500 mg/day vs 250 mg/day |  | .49 |  | .25 |
| 500 mg/day vs Placebo |  | 1.00 |  | .50 |
| 250 mg/day vs Placebo |  | .49 |  | .25 |
| Alcohol Total | .35 |  | .18 |  |
| 500 mg/day vs 250 mg/day |  | 1.00 |  | .50 |
| 500 mg/day vs Placebo |  | .43 |  | .21 |
| 250 mg/day vs Placebo |  | .41 |  | .20 |

TABLE 58

Finger Tap Test Visit 1 to Visit 3: 250 mg/day group

| Finger Tap Test | Mean | Std. Dev. | Sig (1-tailed) | Sig (2-tailed) |
|---|---|---|---|---|
| V1 Mean Dominant Hand | 46.72 | 7.48 | <.01 | <.01 |
| V3 Mean Dominant Hand | 51.59 | 4.97 |  |  |
| V1 Mean Non-Dominant Hand | 44.52 | 7.15 | <.01 | <.01 |
| V3 Mean Non-Dominant Hand | 47.01 | 6.47 |  |  |

TABLE 59

Finger Tap Test Visit 1 to Visit 3: Placebo group

| Finger Tap Test | Mean | Std. Dev. | Sig (1-tailed) | Sig (2-tailed) |
|---|---|---|---|---|
| V1 Mean Dominant Hand | 50.49 | 8.11 | .19 | .38 |
| V3 Mean Dominant Hand | 51.34 | 6.40 |  |  |
| V1 Mean Non-Dominant Hand | 45.68 | 5.66 | .04 | .08 |
| V3 Mean Non-Dominant Hand | 47.34 | 5.70 |  |  |

TABLE 60

Finger Tap Test Visit 1 to Visit 3: 500 mg/day group

| Finger Tap Test | Mean | Std. Dev. | Sig (1-tailed) | Sig (2-tailed) |
|---|---|---|---|---|
| V1 Mean Dominant Hand | 49.44 | 6.10 | <.01 | <.01 |
| V3 Mean Dominant Hand | 52.05 | 5.10 |  |  |
| V1 Mean Non-Dominant Hand | 44.89 | 7.10 | <.01 | <.01 |
| V3 Mean Non-Dominant Hand | 47.10 | 5.58 |  |  |

TABLE 61

Finger Tap Test Visit 3 and Visit Difference Scores: 250 mg/day group and 500 mg/day

| | 250 mg/day | | 500 mg/day | | |
|---|---|---|---|---|---|
| | Mean | Std. Deviation | Mean | Std. Deviation | p-value |
| V3 Mean Dominant Hand | 51.59 | 4.97 | 52.05 | 5.10 | .75 |
| V3 Mean Non-Dominant Hand | 47.01 | 6.47 | 47.10 | 5.58 | .96 |
| V3-V1 Mean Dominant Hand | 4.87 | 5.09 | 2.61 | 3.78 | .08 |
| V3-V1 Mean Non-Dominant Hand | 2.49 | 3.74 | 2.21 | 3.48 | .78 |

TABLE 62

Finger Tap Test Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 Mean Dominant Hand | 51.34 | 6.40 | 52.05 | 5.10 | .68 |
| V3 Mean Non-Dominant Hand | 47.34 | 5.70 | 47.10 | 5.58 | .88 |
| V3-V1 Mean Dominant Hand | .85 | 4.69 | 2.61 | 3.78 | .16 |
| V3-V1 Mean Non-Dominant Hand | 1.66 | 4.43 | 2.21 | 3.48 | .64 |

TABLE 62a

Finger Tap Test Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 Mean Dominant Hand | 51.59 | 4.97 | 51.34 | 6.40 | .88 |
| V3 Mean Non-Dominant Hand | 47.01 | 6.47 | 47.34 | 5.70 | .85 |
| V3-V1 Mean Dominant Hand | 4.87 | 5.09 | .85 | 4.69 | <.01 |
| V3-V1 Mean Non-Dominant Hand | 2.49 | 3.74 | 1.66 | 4.43 | .47 |

TABLE 63

Finger Tap Test Visit 3: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Mean Dominant Hand | .90 | — | .45 | — |
| 500 mg/day vs. 250 mg/day | — | .95 | — | .48 |
| 500 mg/day vs. Placebo | — | .90 | — | .45 |
| 250 mg/day vs. Placebo | — | .99 | — | .49 |
| Mean Non-Dominant Hand | .98 | — | .49 | — |
| 500 mg/day vs. 250 mg/day | — | 1.00 | — | .50 |
| 500 mg/day vs. Placebo | — | .99 | — | .49 |
| 250 mg/day vs. Placebo | — | .98 | — | .49 |

TABLE 64

Finger Tap Test Visit Difference Scores: 250 mg/day, Placebo groups, and 500 mg/day groups

| | Between Groups Overall p (2-tailed) | Between Groups p (2-tailed) | Between Groups Overall p (1-tailed) | Between Groups p (1-tailed) |
|---|---|---|---|---|
| Mean Dominant Hand | .10 | — | <.01 | — |
| 500 mg/day vs. 250 mg/day | — | .19 | — | .10 |
| 500 mg/day vs. Placebo | — | .38 | — | .19 |
| 250 mg/day vs. Placebo | — | <.01 | — | <.01 |
| Mean Non-Dominant Hand | .75 | — | .37 | — |
| 500 mg/day vs. 250 mg/day | — | .96 | — | .48 |
| 500 mg/day vs. Placebo | — | .88 | — | .44 |
| 250 mg/day vs. Placebo | — | .73 | — | .37 |

TABLE 65

CVLT I & II Visit 1 to Visit 3: 250 mg/day group

| CVLT I & II Lists | Mean | Std. Dev. | Sig (1-tailed) | Sig (2-tailed) |
|---|---|---|---|---|
| List A Trial 1 V1 | 6.11 | 1.91 | <.01 | <.01 |
| List A Trial 1 V3 | 7.74 | 2.38 | | |
| List A Trial 5 V1 | 12.33 | 2.53 | .10 | .20 |
| List A Trial 5 V3 | 12.85 | 3.01 | | |
| List A Trials 1-5 V1 | 50.52 | 11.23 | .06 | .11 |
| List A Trials 1-5 V3 | 53.63 | 11.19 | | |
| List B V1 | 5.78 | 1.91 | .12 | .25 |
| List B V3 | 6.26 | 1.97 | | |
| List A Short Delay V1 | 10.56 | 2.89 | .01 | .02 |
| List A Short Delay V3 | 11.59 | 3.40 | | |
| List A Long Delay V1 | 10.26 | 2.74 | .04 | .08 |
| List A Long Delay V3 | 11.07 | 3.74 | | |

TABLE 66

CVLT I & II Visit 1 to Visit 3: Placebo group

| CVLT I & II Lists | Mean | Std. Dev. | Sig (1-tailed) | Sig (2-tailed) |
|---|---|---|---|---|
| List A Trial 1 V1 | 6.71 | 1.33 | <.01 | <.01 |
| List A Trial 1 V3 | 7.88 | 1.60 | | |
| List A Trial 5 V1 | 12.83 | 1.93 | .20 | .41 |
| List A Trial 5 V3 | 13.25 | 2.17 | | |
| List A Trials 1-5 V1 | 52.33 | 5.93 | .01 | .03 |
| List A Trials 1-5 V3 | 56.38 | 8.41 | | |
| List B V1 | 6.54 | 1.44 | .46 | .92 |
| List B V3 | 6.50 | 2.11 | | |
| List A Short Delay V1 | 11.50 | 1.56 | .12 | .24 |
| List A Short Delay V3 | 12.17 | 2.67 | | |

TABLE 66-continued

CVLT I & II Visit 1 to Visit 3: Placebo group

| CVLT I & II Lists | Mean | Std. Dev. | Sig (1-tailed) | Sig (2-tailed) |
|---|---|---|---|---|
| List A Long Delay V1 | 11.04 | 1.73 | <.01 | .01 |
| List A Long Delay V3 | 12.42 | 2.60 | | |

TABLE 67

CVLT I & II Visit 1 to Visit 3: 500 mg/day group

| CVLT I & II Lists | Mean | Std. Dev. | Sig (1-tailed) | Sig (2-tailed) |
|---|---|---|---|---|
| List A Trial 1 V1 | 6.58 | 1.64 | .02 | .05 |
| List A Trial 1 V3 | 7.58 | 2.21 | | |
| List A Trial 5 V1 | 11.83 | 2.01 | .04 | .07 |
| List A Trial 5 V3 | 12.71 | 2.33 | | |
| List A Trials 1-5 V1 | 49.04 | 9.29 | .02 | .05 |
| List A Trials 1-5 V3 | 52.79 | 10.87 | | |
| List B V1 | 6.67 | 1.74 | .25 | .50 |
| List B V3 | 6.33 | 2.33 | | |
| List A Short Delay V1 | 10.25 | 2.67 | .03 | .05 |
| List A Short Delay V3 | 11.21 | 3.01 | | |
| List A Long Delay V1 | 9.79 | 3.27 | .01 | .02 |
| List A Long Delay V3 | 10.92 | 3.05 | | |

TABLE 68

CVLT I & II Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| V3 CVLT I & II List A Trial 1 | 7.74 | 2.38 | 7.58 | 2.21 | .81 |
| V3 CVLT I & II List A Trial 5 | 12.85 | 3.01 | 12.71 | 2.33 | .85 |
| V3 CVLT I & II List A Trial 1-5 | 53.63 | 11.99 | 52.79 | 10.87 | .80 |
| V3 CVLT I & II List B Trial 1 | 6.26 | 1.97 | 6.33 | 2.33 | .90 |
| V3 CVLT I & II List A Short Delay | 11.59 | 3.40 | 11.21 | 3.01 | .67 |
| V3 CVLT I & II List A Long Delay | 11.07 | 3.74 | 10.92 | 3.05 | .87 |
| V3-V1 CVLT I & II Difference List A Trial 1 | 1.63 | 2.22 | 1.00 | 2.32 | .33 |
| V3-V1 CVLT I & II Difference List A Trial 5 | .52 | 2.05 | .88 | 2.27 | .56 |
| V3-V1 CVLT I & II Difference List A Trials 1-5 | 3.11 | 9.82 | 3.75 | 8.64 | .81 |
| V3-V1 CVLT I & II Difference List B Trial 6 | .48 | 2.12 | −.33 | 2.37 | .20 |
| V3-V1 CVLT I & II Difference List A Short Delay | 1.04 | 2.16 | .96 | 2.31 | .90 |
| V3-V1 CVLT I & II Difference List A Long Delay | .81 | 2.34 | 1.13 | 2.23 | .63 |

TABLE 69

CVLT I & II Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 CVLT I & II List A Trial 1 | 7.88 | 1.60 | 7.58 | 2.21 | .60 |
| V3 CVLT I & II List A Trial 5 | 13.25 | 2.17 | 12.71 | 2.33 | .41 |
| V3 CVLT I & II List A Trial 1-5 | 56.38 | 8.41 | 52.79 | 10.87 | .21 |
| V3 CVLT I & II List B Trial 1 | 6.50 | 2.11 | 6.33 | 2.33 | .80 |
| V3 CVLT I & II List A Short Delay | 12.17 | 2.67 | 11.21 | 3.01 | .25 |
| V3 CVLT I & II List A Long Delay | 12.42 | 2.60 | 10.92 | 3.05 | .07 |
| V3-V1 CVLT I & II Difference List A Trial 1 | 1.17 | 1.93 | 1.00 | 2.32 | .79 |
| V3-V1 CVLT I & II Difference List A Trial 5 | .42 | 2.41 | .88 | 2.27 | .50 |
| V3-V1 CVLT I & II Difference List A Trials 1-5 | 4.04 | 8.30 | 3.75 | 8.64 | .91 |
| V3-V1 CVLT I & II Difference List B Trial 1 | −.04 | 2.01 | −.33 | 2.37 | .65 |
| V3-V1 CVLT I & II Difference List A Short Delay | .67 | 2.71 | .96 | 2.31 | .69 |
| V3-V1 CVLT I & II Difference List A Long Delay | 1.38 | 2.39 | 1.13 | 2.23 | .71 |

TABLE 69a

CVLT I & II Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 CVLT I & II List A Trial 1 | 7.74 | 2.38 | 7.88 | 1.60 | .82 |
| V3 CVLT I & II List A Trial 5 | 12.85 | 3.01 | 13.25 | 2.17 | .60 |
| V3 CVLT I & II List A Trial 1-5 | 53.63 | 11.99 | 56.38 | 8.41 | .35 |
| V3 CVLT I & II List B Trial 1 | 6.26 | 1.97 | 6.50 | 2.11 | .66 |
| V3 CVLT I & II List A Short Delay | 11.59 | 3.40 | 12.17 | 2.67 | .51 |
| V3 CVLT I & II List A Long Delay | 11.07 | 3.74 | 12.42 | 2.60 | .15 |
| V3-V1 CVLT I & II Difference List A Trial 1 | 1.63 | 2.22 | 1.17 | 1.93 | .43 |

TABLE 69a-continued

CVLT I & II Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3-V1 CVLT I & II Difference List A Trial 5 | .52 | 2.05 | .42 | 2.41 | .87 |
| V3-V1 CVLT I & II Difference List A Trials 1-5 | 3.11 | 9.82 | 4.04 | 8.30 | .72 |
| V3-V1 CVLT I & II Difference List B Trial 1 | .48 | 2.12 | −.04 | 2.01 | .37 |
| V3-V1 CVLT I & II Difference List A Short Delay | 1.04 | 2.16 | .67 | 2.71 | .59 |
| V3-V1 CVLT I & II Difference List A Long Delay | .81 | 2.34 | 1.38 | 2.39 | .40 |

TABLE 70

CVLT I & II Visit 3: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| List A Trial 1 Total | .89 | | .45 | |
| 500 mg/day vs 250 mg/day | | .96 | | .48 |
| 500 mg/day vs Placebo | | .88 | | .44 |
| 250 mg/day vs Placebo | | .97 | | .49 |
| List A Trial 5 Total | .75 | | .37 | |
| 500 mg/day vs 250 mg/day | | .98 | | .49 |
| 500 mg/day vs Placebo | | .74 | | .37 |
| 250 mg/day vs Placebo | | .84 | | .42 |
| List A Trials 1-5 Total | .47 | | .24 | |
| 500 mg/day vs 250 mg/day | | .96 | | .48 |
| 500 mg/day vs Placebo | | .47 | | .24 |
| 250 mg/day vs Placebo | | .63 | | .31 |
| List B Total | .92 | | .46 | |
| 500 mg/day vs 250 mg/day | | .99 | | .50 |
| 500 mg/day vs Placebo | | .96 | | .48 |
| 250 mg/day vs Placebo | | .92 | | .46 |
| List A Short Delay Total | .55 | | .28 | |
| 500 mg/day vs 250 mg/day | | .90 | | .45 |
| 500 mg/day vs Placebo | | .53 | | .26 |
| 250 mg/day vs Placebo | | .78 | | .39 |
| List A Long Delay Total | .20 | | .10 | |
| 500 mg/day vs 250 mg/day | | .98 | | .49 |
| 500 mg/day vs Placebo | | .24 | | .12 |
| 250 mg/day vs Placebo | | .30 | | .15 |

TABLE 71

CVLT Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| List A Trial 1 Total | .56 | | .28 | |
| 500 mg/day vs 250 mg/day | | .56 | | .28 |
| 500 mg/day vs Placebo | | .96 | | .48 |
| 250 mg/day vs Placebo | | .73 | | .36 |
| List A Trial 5 Total | .76 | | .38 | |
| 500 mg/day vs 250 mg/day | | .84 | | .42 |
| 500 mg/day vs Placebo | | .76 | | .38 |
| 250 mg/day vs Placebo | | .99 | | .49 |
| List A Trials 1-5 Total | .93 | | .47 | |
| 500 mg/day vs 250 mg/day | | .97 | | .48 |
| 500 mg/day vs Placebo | | .99 | | .50 |
| 250 mg/day vs Placebo | | .93 | | .46 |
| List B Total | .40 | | .20 | |
| 500 mg/day vs 250 mg/day | | .38 | | .19 |
| 500 mg/day vs Placebo | | .89 | | .44 |
| 250 mg/day vs Placebo | | .67 | | .33 |
| List A Short Delay Total | .85 | | .42 | |
| 500 mg/day vs 250 mg/day | | .99 | | .50 |
| 500 mg/day vs Placebo | | .91 | | .45 |
| 250 mg/day vs Placebo | | .85 | | .42 |
| List A Long Delay Total | .69 | | .35 | |
| 500 mg/day vs 250 mg/day | | .88 | | .44 |
| 500 mg/day vs Placebo | | .93 | | .46 |
| 250 mg/day vs Placebo | | .67 | | .33 |

TABLE 72

ROCFT Visit 1 to Visit 3: 250 mg/day group

| ROCFT | Mean | Std. Dev. | Sig (1-tailed) | Sig (2-tailed) |
|---|---|---|---|---|
| Copy Raw Score V1 | 29.72 | 4.67 | .38 | .76 |
| Copy Raw Score V3 | 30.00 | 4.23 | | |
| Immediate Raw Score V1 | 21.39 | 5.22 | <.01 | <.01 |
| Immediate Raw Score V3 | 26.54 | 4.39 | | |
| Delayed Raw Score V1 | 21.63 | 5.34 | <.01 | <.01 |
| Delayed Raw Score V3 | 25.43 | 4.73 | | |
| Difference Raw Score V1 | −.24 | 2.20 | .03 | .07 |
| Difference Raw Score V3 | 1.11 | 2.75 | | |

TABLE 73

ROCFT Visit 1 to Visit 3: Placebo group

| ROCFT | Mean | Std. Dev. | Sig (1-tailed) | Sig (2-tailed) |
|---|---|---|---|---|
| Copy Raw Score V1 | 30.21 | 3.76 | .35 | .70 |
| Copy Raw Score V3 | 29.96 | 3.96 | | |
| Immediate Raw Score V1 | 21.38 | 4.17 | <.01 | <.01 |
| Immediate Raw Score V3 | 26.94 | 5.13 | | |
| Delayed Raw Score V1 | 20.94 | 3.67 | <.01 | <.01 |
| Delayed Raw Score V3 | 26.04 | 4.95 | | |
| Difference Raw Score V1 | .48 | 2.69 | .27 | .54 |
| Difference Raw Score V3 | .90 | 2.40 | | |

TABLE 74

ROCFT Visit 1 to Visit 3: 500 mg/day group

| ROCFT | Mean | Std. Dev. | Sig (1-tailed) | Sig (2-tailed) |
|---|---|---|---|---|
| Copy Raw Score V1 | 29.13 | 5.53 | .38 | .77 |
| Copy Raw Score V3 | 29.40 | 5.06 | | |
| Immediate Raw Score V1 | 19.48 | 6.79 | <.01 | <.01 |
| Immediate Raw Score V3 | 24.88 | 6.46 | | |
| Delayed Raw Score V1 | 19.00 | 7.11 | <.01 | <.01 |
| Delayed Raw Score V3 | 24.31 | 6.58 | | |
| Difference Raw Score V1 | .44 | 2.51 | .44 | .88 |
| Difference Raw Score V3 | .56 | 2.87 | | |

TABLE 75

ROCFT Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| Copy Raw Score V3 | 29.722 | 4.67 | 29.13 | 5.53 | .68 |
| Immediate Raw Score V3 | 21.39 | 5.22 | 19.48 | 6.79 | .26 |
| Delayed Raw Score V3 | 21.63 | 5.34 | 19.00 | 7.11 | .14 |
| Difference Raw Score V3 | −.24 | 2.20 | .44 | 2.51 | .31 |
| V3-V1 Copy Raw Score | .28 | 4.74 | .27 | 4.40 | 1.00 |
| V3-V1 Immediate Raw Score | 5.15 | 5.00 | 5.40 | 4.90 | .86 |
| V3-V1 Delayed Raw Score | 3.80 | 4.92 | 5.31 | 4.58 | .26 |
| V3-V1 Difference Raw Score | 1.35 | 3.70 | .13 | 4.02 | .26 |

TABLE 76

ROCFT Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| Copy Raw Score V3 | 30.21 | 3.76 | 29.13 | 5.53 | .43 |
| Immediate Raw Score V3 | 21.38 | 4.17 | 19.48 | 6.79 | .25 |
| Delayed Raw Score V3 | 20.94 | 3.67 | 19.00 | 7.11 | .24 |
| Difference Raw Score V3 | .48 | 2.69 | .44 | 2.51 | .96 |
| V3-V1 Copy Raw Score | −.25 | 3.16 | .27 | 4.40 | .64 |
| V3-V1 Immediate Raw Score | 5.56 | 5.81 | 5.40 | 4.90 | .92 |
| V3-V1 Delayed Raw Score | 5.10 | 4.82 | 5.31 | 4.58 | .88 |
| V3-V1 Difference Raw Score | .42 | 3.25 | .13 | 4.02 | .78 |

TABLE 76a

ROCFT Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| Copy Raw Score V3 | 29.722 | 4.67 | 30.21 | 3.76 | .69 |
| Immediate Raw Score V3 | 21.39 | 5.22 | 21.38 | 4.17 | .99 |
| Delayed Raw Score V3 | 21.63 | 5.34 | 20.94 | 3.67 | .60 |
| Difference Raw Score V3 | −.24 | 2.20 | .48 | 2.69 | .30 |
| V3-V1 Copy Raw Score | .28 | 4.74 | −.25 | 3.16 | .65 |
| V3-V1 Immediate Raw Score | 5.15 | 5.00 | 5.56 | 5.81 | .79 |
| V3-V1 Delayed Raw Score | 3.80 | 4.92 | 5.10 | 4.82 | .34 |
| V3-V1 Difference Raw Score | 1.35 | 3.70 | .42 | 3.25 | .35 |

TABLE 77

ROCFT Visit 3: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Copy Raw Score | .73 |  | .36 |  |
| 500 mg/day vs 250 mg/day |  | .89 |  | .45 |
| 500 mg/day vs Placebo |  | .71 |  | .35 |
| 250 mg/day vs Placebo |  | .93 |  | .46 |
| Immediate Raw Score | .38 |  | .19 |  |
| 500 mg/day vs 250 mg/day |  | .43 |  | .22 |
| 500 mg/day vs Placebo |  | .46 |  | .23 |
| 250 mg/day vs Placebo |  | 1.00 |  | .50 |
| Delayed Raw score | .23 |  | .11 |  |
| 500 mg/day vs 250 mg/day |  | .22 |  | .11 |
| 500 mg/day vs Placebo |  | .45 |  | .23 |
| 250 mg/day vs Placebo |  | .90 |  | .45 |
| Difference Raw Score | .50 |  | .25 |  |
| 500 mg/day vs 250 mg/day |  | .59 |  | .30 |
| 500 mg/day vs Placebo |  | 1.00 |  | .50 |
| 250 mg/day vs Placebo |  | .55 |  | .28 |

TABLE 78

ROCFT Visit Difference Scores: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Copy Raw Score | .88 |  | .44 |  |
| 500 mg/day vs 250 mg/day |  | 1.00 |  | .50 |
| 500 mg/day vs Placebo |  | .90 |  | .45 |
| 250 mg/day vs Placebo |  | .89 |  | .45 |
| Immediate Raw Score | .96 |  | .48 |  |
| 500 mg/day vs 250 mg/day |  | .98 |  | .49 |
| 500 mg/day vs Placebo |  | .99 |  | .50 |
| 250 mg/day vs Placebo |  | .96 |  | .48 |
| Delayed Raw Score | .47 |  | .23 |  |
| 500 mg/day vs 250 mg/day |  | .50 |  | .25 |
| 500 mg/day vs Placebo |  | .99 |  | .49 |
| 250 mg/day vs Placebo |  | .64 |  | .32 |
| Difference Raw Score | .46 |  | .23 |  |
| 500 mg/day vs 250 mg/day |  | .46 |  | .23 |
| 500 mg/day vs Placebo |  | .96 |  | .48 |
| 250 mg/day vs Placebo |  | .64 |  | .32 |

TABLE 79

Stroop Visit 1 to Visit 3: 250 mg/day group

| Stroop Trials | Mean | Std. Dev. | Sig (1-tailed) | Sig (2-tailed) |
|---|---|---|---|---|
| Word Trial V1 | 48.32 | 7.76 | .04 | .08 |
| Word Trial V3 | 46.34 | 8.40 |  |  |
| Color Trial V1 | 61.05 | 8.93 | <.01 | <.01 |
| Color Trial V3 | 53.34 | 8.97 |  |  |
| Interference Trial V1 | 91.85 | 21.66 | <.01 | <.01 |
| Interference Trial V3 | 72.82 | 15.01 |  |  |
| Difference V1 | 43.53 | 19.41 | <.01 | <.01 |
| Difference V3 | 26.00 | 8.71 |  |  |

TABLE 80

Stroop Visit 1 to Visit 3: Placebo group

| Stroop Trials | Mean | Std. Dev. | Sig (1-tailed) | Sig (2-tailed) |
|---|---|---|---|---|
| Word Trial V1 | 46.58 | 6.92 | .06 | .11 |
| Word Trial V3 | 45.25 | 7.04 |  |  |
| Color Trial V1 | 58.04 | 8.99 | <.01 | <.01 |
| Color Trial V3 | 52.45 | 8.68 |  |  |
| Interference Trial V1 | 86.32 | 18.51 | <.01 | <.01 |
| Interference Trial V3 | 71.97 | 15.48 |  |  |
| Difference V1 | 39.74 | 14.71 | <.01 | <.01 |
| Difference V3 | 26.72 | 11.73 |  |  |

TABLE 81

Stroop Visit 1 to Visit 3: 500 mg/day group

| Stroop Trials | Mean | Std. Dev. | Sig (1-tailed) | Sig (2-tailed) |
|---|---|---|---|---|
| Word Trial V1 | 46.69 | 7.03 | .07 | .15 |
| Word Trial V3 | 45.30 | 7.57 |  |  |
| Color Trial V1 | 60.12 | 10.61 | <.01 | <.01 |
| Color Trial V3 | 54.35 | 9.13 |  |  |
| Interference Trial V1 | 91.62 | 21.34 | <.01 | <.01 |
| Interference Trial V3 | 74.68 | 16.42 |  |  |
| Difference V1 | 44.93 | 18.02 | <.01 | <.01 |
| Difference V3 | 29.38 | 12.91 |  |  |

TABLE 82

Stroop Visit 3 and Visit Difference Scores: 250 mg/day group and 500 mg/day group

|  | 250 mg/day | | 500 mg/day | | |
|---|---|---|---|---|---|
|  | Mean | Std. Deviation | Mean | Std. Deviation | p-value |
| V3 Stroop Word Trial | 46.34 | 8.40 | 45.30 | 7.57 | .65 |
| V3 Stroop Color Trial | 53.35 | 8.97 | 54.35 | 9.13 | .69 |
| V3 Stroop Interference Trial | 72.82 | 15.01 | 74.68 | 16.42 | .68 |
| V3 Stroop Difference | 26.00 | 8.71 | 29.38 | 12.91 | .28 |
| V3-V1 Stroop Word Trial | −1.98 | 5.57 | −1.40 | 4.58 | .68 |
| V3-V1 Stroop Color Trial | −7.71 | 5.82 | −5.77 | 6.05 | .25 |
| V3-V1 Stroop Interference Trial | −19.03 | 11.95 | −16.95 | 11.48 | .53 |

TABLE 82-continued

Stroop Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| V3-V1 Stroop Difference | −17.53 | 14.62 | −15.55 | 12.76 | .61 |

TABLE 83

Stroop Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 Stroop Word Trial | 45.25 | 7.04 | 45.30 | 7.57 | .98 |
| V3 Stroop Color Trial | 52.45 | 8.68 | 54.35 | 9.13 | .46 |
| V3 Stroop Interference Trial | 71.97 | 15.48 | 74.68 | 16.42 | .56 |
| V3 Stroop Difference | 26.72 | 11.73 | 29.38 | 12.91 | .46 |
| V3-V1 Stroop Word Trial | −1.33 | 3.91 | −1.40 | 4.58 | .96 |
| V3-V1 Stroop Color Trial | −5.59 | 4.95 | −5.77 | 6.05 | .91 |
| V3-V1 Stroop Interference Trial | −14.35 | 8.84 | −16.95 | 11.48 | .38 |
| V3-V1 Stroop Difference | −13.02 | 10.17 | −15.55 | 12.76 | .45 |

TABLE 83a

Stroop Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 Stroop Word Trial | 46.34 | 8.40 | 45.25 | 7.04 | .62 |
| V3 Stroop Color Trial | 53.35 | 8.97 | 52.45 | 8.68 | .72 |
| V3 Stroop Interference Trial | 72.82 | 15.01 | 71.97 | 15.48 | .84 |
| V3 Stroop Difference | 26.00 | 8.71 | 26.72 | 11.73 | .81 |
| V3-V1 Stroop Word Trial | −1.98 | 5.57 | −1.33 | 3.91 | .63 |
| V3-V1 Stroop Color Trial | −7.71 | 5.82 | −5.59 | 4.95 | .17 |
| V3-V1 Stroop Interference Trial | −19.03 | 11.95 | −14.35 | 8.84 | .12 |
| V3-V1 Stroop Difference | −17.53 | 14.62 | −13.02 | 10.17 | .21 |

TABLE 84

Stroop Visit 3: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Word Trial | .85 | | .43 | |
| 500 mg/day vs 250 mg/day | | .88 | | .44 |
| 500 mg/day vs Placebo | | 1.00 | | .50 |
| 250 mg/day vs Placebo | | .87 | | .44 |
| Color Trial | .76 | | .38 | |
| 500 mg/day vs 250 mg/day | | .91 | | .46 |
| 500 mg/day vs Placebo | | .74 | | .37 |
| 250 mg/day vs Placebo | | .93 | | .47 |
| Interference Trial | .83 | | .41 | |
| 500 mg/day vs 250 mg/day | | .91 | | .45 |
| 500 mg/day vs Placebo | | .82 | | .41 |
| 250 mg/day vs Placebo | | .98 | | .49 |
| Difference Time | .54 | | .27 | |
| 500 mg/day vs 250 mg/day | | .53 | | .27 |
| 500 mg/day vs Placebo | | .69 | | .34 |
| 250 mg/day vs Placebo | | .97 | | .49 |

TABLE 85

Stroop Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Word Trial | .86 | | .43 | |
| 500 mg/day vs 250 mg/day | | .90 | | .45 |
| 500 mg/day vs Placebo | | 1.00 | | .50 |
| 250 mg/day vs Placebo | | .88 | | .44 |
| Color Trial | .33 | | .17 | |
| 500 mg/day vs 250 mg/day | | .44 | | .22 |
| 500 mg/day vs Placebo | | .99 | | .50 |

TABLE 85-continued

Stroop Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| 250 mg/day vs Placebo | | .38 | | .19 |
| Interference Trial | .32 | | .16 | |
| 500 mg/day vs 250 mg/day | | .78 | | .39 |
| 500 mg/day vs Placebo | | .69 | | .34 |
| 250 mg/day vs Placebo | | .28 | | .14 |
| Difference Time | .46 | | .23 | |
| 500 mg/day vs 250 mg/day | | .85 | | .42 |
| 500 mg/day vs Placebo | | .77 | | .39 |
| 250 mg/day vs Placebo | | .42 | | .21 |

TABLE 86

CPT Visit 1 to Visit 3: 250 mg/day group

| CPT Responses | Mean | Std. Dev. | Sig (1-tailed) | Sig (2-tailed) |
|---|---|---|---|---|
| Omissions V1 | 9.59 | 12.07 | .08 | .15 |
| Omissions V3 | 14.52 | 17.51 | | |
| Commissions V1 | 18.22 | 7.95 | .15 | .29 |
| Commissions V3 | 16.96 | 9.26 | | |
| Hit Reaction Time V1 | 362.62 | 61.02 | <.01 | .01 |
| Hit Reaction Time V3 | 397.19 | 83.16 | | |

TABLE 87

CPT Visit 1 to Visit 3: Placebo group

| CPT Responses | Mean | Std. Dev. | Sig (1-tailed) | Sig (2-tailed) |
|---|---|---|---|---|
| Omissions V1 | 6.79 | 7.81 | .13 | .26 |
| Omissions V3 | 10.25 | 17.90 | | |
| Commissions V1 | 16.83 | 8.17 | .03 | .05 |
| Commissions V3 | 14.42 | 10.49 | | |
| Hit Reaction Time V1 | 381.77 | 68.26 | .18 | .36 |
| Hit Reaction Time V3 | 390.68 | 89.97 | | |

TABLE 88

CPT Visit 1 to Visit 3: 500 mg/day group

| CPT Responses | Mean | Std. Dev. | Sig (1-tailed) | Sig (2-tailed) |
|---|---|---|---|---|
| Omissions V1 | 8.42 | 9.96 | .06 | .11 |
| Omissions V3 | 13.75 | 22.18 | | |
| Commissions V1 | 18.79 | 8.30 | <.01 | .01 |
| Commissions V3 | 14.92 | 9.73 | | |
| Hit Reaction Time V1 | 363.58 | 55.67 | <.01 | .01 |
| Hit Reaction Time V3 | 391.30 | 65.52 | | |

TABLE 89

CPT Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| V3 CPT Omissions | 14.52 | 17.51 | 13.75 | 22.18 | .89 |
| V3 CPT Commissions | 16.96 | 9.26 | 14.92 | 9.73 | .45 |
| V3 CPT Hit Reaction Time | 397.19 | 83.16 | 391.30 | 65.52 | .78 |
| V3-V1 CPT Omissions | 4.93 | 17.32 | 5.33 | 15.71 | .93 |
| V3-V1 CPT Commissions | −1.26 | 6.05 | −3.88 | 4.94 | .10 |
| V3-V1 CPT Hit Reaction Time | 34.57 | 66.00 | 27.71 | 48.82 | .68 |

TABLE 90

CPT Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 CPT Omissions | 10.25 | 17.90 | 13.75 | 22.18 | .55 |
| V3 CPT Commissions | 14.42 | 10.49 | 14.92 | 9.73 | .87 |
| V3 CPT Hit Reaction Time | 390.68 | 89.97 | 391.30 | 65.52 | .98 |
| V3-V1 CPT Omissions | 3.46 | 14.63 | 5.33 | 15.71 | .67 |
| V3-V1 CPT Commissions | −2.42 | 5.79 | −3.88 | 4.94 | .35 |
| V3-V1 CPT Hit Reaction Time | 8.91 | 46.27 | 27.71 | 48.82 | .18 |

TABLE 90a

CPT Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 CPT Omissions | 14.52 | 17.51 | 10.25 | 17.90 | .39 |
| V3 CPT Commissions | 16.96 | 9.26 | 14.42 | 10.49 | .36 |
| V3 CPT Hit Reaction Time | 397.19 | 83.16 | 390.68 | 89.97 | .79 |
| V3-V1 CPT Omissions | 4.93 | 17.32 | 3.46 | 14.63 | .75 |

TABLE 90a-continued

CPT Visit 3 and Visit Difference Scores: 250 mg/day group and Placebo group

|  | 250 mg/day | | Placebo | | |
|---|---|---|---|---|---|
|  | Mean | Std. Deviation | Mean | Std. Deviation | p-value |
| V3-V1 CPT Commissions | −1.26 | 6.05 | −2.42 | 5.79 | .49 |
| V3-V1 CPT Hit Reaction Time | 34.57 | 66.00 | 8.91 | 46.27 | .12 |

TABLE 91

CPT Visit 3: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Omissions Total | .71 |  | .35 |  |
| 500 mg/day vs 250 mg/day |  | .99 |  | .49 |
| 500 mg/day vs Placebo |  | .80 |  | .40 |
| 250 mg/day vs Placebo |  | .71 |  | .36 |
| Commissions Total | .62 |  | .31 |  |
| 500 mg/day vs 250 mg/day |  | .74 |  | .37 |
| 500 mg/day vs Placebo |  | .98 |  | .49 |
| 250 mg/day vs Placebo |  | .63 |  | .31 |
| Hit Reaction Time Total | .95 |  | .48 |  |
| 500 mg/day vs 250 mg/day |  | .96 |  | .48 |
| 500 mg/day vs Placebo |  | 1.00 |  | .50 |
| 250 mg/day vs Placebo |  | .96 |  | .48 |

TABLE 92

CPT Visit Difference Scores: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| Omissions Total | .91 |  | .46 |  |
| 500 mg/day vs 250 mg/day |  | 1.00 |  | .50 |
| 500 mg/day vs Placebo |  | .91 |  | .46 |
| 250 mg/day vs Placebo |  | .94 |  | .47 |
| Commissions Total | .26 |  | .13 |  |
| 500 mg/day vs 250 mg/day |  | .23 |  | .11 |
| 500 mg/day vs Placebo |  | .64 |  | .32 |
| 250 mg/day vs Placebo |  | .75 |  | .37 |
| Hit Reaction Time Total | .24 |  | .12 |  |

TABLE 92-continued

CPT Visit Difference Scores: 250 mg/day, Placebo, and 500 mg/day groups

|  | Between Groups Overall p (2-tailed) | Between groups p (2-tailed) | Between Groups Overall p (1-tailed) | Between groups p (1-tailed) |
|---|---|---|---|---|
| 500 mg/day vs 250 mg/day |  | .90 |  | .45 |
| 500 mg/day vs Placebo |  | .47 |  | .23 |
| 250 mg/day vs Placebo |  | .23 |  | .11 |

TABLE 93

Ruff 2 & 7 Visit 1 to Visit 3: 250 mg/day group

| Ruff 2 & 7 | Mean | Std. Dev. | Sig (1-tailed) | Sig (2-tailed) |
|---|---|---|---|---|
| Total Speed T Score V1 | 45.74 | 11.45 | <.01 | <.01 |
| Total Speed T Score V3 | 54.85 | 11.63 |  |  |
| Total Accuracy T Score V1 | 47.41 | 7.49 | <.01 | <.01 |
| Total Accuracy T Score V3 | 53.00 | 4.42 |  |  |
| Speed Difference Score V1 | .01 | .02 | .43 | .86 |
| Speed Difference Score V3 | .01 | .03 |  |  |
| Accuracy Difference Score V1 | .02 | .03 | .26 | .51 |
| Accuracy Difference Score V3 | .01 | .03 |  |  |
| Total Difference Score V1 | .01 | .02 | .40 | .80 |
| Total Difference Score V3 | .02 | .02 |  |  |

TABLE 94

Ruff 2 & 7 Visit 1 to Visit 3: Placebo group

| Ruff 2 & 7 | Mean | Std. Dev. | Sig (1-tailed) | Sig (2-tailed) |
|---|---|---|---|---|
| Total Speed T Score V1 | 43.58 | 8.72 | <.01 | <.01 |
| Total Speed T Score V3 | 50.13 | 10.20 |  |  |
| Total Accuracy T Score V1 | 44.29 | 9.71 | <.01 | <.01 |
| Total Accuracy T Score V3 | 51.13 | 8.01 |  |  |
| Speed Difference Score V1 | .02 | .03 | .26 | .53 |
| Speed Difference Score V3 | .01 | .02 |  |  |
| Accuracy Difference Score V1 | .02 | .04 | .30 | .59 |
| Accuracy Difference Score V3 | .02 | .03 |  |  |
| Total Difference Score V1 | .03 | .04 | <.01 | .01 |
| Total Difference Score V3 | .01 | .01 |  |  |

TABLE 95

Ruff 2 & 7 Visit 1 to Visit 3: 500 mg/day group

| Ruff 2 & 7 | Mean | Std. Dev. | Sig (1-tailed) | Sig (2-tailed) |
|---|---|---|---|---|
| Total Speed T Score V1 | 44.33 | 12.11 | <.01 | <.01 |
| Total Speed T Score V3 | 53.75 | 10.34 |  |  |
| Total Accuracy T Score V1 | 42.71 | 9.16 | <.01 | <.01 |
| Total Accuracy T Score V3 | 49.88 | 8.41 |  |  |
| Speed Difference Score V1 | .01 | .02 | .05 | .10 |
| Speed Difference Score V3 | .02 | .04 |  |  |
| Accuracy Difference Score V1 | .02 | .04 | .01 | .02 |
| Accuracy Difference Score V3 | .00 | .01 |  |  |
| Total Difference Score V1 | .02 | .02 | .22 | .43 |
| Total Difference Score V3 | .02 | .03 |  |  |

TABLE 96

Ruff 2 & 7 Visit 3 and Visit Difference Scores: 250 mg/day group and 500 mg/day group

|  | 250 mg/day | | 500 mg/day | | |
| --- | --- | --- | --- | --- | --- |
|  | Mean | Std. Deviation | Mean | Std. Deviation | p-value |
| Total Speed T Score V3 | 54.85 | 11.63 | 53.75 | 10.34 | .72 |
| Total Accuracy T Score V3 | 53.00 | 4.42 | 49.88 | 8.41 | .10 |
| Speed Difference Score V3 | .01 | .03 | .02 | .04 | .38 |
| Accuracy Difference Score V3 | .01 | .03 | .00 | .01 | .14 |
| Total Difference Score V3 | .02 | .02 | .02 | .03 | .37 |
| Total Speed T Score V3-V1 | 9.11 | 4.93 | 9.42 | 5.82 | .84 |
| Total Accuracy T Score V3-V1 | 5.59 | 5.93 | 7.17 | 10.54 | .51 |
| Speed Difference Score V3-V1 | .00 | .03 | .01 | .04 | .26 |
| Accuracy Difference Score V3-V1 | −.01 | .04 | −.02 | .04 | .19 |
| Total Difference Score V3-V1 | .00 | .03 | .01 | .04 | .61 |

TABLE 97

Ruff 2 & 7 Visit 3 and Visit Difference Scores: Placebo group and 500 mg/day group

|  | Placebo | | 500 mg/day | | |
| --- | --- | --- | --- | --- | --- |
|  | Mean | Std. Deviation | Mean | Std. Deviation | p-value |
| Total Speed T Score V3 | 50.13 | 10.20 | 53.75 | 10.34 | .23 |
| Total Accuracy T Score V3 | 51.13 | 8.01 | 49.88 | 8.41 | .60 |
| Speed Difference Score V3 | .01 | .02 | .02 | .04 | .32 |
| Accuracy Difference Score V3 | .02 | .03 | .00 | .01 | .09 |
| Total Difference Score V3 | .01 | .01 | .02 | .03 | .04 |
| Total Speed T Score V3-V1 | 6.54 | 3.89 | 9.42 | 5.82 | .05 |
| Total Accuracy T Score V3-V1 | 6.83 | 4.93 | 7.17 | 10.54 | .89 |
| Speed Difference Score V3-V1 | −.01 | .04 | .01 | .04 | .13 |
| Accuracy Difference Score V3-V1 | −.00 | .04 | −.02 | .04 | .19 |
| Total Difference Score V3-V1 | −.02 | .04 | .01 | .04 | .02 |

TABLE 97A

Ruff 2 & 7 Visit 3 and Visit Difference Scores: 250 mg/day group and Placebo group

|  | 250 mg/day | | Placebo | | |
| --- | --- | --- | --- | --- | --- |
|  | Mean | Std. Deviation | Mean | Std. Deviation | p-value |
| Total Speed T Score V3 | 54.85 | 11.63 | 50.13 | 10.20 | .13 |
| Total Accuracy T Score V3 | 53.00 | 4.42 | 51.13 | 8.01 | .30 |
| Speed Difference Score V3 | .01 | .03 | .01 | .02 | .87 |
| Accuracy Difference Score V3 | .01 | .03 | .02 | .03 | .81 |
| Total Difference Score V3 | .02 | .02 | .01 | .01 | .15 |
| Total Speed T Score V3-V1 | 9.11 | 4.93 | 6.54 | 3.89 | .05 |
| Total Accuracy T Score V3-V1 | 5.59 | 5.93 | 6.83 | 4.93 | .42 |
| Speed Difference Score V3-V1 | .00 | .03 | −.01 | .04 | .52 |
| Accuracy Difference Score V3-V1 | −.01 | .04 | −.00 | .04 | .96 |
| Total Difference Score V3-V1 | .00 | .03 | −.02 | .04 | .02 |

TABLE 98

Ruff 2 & 7 Visit 3: 250 mg/day, Placebo, and 500 mg/day groups

|  | Between Groups Overall p (2-tailed) | Between groups p (2-tailed) | Between Groups Overall p (1-tailed) | Between groups p (1-tailed) |
| --- | --- | --- | --- | --- |
| Total Speed T Score | .28 |  | .14 |  |
| 500 mg/day vs 250 mg/day |  | .93 |  | .47 |
| 500 mg/day vs Placebo |  | .48 |  | .24 |
| 250 mg/day vs Placebo |  | .27 |  | .13 |
| Total Accuracy T Score | .29 |  | .14 |  |
| 500 mg/day vs 250 mg/day |  | .26 |  | .13 |
| 500 mg/day vs Placebo |  | .81 |  | .41 |
| 250 mg/day vs Placebo |  | .62 |  | .31 |
| Speed Difference Score | .51 |  | .26 |  |
| 500 mg/day vs 250 mg/day |  | .61 |  | .30 |
| 500 mg/day vs Placebo |  | .54 |  | .27 |
| 250 mg/day vs Placebo |  | .99 |  | .50 |
| Accuracy Difference Score | .25 |  | .12 |  |
| 500 mg/day vs 250 mg/day |  | .38 |  | .19 |
| 500 mg/day vs Placebo |  | .27 |  | .13 |
| 250 mg/day vs Placebo |  | .96 |  | .48 |
| Total Difference Score | .12 |  | .06 |  |
| 500 mg/day vs 250 mg/day |  | .54 |  | .27 |
| 500 mg/day vs Placebo |  | .09 |  | .05 |
| 250 mg/day vs Placebo |  | .51 |  | .25 |

TABLE 99

Ruff 2 & 7 Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Total Speed T Score | .09 | | .05 | |
| 500 mg/day vs 250 mg/day | | .97 | | .49 |
| 500 mg/day vs Placebo | | .12 | | .06 |
| 250 mg/day vs Placebo | | .16 | | .08 |
| Total Accuracy T Score | .73 | | .36 | |
| 500 mg/day vs 250 mg/day | | .74 | | .37 |
| 500 mg/day vs Placebo | | .99 | | .49 |
| 250 mg/day vs Placebo | | .83 | | .41 |
| Speed Difference Score | .26 | | .31 | |
| 500 mg/day vs 250 mg/day | | .57 | | .28 |
| 500 mg/day vs Placebo | | .24 | | .12 |
| 250 mg/day vs Placebo | | .78 | | .39 |
| Accuracy Difference Score | .33 | | .16 | |
| 500 mg/day vs 250 mg/day | | .40 | | .20 |
| 500 mg/day vs Placebo | | .39 | | .19 |
| 250 mg/day vs Placebo | | 1.00 | | .50 |
| Total Difference Score | .02 | | .01 | |
| 500 mg/day vs 250 mg/day | | .87 | | .43 |
| 500 mg/day vs Placebo | | .03 | | .01 |
| 250 mg/day vs Placebo | | .07 | | .04 |

TABLE 100

WCST Visit 3: 250 mg/day group and 500 mg/day group

| | 250 mg/day | | 500 mg/day | | |
|---|---|---|---|---|---|
| | Mean | Std. Deviation | Mean | Std. Deviation | p-value |
| V3 Total Cards Used | 90.88 | 20.17 | 89.57 | 18.50 | .81 |
| V3 Number of Categories Achieved | 5.69 | .88 | 5.87 | .46 | .39 |
| V3 Total Errors | 19.73 | 18.03 | 19.00 | 12.05 | .87 |
| V3 Total Perserverative Errors | 8.54 | 4.76 | 9.13 | 5.18 | .68 |
| V3 Number of Trials to Get into Category | 15.19 | 14.91 | 13.78 | 7.05 | .68 |
| V3 Number of Trials to Complete Category | 71.15 | 10.80 | 70.57 | 9.31 | .84 |

TABLE 101

WCST Visit 3: Placebo group and 500 mg/day group

| | Placebo | | 500 mg/day | | |
|---|---|---|---|---|---|
| | Mean | Std. Deviation | Mean | Std. Deviation | p-value |
| V3 Total Cards Used | 85.46 | 15.91 | 89.57 | 18.50 | .42 |
| V3 Number of Categories Achieved | 5.96 | .20 | 5.87 | .46 | .39 |
| V3 Total Errors | 13.83 | 7.35 | 19.00 | 12.05 | .08 |
| V3 Total Perserverative Errors | 7.54 | 4.22 | 9.13 | 5.18 | .25 |
| V3 Number of Trials to Get into Category | 11.58 | 3.53 | 13.78 | 7.05 | .18 |
| V3 Number of Trials to Complete Category | 71.63 | 10.50 | 70.57 | 9.31 | .72 |

TABLE 102

WCST Visit 3: 250 mg/day group and Placebo group

| | 250 mg/day | | Placebo | | |
|---|---|---|---|---|---|
| | Mean | Std. Deviation | Mean | Std. Deviation | p-value |
| V3 Total Cards Used | 90.88 | 20.17 | 85.46 | 15.91 | .30 |
| V3 Number of Categories Achieved | 5.69 | .88 | 5.96 | .20 | .16 |
| V3 Total Errors | 19.73 | 18.03 | 13.83 | 7.35 | .14 |
| V3 Total Perserverative Errors | 8.54 | 4.76 | 7.54 | 4.22 | .44 |
| V3 Number of Trials to Get into Category | 15.19 | 14.91 | 11.58 | 3.53 | .25 |
| V3 Number of Trials to Complete Category | 71.15 | 10.80 | 71.63 | 10.50 | .88 |

TABLE 103

WCST Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Total Cards Used | .56 | | .28 | |
| 500 mg/day vs 250 mg/day | | .97 | | .48 |
| 500 mg/day vs Placebo | | .72 | | .36 |
| 250 mg/day vs Placebo | | .55 | | .28 |
| Number of Categories Achieved | .28 | | .14 | |
| 500 mg/day vs 250 mg/day | | .56 | | .28 |
| 500 mg/day vs Placebo | | .87 | | .43 |

TABLE 103-continued

WCST Visit Difference Scores: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| 250 mg/day vs Placebo | | .27 | | .13 |
| Total Errors | .25 | | .13 | |
| 500 mg/day vs 250 mg/day | | .98 | | .49 |
| 500 mg/day vs Placebo | | .39 | | .19 |
| 250 mg/day vs Placebo | | .27 | | .14 |
| Total Perseverative Errors | .51 | | .26 | |
| 500 mg/day vs 250 mg/day | | .90 | | .45 |
| 500 mg/day vs Placebo | | .49 | | .24 |
| 250 mg/day vs Placebo | | .74 | | .37 |
| Number of Trials to Get into Category | .44 | | .22 | |
| 500 mg/day vs 250 mg/day | | .87 | | .44 |
| 500 mg/day vs Placebo | | .73 | | .37 |
| 250 mg/day vs Placebo | | .41 | | .21 |
| Number of Trials to Complete Category | .94 | | .47 | |
| 500 mg/day vs 250 mg/day | | .98 | | .49 |
| 500 mg/day vs Placebo | | .93 | | .47 |
| 250 mg/day vs Placebo | | .99 | | .49 |

TRAIL TABLE 104

Making Test Visit 1 to Visit 3: 250 mg/day group

| Trail Making | Mean | Std. Dev. | Sig (1-tailed) | Sig (2-tailed) |
|---|---|---|---|---|
| Trail Making A V1 | 11.16 | 3.36 | .03 | .07 |
| Trail Making A V3 | 9.37 | 3.87 | | |
| Trail Making B V1 | 29.15 | 13.31 | <.01 | <.01 |
| Trail Making B V3 | 18.40 | 5.80 | | |
| Trail Making B-A V1 | 17.99 | 13.77 | <.01 | <.01 |
| Trail Making B-A V3 | 9.00 | 3.95 | | |

TRAIL TABLE 105

Making Test Visit 1 to Visit 3: Placebo group

| Trail Making | Mean | Std. Dev. | Sig (1-tailed) | Sig (2-tailed) |
|---|---|---|---|---|
| Trail Making A V1 | 12.47 | 5.50 | <.01 | <.01 |
| Trail Making A V3 | 8.71 | 2.45 | | |
| Trail Making B V1 | 26.10 | 12.06 | <.01 | <.01 |
| Trail Making B V3 | 18.36 | 8.16 | | |
| Trail Making B-A V1 | 13.62 | 11.74 | .03 | .06 |
| Trail Making B-A V3 | 9.67 | 7.56 | | |

TABLE 106

Trail Making Test Visit 1 to Visit 3: 500 mg/day group

| Trail Making | Mean | Std. Dev. | Sig (1-tailed) | Sig (2-tailed) |
|---|---|---|---|---|
| Trail Making A V1 | 12.89 | 3.91 | <.01 | <.01 |
| Trail Making A V3 | 9.28 | 3.12 | | |
| Trail Making B V1 | 28.60 | 12.16 | .03 | .05 |
| Trail Making B V3 | 23.02 | 15.40 | | |
| Trail Making B-A V1 | 15.71 | 10.45 | .25 | .50 |
| Trail Making B-A V3 | 13.73 | 15.69 | | |

TABLE 107

Trail Making Test Visit 3 and Visit Difference Scores: 250 mg/day group and 500 mg/day group

| | 250 mg/day | | 500 mg/day | | |
|---|---|---|---|---|---|
| | Mean | Std. Deviation | Mean | Std. Deviation | p-value |
| V3 Trail Making A | 9.37 | 3.87 | 9.28 | 3.12 | .93 |
| V3 Trail Making B | 18.40 | 5.80 | 23.02 | 15.40 | .15 |
| V3 Trail Making B-A | 9.00 | 3.95 | 13.73 | 15.69 | .14 |
| V3-V1 Trail Making A | −1.80 | 4.87 | −3.60 | 4.05 | .16 |
| V3-V1 Trail Making B | −10.75 | 13.13 | −5.58 | 13.40 | .17 |
| V3-V1 Trail Making B-A | −8.99 | 13.42 | −1.98 | 14.07 | .08 |

TABLE 108

Trail Making Test Visit 3 and Visit Difference Scores: Placebo group and 500 mg/day group

| | Placebo | | 500 mg/day | | |
|---|---|---|---|---|---|
| | Mean | Std. Deviation | Mean | Std. Deviation | p-value |
| V3 Trail Making A | 8.71 | 2.45 | 9.28 | 3.12 | .48 |
| V3 Trail Making B | 18.36 | 8.16 | 23.02 | 15.40 | .20 |
| V3 Trail Making B-A | 9.67 | 7.56 | 13.73 | 15.69 | .26 |
| V3-V1 Trail Making A | −3.76 | 4.98 | −3.60 | 4.05 | .90 |
| V3-V1 Trail Making B | −7.74 | 8.81 | −5.58 | 13.40 | .51 |
| V3-V1 Trail Making B-A | −3.96 | 9.73 | −1.98 | 14.07 | .57 |

TABLE 108a

Trail Making Test Visit 3 and Visit Difference Scores: 250 mg/day group and Placebo group

| | 250 mg/day | | Placebo | | |
|---|---|---|---|---|---|
| | Mean | Std. Deviation | Mean | Std. Deviation | p-value |
| V3 Trail Making A | 9.37 | 3.87 | 8.71 | 2.45 | .48 |
| V3 Trail Making B | 18.40 | 5.80 | 18.36 | 8.16 | .98 |
| V3 Trail Making B-A | 9.00 | 3.95 | 9.67 | 7.56 | .69 |

TABLE 108a-continued

Trail Making Test Visit 3 and Visit Difference Scores:
250 mg/day group and Placebo group

| | 250 mg/day | | Placebo | | |
|---|---|---|---|---|---|
| | Mean | Std. Deviation | Mean | Std. Deviation | p-value |
| V3-V1 Trail Making A | −1.80 | 4.87 | −3.76 | 4.98 | .16 |
| V3-V1 Trail Making B | −10.75 | 13.13 | −7.74 | 8.81 | .35 |
| V3-V1 Trail Making B-A | −8.99 | 13.42 | −3.96 | 9.73 | .14 |

TABLE 109

Trail Making Test Visit 3: 250 mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Trail Making A | .74 | | .37 | |
| 500 mg/day vs 250 mg/day | | 1.00 | | .50 |
| 500 mg/day vs Placebo | | .81 | | .41 |
| 250 mg/day vs Placebo | | .75 | | .38 |
| Trail Making B | .21 | | .10 | |
| 500 mg/day vs 250 mg/day | | .26 | | .13 |
| 500 mg/day vs Placebo | | .28 | | .14 |
| 250 mg/day vs Placebo | | 1.00 | | .50 |
| Trail Making B-A | .21 | | .11 | |
| 500 mg/day vs 250 mg/day | | .23 | | .11 |
| 500 mg/day vs Placebo | | .35 | | .18 |
| 250 mg/day vs Placebo | | .97 | | .49 |

TABLE 110

Trail Making Test Visit Difference Scores: 250
mg/day, Placebo, and 500 mg/day groups

| | Between Groups Overall p (2-tailed) | Between groups p (2-tailed) | Between Groups Overall p (1-tailed) | Between groups p (1-tailed) |
|---|---|---|---|---|
| Trail Making A | .25 | | .12 | |
| 500 mg/day vs 250 mg/day | | .36 | | .18 |
| 500 mg/day vs Placebo | | .99 | | .50 |
| 250 mg/day vs Placebo | | .30 | | .15 |
| Trail Making B | .31 | | .15 | |
| 500 mg/day vs 250 mg/day | | .28 | | .14 |
| 500 mg/day vs Placebo | | .81 | | .40 |
| 250 mg/day vs Placebo | | .65 | | .32 |
| Trail Making B-A | .13 | | .06 | |
| 500 mg/day vs 250 mg/day | | .12 | | .06 |
| 500 mg/day vs Placebo | | .85 | | .42 |
| 250 mg/day vs Placebo | | .33 | | .17 |

TABLE 111

MOSES Visit 1 to Visit 3: 250 mg/day group

| MOSES | Mean | Std. Dev. | Sig (1-tailed) | Sig (2-tailed) |
|---|---|---|---|---|
| V2 MOSES | 1.30 | 1.61 | .17 | .34 |
| V3 MOSES | 1.04 | 1.58 | | |

TABLE 112

MOSES Visit 1 to Visit 3: Placebo group

| MOSES | Mean | Std. Dev. | Sig (1-tailed) | Sig (2-tailed) |
|---|---|---|---|---|
| V2 MOSES | .59 | 1.14 | .21 | .42 |
| V3 MOSES | .45 | 1.53 | | |

TABLE 113

MOSES Visit 1 to Visit 3: 500 mg/day group

| MOSES | Mean | Std. Dev. | Sig (1-tailed) | Sig (2-tailed) |
|---|---|---|---|---|
| V2 MOSES | .81 | 1.40 | .04 | .07 |
| V3 MOSES | .38 | .97 | | |

TABLE 114

MOSES Visit 3 and Visit Difference Scores:
250 mg/day group and 500 mg/day group

| | 250 mg/day | | 500 mg/day | | |
|---|---|---|---|---|---|
| | Mean | Std. Deviation | Mean | Std. Deviation | p-value |
| V3 MOSES | 1.04 | 1.58 | .38 | .97 | .11 |
| V3-V2 Score | −.26 | 1.29 | −.43 | 1.03 | .64 |

TABLE 115

MOSES Visit 3 and Visit Difference Scores: Placebo group and 500 mg/day group

|  | Placebo | | 500 mg/day | | |
| --- | --- | --- | --- | --- | --- |
|  | Mean | Std. Deviation | Mean | Std. Deviation | p-value |
| V3 MOSES | .45 | 1.53 | .38 | .97 | .85 |
| V3-V2 Score | −.14 | .77 | −.43 | 1.03 | .30 |

TABLE 115a

MOSES Visit 3 and Visit Difference Scores: 250 mg/day group and Placebo group

|  | 250 mg/day | | Placebo | | |
| --- | --- | --- | --- | --- | --- |
|  | Mean | Std. Deviation | Mean | Std. Deviation | p-value |
| V3 MOSES | 1.04 | 1.58 | .45 | 1.53 | .21 |
| V3-V2 Score | −.26 | 1.29 | −.14 | .77 | .70 |

TABLE 116

MOSES Visit 3: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
| --- | --- | --- | --- | --- |
| MOSES Score | .23 | — | .11 | — |
| 500 mg/day vs. 250 mg/day | — | .27 | — | .13 |
| 500 mg/day vs. Placebo | — | .98 | — | .49 |
| 250 mg/day vs. Placebo | — | .34 | — | .17 |

TABLE 117

MOSES Visit Difference Scores: 250 mg/day, Placebo groups, and 500 mg/day groups

|  | Between Groups Overall p (2-tailed) | Between Groups p (2-tailed) | Between Groups Overall p (1-tailed) | Between Groups p (1-tailed) |
| --- | --- | --- | --- | --- |
| MOSES Score | .66 | — | .33 | — |
| 500 mg/day vs. 250 mg/day | — | .86 | — | .43 |
| 500 mg/day vs. Placebo | — | .64 | — | .32 |
| 250 mg/day vs. Placebo | — | .92 | — | .46 |

What is claimed is:

1. A method for improving motor speed and control of a hand or finger of a healthy human subject comprising a step of administering an effective amount of citidine-5'-diphosphocholine (hereinafter referred to as citicoline) or a salt thereof to a healthy human subject.

2. The method according to claim 1, wherein the effective amount of citicoline administered is 5 mg or more and 4.0 g or less per day.

3. The method according to claim 1, wherein the effective amount of citicoline administered is 100 mg or more and 1.0 g or less per day.

4. The method according to claim 1, wherein the effective amount of citicoline administered is 250 mg or more and 500 mg or less per day.

5. The method according to claim 1, wherein the effective amount of citicoline administered is 250 mg per day.

6. The method according to claim 1, wherein the effective amount of citicoline administered 500 mg or less per day.

7. The method according to claim 1, wherein the citicoline is administered for at least 1 day and at most 1 year.

8. The method according to claim 1, wherein the citicoline is administered for at least 1 day and at most 4 weeks.

9. The method of claim 1, wherein the citicoline or a salt thereof is administered alone in an amount of 5 mg or more and 4.0 g or less per day.

10. The method of claim 1, wherein the citicoline or a salt thereof is administered orally.

\* \* \* \* \*